(12) United States Patent
Lavinder et al.

(10) Patent No.: US 10,175,249 B2
(45) Date of Patent: *Jan. 8, 2019

(54) PROTEOMIC IDENTIFICATION OF ANTIBODIES

(71) Applicant: BOARD OF REGENTS, THE UNIVERSITY OF TEXAS SYSTEM, Austin, TX (US)

(72) Inventors: Jason Lavinder, Round Rock, TX (US); Daniel Boutz, Austin, TX (US); Yariv Wine, Austin, TX (US); Edward M. Marcotte, Austin, TX (US); George Georgiou, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 265 days.

This patent is subject to a terminal disclaimer.

(21) Appl. No.: 14/865,302

(22) Filed: Sep. 25, 2015

(65) Prior Publication Data

US 2016/0146830 A1 May 26, 2016

Related U.S. Application Data

(63) Continuation of application No. 13/684,395, filed on Nov. 23, 2012, now Pat. No. 9,146,241, and a continuation-in-part of application No. 14/809,651, filed on Jul. 27, 2015, which is a continuation of application No. 13/109,467, filed on May 17, 2011, now Pat. No. 9,090,674.

(60) Provisional application No. 61/563,380, filed on Nov. 23, 2011, provisional application No. 61/377,816, filed on Aug. 27, 2010, provisional application No. 61/345,538, filed on May 17, 2010.

(51) Int. Cl.
*G01N 33/53* (2006.01)
*G01N 33/68* (2006.01)
*G01N 33/531* (2006.01)
*C12Q 1/6874* (2018.01)
*C40B 30/04* (2006.01)

(52) U.S. Cl.
CPC ....... *G01N 33/6857* (2013.01); *C12Q 1/6874* (2013.01); *G01N 33/531* (2013.01); *G01N 33/6848* (2013.01); *G01N 33/6854* (2013.01); *C40B 30/04* (2013.01)

(58) Field of Classification Search
None
See application file for complete search history.

(56) References Cited

U.S. PATENT DOCUMENTS

| | | | |
|---|---|---|---|
| 9,090,674 B2 * | 7/2015 | Reddy | C07K 16/065 |
| 9,146,241 B2 * | 9/2015 | Lavinder | G01N 33/531 |
| 2006/0233812 A1 | 10/2006 | Burnie et al. | |
| 2007/0172887 A1 | 7/2007 | Takacs et al. | |
| 2011/0312505 A1 | 12/2011 | Reddy et al. | |
| 2012/0308555 A1 | 12/2012 | Polakiewicz et al. | |
| 2012/0312505 A1 | 12/2012 | Youbi-Idrissi | |

FOREIGN PATENT DOCUMENTS

| WO | WO 2003-052416 | 6/2003 |
|---|---|---|
| WO | WO 2005-084134 | 9/2005 |
| WO | WO 2008-079914 | 7/2008 |
| WO | WO 2009-100896 | 8/2009 |
| WO | WO 2010-082456 | 7/2010 |
| WO | WO 2011-146514 | 11/2011 |

OTHER PUBLICATIONS

Arnaout, "Specificity and overlap in gene segment-defined antibody repertoires,"*BMC Genomics*, 6:148, 2005.
Behrendt et al., "The role of somatic mutation in determining the affinity of anti-DNA antibodies," *Clin Exp Immunol*, 131:182-189, 2003.
Boudinot et al., "New perspectives for large-scale repertoire analysis of immune receptors," *Molecular Immunology*, 45:2437-2445, 2008.
Boyd et al., "Measurement and clinical monitoring of human lymphocyte clonality by massively parallel V-D-J pyrosequencing," *Science Translational Medicine*, 1(12):12ra23, 2009.
Burgoon et al., "Laser-capture microdissection of plasma cells from subacute sclerosing panencephalitis brain reveals intrathecal disease-relevant antibodies," *PNAS*, 102(20):7245-7250, 2005.
Campbell et al., "Subclonal phylogenetic structures in cancer revealed by ultra-deep sequencing," *PNAS*, 105(35):13081-13086, 2008.
Chapal et al., "Thyroid peroxidase autoantibodies obtained from random single chain Fv libraries contain the same heavy/light chain combinations as occur in vivo," *Endocrinology*, 142(11):4740-4750, 2001.
Cheung et al., "A proteomics approach for the identification and cloning of monoclonal antibodies from serum", *Nature Biotechnology*, 30(5):447-52, 2012.
Clackson et al., "Making antibody fragments using phage display libraries," *Letters to Nature*, 352:624-628, 1991.
Correia-Neves et al., "The shaping of the T cell repertoire," *Immunity*, 14:21-32, 2001.

(Continued)

*Primary Examiner* — Brad Duffy
(74) *Attorney, Agent, or Firm* — Parker Highlander PLLC

(57) ABSTRACT

Methods and compositions for identification of candidate antigen-specific variable regions as well as generation of antibodies or antigen-binding fragments that could have desired antigen specificity are provided. For example, in certain aspects, methods for determining amino acid sequences of serum antibody CDR3 and abundancy levels are described. In some aspects, methods for determining nucleic acid sequences of antibody variable region sequences and the frequency thereof in biological samples are provided. Furthermore, the invention provides methods for identification and generation of antibodies or antigen-binding fragments that comprise highly-represented CDR domains.

12 Claims, 9 Drawing Sheets

Specification includes a Sequence Listing.

(56) References Cited

OTHER PUBLICATIONS

Damoc et al., "High resolution proteome analysis of cryoglobulins using Fourier transform-ion cyclotron resonance mass spectrometry", *Proteomics*, 3:1425-1433, 2003.
De Costa et al., "Sequencing and quantifying IgG fragments and antigen-binding regions by mass spectrometry," *Journal of Proteome Research*, 9:2937-2945, 2010.
DeKosky et al., "High-throughput sequencing of the paired human immunoglobulin heavy and light chain repertoire", *Nature Biotechnology*, 31(2):166-169, 2013.
Dornmair et al., "Novel approaches for identifying target antigens of autoreactive human B and T cells", *Seminars in Immunopathology*, 31(4):467-477, 2009.
Extended European Search Report issued in European Application No. 11784105.6, dated Sep. 11, 2013.
Fischer et al., "Sequencing antibody repertoires: the next generation", *MAbs*, 3(1):17-20, 2011.
Freeman et al., "Profiling the T-cell receptor beta-chain repertoire by massively parallel sequencing," *Genome Research*, 19:1817-1824, 2009.
Glanville et al., "Precise determination of the diversity of a combinatorial antibody library gives insight into the human immunoglobulin repertoire", *Proc Natl Acad Sci USA*, 106(48):20216-20221, 2009.
Huse at al., "Purification of antibodies by affinity chromatography", *J Biochem Biophys Methods*, 51:217-231, 2002.
Instructions for Product Nos. 21901 and 21902, Maleimide-PEG2-Biotin Sulfhydryl-reactive biotin labeling reagent with polyethylene glycol (PEG) spacer arm, published by Thermo Fisher Scientific, Inc., 2008.
Ippolito et al., "Antibody repertoires in humanized NOD-scid-IL2Rγ(null) mice and human B cells reveals human-like diversification and tolerance checkpoints in the mouse", *PLoS One*, 7(4):e35497, 2012.
Kurokawa et al., "Paired cloning of the T cell receptor α and β genes from a single T cell without the establishment of a T cell clone," *Clin Exp Immunol*, 123:340-345, 2001.
Maiolica et al., "Targeted proteome investigation via selected reaction monitoring mass spectrometry", *Journal of Proteomics*, 75(12):3495-3513, 2012.
Matsutani et al., "Restricted usage of T-cell receptor α-chain variable region (TCRAV) and T-cell receptor β-chain variable region (TCRBV) repertoires after human allogeneic haematopoietic transplantation," *British Journal of Haematology*, 109:759-769, 2000.
McMahan et al., "Production, characterization, and immunogenicity of a soluble rat single chain T cell receptor specific for an encephalitogenic peptide," *The Journal of Biological Chemistry*, 278(33):30961-30970, 2003.
Meijer et al., "Isolation of human anitbody repertoires with preservation of the natural heavy and light chain pairing", *J Mol Biol.*, 358: 764-772, 2006.
Meijer et al., "Isolation of human anitbody repertoires with preservation of the natural heavy and light chain pairing", *J Mol Biol.*, 358: 764-772, 2006. [Supplementary Data].
Mouquet et al., "Complex-type N-glycan recognition by potent broadly neutralizing HIV antibodies", *Proc Natl Acad Sci USA*, 109(47):E3268-E3277, 2012.
Nazabal et al., "Immunoassays with direct mass spectrometric detection", *Analytical Chemistry*, 78(11):3562-3570, 2006.
Obermeier et al., "Matching of oligoclonal immunoglobulin transcriptomes and proteomes of cerebrospinal fluid in multiple sclerosis," *Nature Medicine*, 14(6):688-693, 2008.
Office Communication issued in Australian Application No. 2011256290, dated Aug. 27, 2013.
Office Communication European Application No. 12799408.5, dated Feb. 5, 2016.
Omenn et al., "Overview of the HUPO plasma proteome project: results from the pilot phase with 35 collaborating laboratories and multiple analytical groups, generating a core dataset of 3020 proteins and a publicly-available database", *Proteomics*, 5:3226-3245, 2005.
Omenn et al., "Overview of the HUPO plasma proteome project: results from the pilot phase with 35 collaborating laboratories and multiple analytical groups, generating a core dataset of 3020 proteins and a publicly-available database", *Proteomics*, 5:3226-3245, 2005. [Supplementary Materials, Protein dataset].
Packer and Muraro, "Optimized clonotypic analysis of T-cell receptor repertoire in immune reconstitution," *Experimental Hematology*, 35:516-521, 2007.
PCT International Search Report issued in International Application No. PCT/US2011/036852, dated Sep. 26, 2012.
PCT Third Party Observation submitted in International Application No. PCT/US2011/036852 dated Sep. 14, 2012.
PCT International Search Report and Written Opinion issued in International Application No. PCT/US2012/066454, dated Jul. 31, 2013.
Peng, "Protein mixture analysis by tandem mass spectrometry" In: The Bioinformatics of Brains: From Genes and Proteins to Behaviors (Williams RW, ed.), pp. 61-68 (2003), Washington, DC: Society for Neuroscience.
Persson et al., "Generation of diverse high-affinity human monoclonal antibodies by repertoire cloning," *Proc. Natl. Sci. USA*, 88:2432-2436, 1991.
Ravetch et al., "Structure of the human immunoglobulin mu locus: characterization of embryonic and rearranged J and D genes", *Cell*, 27:583-591, 1981.
Reddy et al., "Monoclonal antibodies isolated without screening by analyzing the variable-gene repertoire of plasma cells", *Nature Biotechnology*, 28(9):965-9, 2010.
Sato et al., "Proteomics-directed cloning of circulating antiviral human monoclonal antibodies", *Nature Biotechnology*, 30(11):1039-1043, 2012.
Schluter et al., "Sequence analysis of homogeneous peptides of shark immunoglobulin light chains by tandem mass spectrometry: correlation with gene sequence and homologies among variable and constant region peptides of sharks and mammals," *Molecular Immunology*, 27(1):17-23, 1990.
Weinstein et al., "High-throughput sequencing of the zebrafish antibody repertoire," *Science*, 324:807-810, 2009.
Willis et al., "Rapid molecular cloning of rearrangements of the IGHJ locus using long-distance inverse polymerase chain reaction", *Blood*, 90(6):2456-2464, 1997.
Wine et al., "Molecular deconvolution of the monoclonal antibodies that comprise the polyclonal serum response", *Proc Natl Acad Sci USA*, 110(8):2993-2998, 2013.
Yates, "Mass spectrometry from genomics to proteomics", *Trends Genet.*, 16(1):5-8, 2000.

\* cited by examiner

SEQUENCE LISTING

<160> NUMBER OF SEQ ID NOS: 192

<210> SEQ ID NO 1
<211> LENGTH: 14
<212> TYPE: PRT
<213> ORGANISM: Artificial Sequence
<220> FEATURE:
<223> OTHER INFORMATION: Synthetic peptide

<400> SEQUENCE: 1

Asn Val Ala Gly Tyr Leu Cys Ala Pro Ala Phe Asn Phe Arg
1               5                   10

<210> SEQ ID NO 2
<211> LENGTH: 21
<212> TYPE: PRT
<213> ORGANISM: Artificial Sequence
<220> FEATURE:
<223> OTHER INFORMATION: Synthetic peptide

<400> SEQUENCE: 2

Val Cys Gly Met Asp Leu Trp Gly Pro Gly Thr Leu Val Thr Val Ser
1               5                   10                  15

Ser Gly Gln Pro Lys
            20

<210> SEQ ID NO 3
<211> LENGTH: 18
<212> TYPE: PRT
<213> ORGANISM: Artificial Sequence
<220> FEATURE:
<223> OTHER INFORMATION: Synthetic peptide

<400> SEQUENCE: 3

Glu Thr Gly Gly Gly Leu Val Gln Pro Gly Gly Ser Leu Thr Leu Ser
1               5                   10                  15

Cys Lys

<210> SEQ ID NO 4
<211> LENGTH: 16
<212> TYPE: PRT
<213> ORGANISM: Artificial Sequence
<220> FEATURE:
<223> OTHER INFORMATION: Synthetic peptide

<400> SEQUENCE: 4

Met Thr Ser Leu Thr Ala Ala Asp Thr Ala Thr Tyr Phe Cys Ala Arg
1               5                   10                  15

<210> SEQ ID NO 5
<211> LENGTH: 13
<212> TYPE: PRT
<213> ORGANISM: Artificial Sequence
<220> FEATURE:
<223> OTHER INFORMATION: Synthetic peptide

<400> SEQUENCE: 5

Leu Thr Ala Ala Asp Thr Ala Thr Tyr Phe Cys Ala Arg
1               5                   10

<210> SEQ ID NO 6
<211> LENGTH: 26
<212> TYPE: PRT
<213> ORGANISM: Artificial Sequence
<220> FEATURE:
<223> OTHER INFORMATION: Synthetic peptide

<400> SEQUENCE: 6

Asp Gly Gly Ile Tyr Gly Thr Met Phe Asn Phe Trp Gly Pro Gly Thr
1               5                   10                  15

Leu Val Thr Val Ser Ser Gly Gln Pro Lys
            20                  25

<210> SEQ ID NO 7
<211> LENGTH: 27
<212> TYPE: PRT
<213> ORGANISM: Artificial Sequence
<220> FEATURE:
<223> OTHER INFORMATION: Synthetic peptide

<400> SEQUENCE: 7

Asn Tyr Gly Gly Ala Ala Ser Tyr Gly Met Asp Leu Trp Gly Pro Gly
1               5                   10                  15

Thr Leu Val Thr Val Ser Ser Gly Gln Pro Lys
            20                  25

<210> SEQ ID NO 8
<211> LENGTH: 25
<212> TYPE: PRT
<213> ORGANISM: Artificial Sequence
<220> FEATURE:
<223> OTHER INFORMATION: Synthetic peptide

<400> SEQUENCE: 8

Met Asp Ser His Ser Asp Gly Phe Asp Pro Trp Gly Pro Gly Thr Leu
1               5                   10                  15

Val Ser Val Ser Ser Gly Gln Pro Lys
            20                  25

<210> SEQ ID NO 9
<211> LENGTH: 21
<212> TYPE: PRT
<213> ORGANISM: Artificial Sequence
<220> FEATURE:
<223> OTHER INFORMATION: Synthetic peptide

<400> SEQUENCE: 9

Val Cys Gly Met Asp Leu Trp Gly Pro Gly Thr Leu Val Thr Val Ser
1               5                   10                  15

Ser Gly Gln Pro Lys
            20

<210> SEQ ID NO 10
<211> LENGTH: 26
<212> TYPE: PRT
<213> ORGANISM: Artificial Sequence
<220> FEATURE:
<223> OTHER INFORMATION: Synthetic peptide

<400> SEQUENCE: 10

Asp Gly Gly Ile Tyr Gly Thr Met Phe Asn Phe Trp Gly Pro Gly Thr
1               5                   10                  15

Leu Val Thr Val Ser Ser Gly Gln Pro Lys
            20                  25

<210> SEQ ID NO 11
<211> LENGTH: 14
<212> TYPE: PRT

```
<213> ORGANISM: Artificial Sequence
<220> FEATURE:
<223> OTHER INFORMATION: Synthetic peptide

<400> SEQUENCE: 11

Asn Val Ala Gly Tyr Leu Cys Ala Pro Ala Phe Asn Phe Arg
1               5                   10

<210> SEQ ID NO 12
<211> LENGTH: 19
<212> TYPE: PRT
<213> ORGANISM: Artificial Sequence
<220> FEATURE:
<223> OTHER INFORMATION: Synthetic peptide

<400> SEQUENCE: 12

Asn Phe Lys Leu Trp Gly Pro Gly Thr Leu Val Thr Val Ser Ser Gly
1               5                   10                  15

Gln Pro Lys

<210> SEQ ID NO 13
<211> LENGTH: 19
<212> TYPE: PRT
<213> ORGANISM: Artificial Sequence
<220> FEATURE:
<223> OTHER INFORMATION: Synthetic peptide

<400> SEQUENCE: 13

Asn Phe Gly Leu Trp Gly Pro Gly Thr Leu Val Thr Val Ser Ser Gly
1               5                   10                  15

Gln Pro Lys

<210> SEQ ID NO 14
<211> LENGTH: 11
<212> TYPE: PRT
<213> ORGANISM: Artificial Sequence
<220> FEATURE:
<223> OTHER INFORMATION: Synthetic peptide

<400> SEQUENCE: 14

Glu Leu Thr Gly Asn Gly Ile Tyr Ala Leu Lys
1               5                   10

<210> SEQ ID NO 15
<211> LENGTH: 19
<212> TYPE: PRT
<213> ORGANISM: Artificial Sequence
<220> FEATURE:
<223> OTHER INFORMATION: Synthetic peptide

<400> SEQUENCE: 15

Ala Phe Asn Leu Trp Gly Pro Gly Thr Leu Val Thr Val Ser Ser Gly
1               5                   10                  15

Gln Pro Lys

<210> SEQ ID NO 16
<211> LENGTH: 24
<212> TYPE: PRT
<213> ORGANISM: Artificial Sequence
<220> FEATURE:
<223> OTHER INFORMATION: Synthetic peptide

<400> SEQUENCE: 16

Ser Pro Ser Ser Gly Ser Ser Asn Leu Trp Gly Pro Gly Thr Leu Val
1               5                   10                  15
```

Thr Val Ser Ser Gly Gln Pro Lys
            20

<210> SEQ ID NO 17
<211> LENGTH: 19
<212> TYPE: PRT
<213> ORGANISM: Artificial Sequence
<220> FEATURE:
<223> OTHER INFORMATION: Synthetic peptide

<400> SEQUENCE: 17

Gly Met Asp Leu Trp Gly Pro Gly Thr Leu Val Thr Val Ser Ser Gly
1               5                   10                  15

Gln Pro Lys

<210> SEQ ID NO 18
<211> LENGTH: 24
<212> TYPE: PRT
<213> ORGANISM: Artificial Sequence
<220> FEATURE:
<223> OTHER INFORMATION: Synthetic peptide

<400> SEQUENCE: 18

Gly Ala Gly Trp Val Asp Tyr Ser Leu Trp Gly Pro Gly Thr Leu Val
1               5                   10                  15

Thr Val Ser Ser Gly Gln Pro Lys
            20

<210> SEQ ID NO 19
<211> LENGTH: 21
<212> TYPE: PRT
<213> ORGANISM: Artificial Sequence
<220> FEATURE:
<223> OTHER INFORMATION: Synthetic peptide

<400> SEQUENCE: 19

Tyr Ala Pro Phe Asn Leu Trp Gly Pro Gly Thr Leu Val Thr Val Ser
1               5                   10                  15

Ser Gly Gln Pro Lys
            20

<210> SEQ ID NO 20
<211> LENGTH: 12
<212> TYPE: PRT
<213> ORGANISM: Artificial Sequence
<220> FEATURE:
<223> OTHER INFORMATION: Synthetic peptide

<400> SEQUENCE: 20

Gly Tyr Gly Ser Ser Ser Asp Gly Trp Leu Thr Arg
1               5                   10

<210> SEQ ID NO 21
<211> LENGTH: 19
<212> TYPE: PRT
<213> ORGANISM: Artificial Sequence
<220> FEATURE:
<223> OTHER INFORMATION: Synthetic peptide

<400> SEQUENCE: 21

Ala Phe Thr Leu Trp Gly Pro Gly Thr Leu Val Thr Val Ser Ser Gly
1               5                   10                  15

Gln Pro Lys

```
<210> SEQ ID NO 22
<211> LENGTH: 23
<212> TYPE: PRT
<213> ORGANISM: Artificial Sequence
<220> FEATURE:
<223> OTHER INFORMATION: Synthetic peptide

<400> SEQUENCE: 22

Asn Pro Gly Gly Thr Ser Asn Leu Trp Gly Pro Gly Thr Leu Val Thr
1               5                   10                  15

Val Ser Ser Gly Gln Pro Lys
            20

<210> SEQ ID NO 23
<211> LENGTH: 27
<212> TYPE: PRT
<213> ORGANISM: Artificial Sequence
<220> FEATURE:
<223> OTHER INFORMATION: Synthetic peptide

<400> SEQUENCE: 23

Ala Pro Ala Ala Ser Thr Asn Tyr Gly Tyr Asp Leu Trp Gly Pro Gly
1               5                   10                  15

Thr Leu Val Thr Val Ser Ser Gly Gln Pro Lys
            20                  25

<210> SEQ ID NO 24
<211> LENGTH: 23
<212> TYPE: PRT
<213> ORGANISM: Artificial Sequence
<220> FEATURE:
<223> OTHER INFORMATION: Synthetic peptide

<400> SEQUENCE: 24

Asn Ser Gly Ser Ala Ser Asn Leu Trp Gly Pro Gly Thr Leu Val Thr
1               5                   10                  15

Val Ser Ser Gly Gln Pro Lys
            20

<210> SEQ ID NO 25
<211> LENGTH: 18
<212> TYPE: PRT
<213> ORGANISM: Artificial Sequence
<220> FEATURE:
<223> OTHER INFORMATION: Synthetic peptide

<400> SEQUENCE: 25

Phe Asp Phe Trp Gly Pro Gly Thr Leu Val Thr Val Ser Ser Gly Gln
1               5                   10                  15

Pro Lys

<210> SEQ ID NO 26
<211> LENGTH: 19
<212> TYPE: PRT
<213> ORGANISM: Artificial Sequence
<220> FEATURE:
<223> OTHER INFORMATION: Synthetic peptide

<400> SEQUENCE: 26

Lys Phe Asn Leu Trp Gly Pro Gly Thr Leu Val Thr Val Ser Ser Gly
1               5                   10                  15

Gln Pro Lys
```

<210> SEQ ID NO 27
<211> LENGTH: 27
<212> TYPE: PRT
<213> ORGANISM: Artificial Sequence
<220> FEATURE:
<223> OTHER INFORMATION: Synthetic peptide

<400> SEQUENCE: 27

Asn Tyr Gly Gly Ala Ala Ser Tyr Gly Met Asp Leu Trp Gly Pro Gly
1               5                   10                  15

Thr Leu Val Thr Val Ser Ser Gly Gln Pro Lys
            20                  25

<210> SEQ ID NO 28
<211> LENGTH: 25
<212> TYPE: PRT
<213> ORGANISM: Artificial Sequence
<220> FEATURE:
<223> OTHER INFORMATION: Synthetic peptide

<400> SEQUENCE: 28

Met Asp Ser His Ser Asp Gly Phe Asp Pro Trp Gly Pro Gly Thr Leu
1               5                   10                  15

Val Ser Val Ser Ser Gly Gln Pro Lys
            20                  25

<210> SEQ ID NO 29
<211> LENGTH: 21
<212> TYPE: PRT
<213> ORGANISM: Artificial Sequence
<220> FEATURE:
<223> OTHER INFORMATION: Synthetic peptide

<400> SEQUENCE: 29

Val Cys Gly Met Asp Leu Trp Gly Pro Gly Thr Leu Val Thr Val Ser
1               5                   10                  15

Ser Gly Gln Pro Lys
            20

<210> SEQ ID NO 30
<211> LENGTH: 14
<212> TYPE: PRT
<213> ORGANISM: Artificial Sequence
<220> FEATURE:
<223> OTHER INFORMATION: Synthetic peptide

<400> SEQUENCE: 30

Asn Val Ala Gly Tyr Leu Cys Ala Pro Ala Phe Asn Phe Arg
1               5                   10

<210> SEQ ID NO 31
<211> LENGTH: 19
<212> TYPE: PRT
<213> ORGANISM: Artificial Sequence
<220> FEATURE:
<223> OTHER INFORMATION: Synthetic peptide

<400> SEQUENCE: 31

Asn Phe Lys Leu Trp Gly Pro Gly Thr Leu Val Thr Val Ser Ser Gly
1               5                   10                  15

Gln Pro Lys

<210> SEQ ID NO 32
<211> LENGTH: 11
<212> TYPE: PRT

```
<213> ORGANISM: Artificial Sequence
<220> FEATURE:
<223> OTHER INFORMATION: Synthetic peptide

<400> SEQUENCE: 32

Glu Leu Thr Gly Asn Gly Ile Tyr Ala Leu Lys
1               5                   10

<210> SEQ ID NO 33
<211> LENGTH: 19
<212> TYPE: PRT
<213> ORGANISM: Artificial Sequence
<220> FEATURE:
<223> OTHER INFORMATION: Synthetic peptide

<400> SEQUENCE: 33

Ala Phe Asn Leu Trp Gly Pro Gly Thr Leu Val Thr Val Ser Ser Gly
1               5                   10                  15

Gln Pro Lys

<210> SEQ ID NO 34
<211> LENGTH: 24
<212> TYPE: PRT
<213> ORGANISM: Artificial Sequence
<220> FEATURE:
<223> OTHER INFORMATION: Synthetic peptide

<400> SEQUENCE: 34

Ser Pro Ser Ser Gly Ser Ser Asn Leu Trp Gly Pro Gly Thr Leu Val
1               5                   10                  15

Thr Val Ser Ser Gly Gln Pro Lys
            20

<210> SEQ ID NO 35
<211> LENGTH: 19
<212> TYPE: PRT
<213> ORGANISM: Artificial Sequence
<220> FEATURE:
<223> OTHER INFORMATION: Synthetic peptide

<400> SEQUENCE: 35

Gly Met Asp Leu Trp Gly Pro Gly Thr Leu Val Thr Val Ser Ser Gly
1               5                   10                  15

Gln Pro Lys

<210> SEQ ID NO 36
<211> LENGTH: 24
<212> TYPE: PRT
<213> ORGANISM: Artificial Sequence
<220> FEATURE:
<223> OTHER INFORMATION: Synthetic peptide

<400> SEQUENCE: 36

Gly Ala Gly Trp Val Asp Tyr Ser Leu Trp Gly Pro Gly Thr Leu Val
1               5                   10                  15

Thr Val Ser Ser Gly Gln Pro Lys
            20

<210> SEQ ID NO 37
<211> LENGTH: 12
<212> TYPE: PRT
<213> ORGANISM: Artificial Sequence
<220> FEATURE:
<223> OTHER INFORMATION: Synthetic peptide
```

```
<400> SEQUENCE: 37

Gly Tyr Gly Ser Ser Asp Gly Trp Leu Thr Arg
1               5                   10

<210> SEQ ID NO 38
<211> LENGTH: 23
<212> TYPE: PRT
<213> ORGANISM: Artificial Sequence
<220> FEATURE:
<223> OTHER INFORMATION: Synthetic peptide

<400> SEQUENCE: 38

Asn Pro Gly Gly Thr Ser Asn Leu Trp Gly Pro Gly Thr Leu Val Thr
1               5                   10                  15

Val Ser Ser Gly Gln Pro Lys
            20

<210> SEQ ID NO 39
<211> LENGTH: 27
<212> TYPE: PRT
<213> ORGANISM: Artificial Sequence
<220> FEATURE:
<223> OTHER INFORMATION: Synthetic peptide

<400> SEQUENCE: 39

Ala Pro Ala Ala Ser Thr Asn Tyr Gly Tyr Asp Leu Trp Gly Pro Gly
1               5                   10                  15

Thr Leu Val Thr Val Ser Ser Gly Gln Pro Lys
            20                  25

<210> SEQ ID NO 40
<211> LENGTH: 23
<212> TYPE: PRT
<213> ORGANISM: Artificial Sequence
<220> FEATURE:
<223> OTHER INFORMATION: Synthetic peptide

<400> SEQUENCE: 40

Asn Ser Gly Ser Ala Ser Asn Leu Trp Gly Pro Gly Thr Leu Val Thr
1               5                   10                  15

Val Ser Ser Gly Gln Pro Lys
            20

<210> SEQ ID NO 41
<211> LENGTH: 18
<212> TYPE: PRT
<213> ORGANISM: Artificial Sequence
<220> FEATURE:
<223> OTHER INFORMATION: Synthetic peptide

<400> SEQUENCE: 41

Phe Asp Phe Trp Gly Pro Gly Thr Leu Val Thr Val Ser Ser Gly Gln
1               5                   10                  15

Pro Lys

<210> SEQ ID NO 42
<211> LENGTH: 19
<212> TYPE: PRT
<213> ORGANISM: Artificial Sequence
<220> FEATURE:
<223> OTHER INFORMATION: Synthetic peptide

<400> SEQUENCE: 42

Lys Phe Asn Leu Trp Gly Pro Gly Thr Leu Val Thr Val Ser Ser Gly
```

```
1               5                   10                  15

Gln Pro Lys

<210> SEQ ID NO 43
<211> LENGTH: 24
<212> TYPE: PRT
<213> ORGANISM: Artificial Sequence
<220> FEATURE:
<223> OTHER INFORMATION: Synthetic peptide

<400> SEQUENCE: 43

Ser Asp Glu Ile Asn Asp Tyr Asn Leu Trp Gly Pro Gly Thr Leu Val
1               5                   10                  15

Thr Val Ser Ser Gly Gln Pro Lys
            20

<210> SEQ ID NO 44
<211> LENGTH: 19
<212> TYPE: PRT
<213> ORGANISM: Artificial Sequence
<220> FEATURE:
<223> OTHER INFORMATION: Synthetic peptide

<400> SEQUENCE: 44

Ala Phe Thr Leu Trp Gly Pro Gly Thr Leu Val Thr Val Ser Ser Gly
1               5                   10                  15

Gln Pro Lys

<210> SEQ ID NO 45
<211> LENGTH: 19
<212> TYPE: PRT
<213> ORGANISM: Artificial Sequence
<220> FEATURE:
<223> OTHER INFORMATION: Synthetic peptide

<400> SEQUENCE: 45

Asn Phe Gly Leu Trp Gly Pro Gly Thr Leu Val Thr Val Ser Ser Gly
1               5                   10                  15

Gln Pro Lys

<210> SEQ ID NO 46
<211> LENGTH: 23
<212> TYPE: PRT
<213> ORGANISM: Artificial Sequence
<220> FEATURE:
<223> OTHER INFORMATION: Synthetic peptide

<400> SEQUENCE: 46

Asn Ala Gly Thr Ala Ser Asn Leu Trp Gly Pro Gly Thr Leu Val Thr
1               5                   10                  15

Val Ser Ser Gly Gln Pro Lys
            20

<210> SEQ ID NO 47
<211> LENGTH: 19
<212> TYPE: PRT
<213> ORGANISM: Artificial Sequence
<220> FEATURE:
<223> OTHER INFORMATION: Synthetic peptide

<400> SEQUENCE: 47

Asn Trp Gly Leu Trp Gly Pro Gly Thr Leu Val Thr Val Ser Ser Gly
1               5                   10                  15
```

Gln Pro Lys

<210> SEQ ID NO 48
<211> LENGTH: 26
<212> TYPE: PRT
<213> ORGANISM: Artificial Sequence
<220> FEATURE:
<223> OTHER INFORMATION: Synthetic peptide

<400> SEQUENCE: 48

Asp Ala Gly Asp Ala Gly Tyr His Leu Thr Leu Trp Gly Pro Gly Thr
1               5                   10                  15

Leu Val Thr Val Ser Ser Gly Gln Pro Lys
            20                  25

<210> SEQ ID NO 49
<211> LENGTH: 26
<212> TYPE: PRT
<213> ORGANISM: Artificial Sequence
<220> FEATURE:
<223> OTHER INFORMATION: Synthetic peptide

<400> SEQUENCE: 49

Thr Asp Ser Ser Asp His Thr Tyr Phe Ile Leu Trp Gly Pro Gly Thr
1               5                   10                  15

Leu Val Thr Val Ser Ser Gly Gln Pro Lys
            20                  25

<210> SEQ ID NO 50
<211> LENGTH: 28
<212> TYPE: PRT
<213> ORGANISM: Artificial Sequence
<220> FEATURE:
<223> OTHER INFORMATION: Synthetic peptide

<400> SEQUENCE: 50

Ala Ala Gly Tyr Gly Ala Asp Ala Tyr Ala Trp Asn Leu Trp Gly Pro
1               5                   10                  15

Gly Thr Leu Val Thr Val Ser Ser Gly Gln Pro Lys
            20                  25

<210> SEQ ID NO 51
<211> LENGTH: 14
<212> TYPE: PRT
<213> ORGANISM: Artificial Sequence
<220> FEATURE:
<223> OTHER INFORMATION: Synthetic peptide

<400> SEQUENCE: 51

Asn Val Ala Gly Tyr Leu Cys Ala Pro Ala Phe Asn Phe Arg
1               5                   10

<210> SEQ ID NO 52
<211> LENGTH: 414
<212> TYPE: DNA
<213> ORGANISM: Artificial Sequence
<220> FEATURE:
<223> OTHER INFORMATION: Synthetic primer

<400> SEQUENCE: 52
atggcccagc cggccatggc gcaggaacag ctggaagaat ctggtgacct ggttaaaccg      60
ggtgcttctc tgaccctgac ctgcaccgct tctggtttct ctttctcttc ttcttactac     120
atggcttggg ttcgtcaggc tccgggtaaa ggtctggaat ggatcggttg catgaactct     180

```
ggtggtgaca ccgcttacgc ttcttgggct aaaggtcgtt tctctatctc taaaacctct    240
tctaccacca tgaccctgca gctgacctct ctgaccgctg ctgacaccgc tacctacttc    300
tgcgctcgta acgttgctgg ttacctgtgc gctccggctt tcaacttccg ttctccgggt    360
accctggtta ccgtttcttc tggtggtggc ggtagcggtg gtggtggtag cggt          414
```

<210> SEQ ID NO 53
<211> LENGTH: 25
<212> TYPE: PRT
<213> ORGANISM: Artificial Sequence
<220> FEATURE:
<223> OTHER INFORMATION: Synthetic peptide

<400> SEQUENCE: 53

```
Met Asp Ser His Ser Asp Gly Phe Asp Pro Trp Gly Pro Gly Thr Leu
1               5                   10                  15

Val Ser Val Ser Ser Gly Gln Pro Lys
            20                  25
```

<210> SEQ ID NO 54
<211> LENGTH: 411
<212> TYPE: DNA
<213> ORGANISM: Artificial Sequence
<220> FEATURE:
<223> OTHER INFORMATION: Synthetic primer

<400> SEQUENCE: 54

```
atggcccagc cggccatggc gcaggaacag ctggaagaat ctggtggtga cctggttaaa     60
ccggaaggtt ctctgaccct gacctgcacc gcttctggtt tctctttctc ttcttcttac    120
tggatctggt gggttcgtca ggctccgggt aaaggtctgg aatggatcgc ttgcatctac    180
accggttctg gtaccaccta ctacgctaac tgggctaaag tcgtttcac catctctaaa     240 acctcttcta ccaccgttac cctgcagatg acctctctga ccgctgctga caccgctacc    300
tacttctgcg ctcgtatgga ctctcactct gacggtttcg acccgtgggg tccgggtacc    360
ctggtttctg tttcttctgg tggtggcggt agcggtggtg gtggtagcgg t             411
```

<210> SEQ ID NO 55
<211> LENGTH: 19
<212> TYPE: PRT
<213> ORGANISM: Artificial Sequence
<220> FEATURE:
<223> OTHER INFORMATION: Synthetic peptide

<400> SEQUENCE: 55

```
Asn Phe Lys Leu Trp Gly Pro Gly Thr Leu Val Thr Val Ser Ser Gly
1               5                   10                  15

Gln Pro Lys
```

<210> SEQ ID NO 56
<211> LENGTH: 387
<212> TYPE: DNA
<213> ORGANISM: Artificial Sequence
<220> FEATURE:
<223> OTHER INFORMATION: Synthetic primer

<400> SEQUENCE: 56

```
atggcccagc cggccatggc gcagtctctg gaagaatctg gtggtggtct ggttaaaccg     60
ggtggtaccc tgaccctgac ctgcaccgct tctggtttcg acttctcttc taacccgatc    120
aactgggttc gtcaggctcc gggtaaaggt ccggaatgga tcggttacat caacaacggt    180
```

```
aactctaaaa cctactacgc ttcttgggct aaaggtcgtt tcaccatctc taaaacctct    240
tctaccaccg ttaccctgca gatgacctct ctgaccgctg ctgacaccgc tacctacttc    300
tgcgctcgta acttcaaact gtggggtccg ggtaccctgg ttaccgtttc ttctggtggt    360
ggcggtagcg gtggtggtgg tagcggt                                        387
```

<210> SEQ ID NO 57
<211> LENGTH: 21
<212> TYPE: PRT
<213> ORGANISM: Artificial Sequence
<220> FEATURE:
<223> OTHER INFORMATION: Synthetic peptide

<400> SEQUENCE: 57

Val Cys Gly Met Asp Leu Trp Gly Pro Gly Thr Leu Val Thr Val Ser
1               5                   10                  15

Ser Gly Gln Pro Lys
            20

<210> SEQ ID NO 58
<211> LENGTH: 414
<212> TYPE: DNA
<213> ORGANISM: Artificial Sequence
<220> FEATURE:
<223> OTHER INFORMATION: Synthetic primer

<400> SEQUENCE: 58

```
atggcccagc cggccatggc gcagtctctg gaagaatctg gtgacctggt taaaccgggt     60
gcttctctga ccctgacctg caccgcttct ggtttctctt tctcttctgg ttactacatg    120
tgctgggttc gtcaggctcc gggtaaaggt ctggaactga tcgcttgcat ctacgctacc    180
acctctgcta cctactacgc ttcttgggct aaaggtcgtt tcaccatctc tcagacctct    240
tctaccaccg ttaccctgca gatgacctct ctgaccgctg ctgacaccgc tacctacttc    300
tgcgctcgta acgtttacgg tgcttctcgt gtttgcggta tggacctgtg ggtccgggt    360 accctggtta ccgtttcttc tggtggtggc ggtagcggtg gtggtggtag cggt          414
```

<210> SEQ ID NO 59
<211> LENGTH: 23
<212> TYPE: PRT
<213> ORGANISM: Artificial Sequence
<220> FEATURE:
<223> OTHER INFORMATION: Synthetic peptide

<400> SEQUENCE: 59

Asn Pro Gly Gly Thr Ser Asn Leu Trp Gly Pro Gly Thr Leu Val Thr
1               5                   10                  15

Val Ser Ser Gly Gln Pro Lys
            20

<210> SEQ ID NO 60
<211> LENGTH: 402
<212> TYPE: DNA
<213> ORGANISM: Artificial Sequence
<220> FEATURE:
<223> OTHER INFORMATION: Synthetic primer

<400> SEQUENCE: 60

```
atggcccagc cggccatggc gcagtctctg gaagaatctg gtgacctggt taaaccgggt     60
tcttctctga ccctgacctg caccggttct ggtttctctt tctctaacaa atactggatc    120
tgctgggttc gtcaggctcc gggtaaaggt ctggaatgga tcgcttgcat ctacatcggt    180
```

```
aacatcgaca acaccgacta cgcttcttgg gctaaaggtc gtttcaccat ctcttctacc    240
tcttctacca ccgttaccct gcagatgacc tctctgaccg ctgctgacac cgctacctac    300
ttctgcgctc gtaacccggg tggtacctct aacctgtggg gtccgggtac cctggttacc    360
gtttcttctg gtggtggcgg tagcggtggt ggtggtagcg gt                       402
```

<210> SEQ ID NO 61
<211> LENGTH: 24
<212> TYPE: PRT
<213> ORGANISM: Artificial Sequence
<220> FEATURE:
<223> OTHER INFORMATION: Synthetic peptide

<400> SEQUENCE: 61

```
Ser Pro Ser Ser Gly Ser Ser Asn Leu Trp Gly Pro Gly Thr Leu Val
1               5                   10                  15

Thr Val Ser Ser Gly Gln Pro Lys
            20
```

<210> SEQ ID NO 62
<211> LENGTH: 402
<212> TYPE: DNA
<213> ORGANISM: Artificial Sequence
<220> FEATURE:
<223> OTHER INFORMATION: Synthetic primer

<400> SEQUENCE: 62

```
atggcccagc cggccatggc gcagcagctg gaagaatctg gtgacctggt taaaccgggt    60
ggtaccctga ccctgtcttg caccgcttct ggtttctctt tctcttcttc ttactacatg    120
tgctgggttc gtcaggctcc gggtaaaggt ctggaatgga tcgcttgcat ctacaccggt    180
tctggttcta ccaactacgc ttcttgggct aaaggtcgtt tcaccatctc taaatcttct    240
tctaccaccg ttaccctgca gatgacctct gaccgctg ctgacaccgc tacctacttc    300
tgcgctcgtt ctccgtcttc tggttcttct aacctgtggg gtccgggtac cctggttacc    360
gtttcttctg gtggtggcgg tagcggtggt ggtggtagcg gt                       402
```

<210> SEQ ID NO 63
<211> LENGTH: 19
<212> TYPE: PRT
<213> ORGANISM: Artificial Sequence
<220> FEATURE:
<223> OTHER INFORMATION: Synthetic peptide

<400> SEQUENCE: 63

```
Gly Met Asp Leu Trp Gly Pro Gly Thr Leu Val Thr Val Ser Ser Gly
1               5                   10                  15

Gln Pro Lys
```

<210> SEQ ID NO 64
<211> LENGTH: 429
<212> TYPE: DNA
<213> ORGANISM: Artificial Sequence
<220> FEATURE:
<223> OTHER INFORMATION: Synthetic primer

<400> SEQUENCE: 64

```
atggcccagc cggccatggc gcaggaacag ctggaagaat ctggtggtct ggttcagccg    60
gaaggttctc tgaccctgac ctgcaccgct tctggtttct ctttcaccgt tggttacgac    120
atgtgctggg ttcgtcaggc tccgggtaaa ggtctggaat ggatcggttg catcccgtct    180
```

```
gctgacacca cctactacgc ttcttgggct aaaggtcgtt tcaccatctc taaaacctct    240
tctacctctg ttaccctgca gatgacccgt ctgaccgttg ctgacaccgc tacctacttc    300
tgcgctcgtg aagacaccta cggtgacgct aacaccgact acctgtaccg tggtatggac    360
ctgtggggtc cgggtaccct ggttaccgtt tcttctggtg gtggcggtag cggtggtggt    420
ggtagcggt                                                            429
```

```
<210> SEQ ID NO 65
<211> LENGTH: 46
<212> TYPE: DNA
<213> ORGANISM: Artificial Sequence
<220> FEATURE:
<223> OTHER INFORMATION: Synthetic primer

<400> SEQUENCE: 65
gatgacgatg cggcccccga ggccttgatt tcyacmttgg tgccag                   46
```

```
<210> SEQ ID NO 66
<211> LENGTH: 46
<212> TYPE: DNA
<213> ORGANISM: Artificial Sequence
<220> FEATURE:
<223> OTHER INFORMATION: Synthetic primer

<400> SEQUENCE: 66
gatgacgatg cggcccccga ggcctygacs accacctcgg tccctc                   46
```

```
<210> SEQ ID NO 67
<211> LENGTH: 52
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (33)..(34)
<223> OTHER INFORMATION: n is a, c, g, or t

<400> SEQUENCE: 67
ggtggtggtg gtagcggtgg tggtggcagc gmnnhhgwdm tgacccagac ts            52
```

```
<210> SEQ ID NO 68
<211> LENGTH: 32
<212> TYPE: DNA
<213> ORGANISM: Artificial Sequence
<220> FEATURE:
<223> OTHER INFORMATION: Synthetic primer

<400> SEQUENCE: 68
ggcccagccg gccatggctc agcagctgga ag                                  32
```

```
<210> SEQ ID NO 69
<211> LENGTH: 31
<212> TYPE: DNA
<213> ORGANISM: Artificial Sequence
<220> FEATURE:
<223> OTHER INFORMATION: Synthetic primer

<400> SEQUENCE: 69
ggcccagccg gccatggctc aggaacagct g                                   31
```

```
<210> SEQ ID NO 70
<211> LENGTH: 32
<212> TYPE: DNA
```

```
<213> ORGANISM: Artificial Sequence
<220> FEATURE:
<223> OTHER INFORMATION: Synthetic primer

<400> SEQUENCE: 70
ggcccagccg gccatggctc agtctctgga ag                                    32

<210> SEQ ID NO 71
<211> LENGTH: 21
<212> TYPE: DNA
<213> ORGANISM: Artificial Sequence
<220> FEATURE:
<223> OTHER INFORMATION: Synthetic primer

<400> SEQUENCE: 71
gatgacgatg cggcccccga g                                                21

<210> SEQ ID NO 72
<211> LENGTH: 239
<212> TYPE: PRT
<213> ORGANISM: Artificial Sequence
<220> FEATURE:
<223> OTHER INFORMATION: Synthetic peptide

<400> SEQUENCE: 72
```

Gln Glu Gln Leu Glu Glu Ser Gly Asp Leu Val Lys Pro Gly Ala Ser
1               5                   10                  15

Leu Thr Leu Thr Cys Thr Ala Ser Gly Phe Ser Phe Ser Ser Ser Tyr
            20                  25                  30

Tyr Met Ala Trp Val Arg Gln Ala Pro Gly Lys Gly Leu Glu Trp Ile
        35                  40                  45

Gly Cys Met Asn Ser Gly Gly Asp Thr Ala Tyr Ala Ser Trp Ala Lys
    50                  55                  60

Gly Arg Phe Ser Ile Ser Lys Thr Ser Ser Thr Met Thr Leu Gln
65                  70                  75                  80

Leu Thr Ser Leu Thr Ala Ala Asp Thr Ala Thr Tyr Phe Cys Ala Arg
                85                  90                  95

Asn Val Ala Gly Tyr Leu Cys Ala Pro Ala Phe Asn Phe Arg Ser Pro
            100                 105                 110

Gly Thr Leu Val Thr Val Ser Ser Gly Gly Ser Gly Gly Gly Ser
        115                 120                 125

Ala Asp Val Met Thr Gln Thr Pro Ser Ser Val Thr Ala Ala Val Gly
    130                 135                 140

Gly Thr Val Ser Ile Ser Cys Arg Ser Ser Lys Ser Val Tyr Asn Asn
145                 150                 155                 160

Asn Trp Leu Ser Trp Tyr Gln Gln Lys Pro Gly Gln Pro Lys Leu
                165                 170                 175

Leu Ile Tyr Glu Thr Ser Lys Leu Pro Ser Gly Val Pro Ser Arg Phe
            180                 185                 190

Ser Gly Ser Gly Ser Gly Thr Gln Phe Thr Leu Thr Ile Ser Asp Leu
        195                 200                 205

Glu Cys Asp Asp Ala Ala Thr Tyr Tyr Cys Ala Gly Gly Tyr Arg Ser
    210                 215                 220

Ser Ser Asp Asn Gly Phe Gly Gly Gly Thr Glu Val Val Val Lys
225                 230                 235

```
<210> SEQ ID NO 73
<211> LENGTH: 239
<212> TYPE: PRT
```

<213> ORGANISM: Artificial Sequence
<220> FEATURE:
<223> OTHER INFORMATION: Synthetic peptide

<400> SEQUENCE: 73

Gln Glu Gln Leu Glu Glu Ser Gly Gly Asp Leu Val Lys Pro Glu Gly
1               5                   10                  15

Ser Leu Thr Leu Thr Cys Thr Ala Ser Gly Phe Ser Phe Ser Ser Ser
            20                  25                  30

Tyr Trp Ile Trp Trp Val Arg Gln Ala Pro Gly Lys Gly Leu Glu Trp
        35                  40                  45

Ile Ala Cys Ile Tyr Thr Gly Ser Gly Thr Thr Tyr Tyr Ala Asn Trp
50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Met Asp Ser His Ser Asp Gly Phe Asp Pro Trp Gly Pro Gly
            100                 105                 110

Thr Leu Val Ser Val Ser Ser Gly Gly Gly Ser Gly Gly Gly Gly
        115                 120                 125

Ser Gly Val Glu Leu Thr Gln Thr Pro Ala Ser Val Ser Glu Pro Val
130                 135                 140

Gly Gly Thr Val Thr Ile Lys Cys Gln Ala Ser Gln Asn Ile Tyr Ser
145                 150                 155                 160

Asp Leu Ala Trp Tyr Gln Gln Lys Pro Gly Gln Pro Pro Lys Arg Leu
                165                 170                 175

Ile Tyr Asp Ala Ser Lys Leu Pro Ser Gly Val Pro Ser Arg Phe Lys
            180                 185                 190

Gly Ser Gly Ser Gly Thr Glu Tyr Thr Leu Thr Ile Ser Asp Leu Glu
        195                 200                 205

Cys Ala Asp Ala Ala Thr Tyr Tyr Cys Gln Thr Tyr His Asp Phe Asp
    210                 215                 220

Val Tyr Gly Val Ala Phe Gly Gly Gly Thr Glu Val Val Val Glu
225                 230                 235

<210> SEQ ID NO 74
<211> LENGTH: 241
<212> TYPE: PRT
<213> ORGANISM: Artificial Sequence
<220> FEATURE:
<223> OTHER INFORMATION: Synthetic peptide

<400> SEQUENCE: 74

Gln Ser Leu Glu Glu Ser Gly Asp Leu Val Lys Pro Gly Ser Ser Leu
1               5                   10                  15

Thr Leu Thr Cys Thr Gly Ser Gly Phe Ser Phe Ser Asn Lys Tyr Trp
            20                  25                  30

Ile Cys Trp Val Arg Gln Ala Pro Gly Lys Gly Leu Glu Trp Ile Gly
        35                  40                  45

Cys Ile Tyr Ile Gly Asn Ile Asp Asn Thr Asp Tyr Ala Ser Trp Ala
50                  55                  60

Lys Gly Arg Phe Thr Ile Ser Ser Thr Ser Thr Thr Val Thr Leu
65                  70                  75                  80

Gln Met Thr Ser Leu Thr Ala Ala Asp Thr Ala Thr Tyr Phe Cys Ala
                85                  90                  95

```
Arg Asn Pro Gly Gly Thr Ser Asn Leu Trp Gly Pro Gly Thr Leu Val
                100                 105                 110

Thr Val Ser Ser Gly Gly Gly Gly Ser Gly Gly Gly Ser Gly Gly Ala
            115                 120                 125

Ile Val Leu Thr Gln Thr Pro Ser Ser Val Glu Ala Ala Val Gly Gly
        130                 135                 140

Thr Val Thr Ile Lys Cys Gln Ala Ser Gln Ser Ile Gly Ser Ile Leu
145                 150                 155                 160

Ala Trp Tyr Gln Gln Lys Pro Gly Gln Arg Pro Lys Leu Leu Ile Tyr
                165                 170                 175

Tyr Ala Ser Thr Leu Ala Ser Gly Val Pro Ser Arg Phe Lys Gly Ser
            180                 185                 190

Gly Ser Gly Thr Gln Phe Ile Leu Thr Ile Ser Asp Leu Glu Cys Ala
        195                 200                 205

Asp Ala Ala Thr Tyr Tyr Cys Gln Ser Tyr Gly Tyr Ser Ser Ser Gly
    210                 215                 220

Ser Tyr Gly Tyr Arg Asn Ala Phe Gly Gly Gly Thr Glu Val Val Val
225                 230                 235                 240

Glu

<210> SEQ ID NO 75
<211> LENGTH: 241
<212> TYPE: PRT
<213> ORGANISM: Artificial Sequence
<220> FEATURE:
<223> OTHER INFORMATION: Synthetic peptide

<400> SEQUENCE: 75

Gln Ser Leu Glu Glu Ser Gly Asp Leu Val Lys Pro Gly Ser Ser Leu
1               5                   10                  15

Thr Leu Thr Cys Thr Gly Ser Gly Phe Ser Phe Ser Asn Lys Tyr Trp
            20                  25                  30

Ile Cys Trp Val Arg Gln Ala Pro Gly Lys Gly Leu Glu Trp Ile Gly
        35                  40                  45

Cys Ile Tyr Ile Gly Asn Ile Asp Asn Thr Asp Tyr Ala Ser Trp Ala
    50                  55                  60

Lys Gly Arg Phe Thr Ile Ser Ser Thr Ser Thr Thr Val Thr Leu
65                  70                  75                  80

Gln Met Thr Ser Leu Thr Ala Ala Asp Thr Ala Thr Tyr Phe Cys Ala
                85                  90                  95

Arg Asn Pro Gly Gly Thr Ser Asn Leu Trp Gly Pro Gly Thr Leu Val
            100                 105                 110

Thr Val Ser Ser Gly Gly Gly Gly Ser Gly Gly Gly Ser Gly Gly Asp
        115                 120                 125

Val Val Met Thr Gln Thr Pro Ser Ser Val Glu Ala Ala Val Gly Gly
    130                 135                 140

Thr Val Thr Ile Lys Cys Gln Ala Ser Gln Ser Ile Gly Asn Val Leu
145                 150                 155                 160

Ala Trp Tyr Gln Gln Lys Pro Gly Gln Arg Pro Lys Leu Leu Ile Tyr
                165                 170                 175

Leu Ala Ser Thr Leu Ala Ser Gly Val Pro Ser Arg Phe Lys Gly Ser
            180                 185                 190

Gly Ser Gly Thr Gln Phe Ile Leu Thr Ile Ser Asp Leu Glu Cys Ala
        195                 200                 205

Asp Ala Ala Thr Tyr Tyr Cys Gln Ser Tyr Gly Tyr Ser Ser Ser Ser
```

Ser Tyr Gly Tyr Arg Asn Ala Phe Gly Gly Thr Glu Val Val Val
225                 230                 235                 240

Lys

<210> SEQ ID NO 76
<211> LENGTH: 237
<212> TYPE: PRT
<213> ORGANISM: Artificial Sequence
<220> FEATURE:
<223> OTHER INFORMATION: Synthetic peptide

<400> SEQUENCE: 76

Gln Gln Leu Glu Glu Ser Gly Asp Leu Val Lys Pro Gly Gly Thr Leu
1               5                   10                  15

Thr Leu Ser Cys Thr Ala Ser Gly Phe Ser Phe Ser Ser Ser Tyr Tyr
                20                  25                  30

Met Cys Trp Val Arg Gln Ala Pro Gly Lys Gly Leu Glu Trp Ile Ala
            35                  40                  45

Cys Ile Tyr Thr Gly Ser Gly Ser Thr Asn Tyr Ala Ser Trp Ala Lys
        50                  55                  60

Gly Arg Phe Thr Ile Ser Lys Ser Ser Ser Thr Val Thr Leu Gln
65                  70                  75                  80

Met Thr Ser Leu Thr Ala Ala Asp Thr Ala Thr Tyr Phe Cys Ala Arg
                85                  90                  95

Ser Pro Ser Ser Gly Ser Ser Asn Leu Trp Gly Pro Gly Thr Leu Val
                100                 105                 110

Thr Val Ser Ser Gly Gly Gly Gly Ser Gly Gly Gly Ser Gly Asp
            115                 120                 125

Val Met Thr Gln Thr Pro Ala Ser Val Ser Ala Ala Val Gly Gly Thr
            130                 135                 140

Val Thr Ile Lys Cys Gln Ala Ser Gln Ser Ile Ser Asn Tyr Leu Ser
145                 150                 155                 160

Trp Tyr Gln Gln Lys Pro Gly Gln Arg Pro Lys Leu Leu Ile Asp Ala
                165                 170                 175

Ala Ser Thr Leu Ala Ser Gly Val Pro Ser Arg Phe Lys Gly Ser Gly
                180                 185                 190

Ser Gly Thr Glu Ser Thr Leu Thr Ile Ser Asp Leu Glu Cys Ala Asp
            195                 200                 205

Ala Ala Thr Tyr Tyr Cys Leu Tyr Gly Tyr Tyr Gly Val Ser Ser Thr
        210                 215                 220

Ser Val Ala Phe Gly Gly Gly Thr Glu Val Val Val Glu
225                 230                 235

<210> SEQ ID NO 77
<211> LENGTH: 8
<212> TYPE: PRT
<213> ORGANISM: Artificial Sequence
<220> FEATURE:
<223> OTHER INFORMATION: Synthetic peptide

<400> SEQUENCE: 77

Gly Thr Leu Val Thr Val Ser Ser
1               5

<210> SEQ ID NO 78
<211> LENGTH: 8
<212> TYPE: PRT

```
<213> ORGANISM: Artificial Sequence
<220> FEATURE:
<223> OTHER INFORMATION: Synthetic peptide

<400> SEQUENCE: 78

Gly Thr Met Val Thr Val Ser Ser
1               5

<210> SEQ ID NO 79
<211> LENGTH: 8
<212> TYPE: PRT
<213> ORGANISM: Artificial Sequence
<220> FEATURE:
<223> OTHER INFORMATION: Synthetic peptide

<400> SEQUENCE: 79

Gly Thr Thr Val Thr Val Ser Ser
1               5

<210> SEQ ID NO 80
<211> LENGTH: 8
<212> TYPE: PRT
<213> ORGANISM: Artificial Sequence
<220> FEATURE:
<223> OTHER INFORMATION: Synthetic peptide

<400> SEQUENCE: 80

Gly Thr Leu Val Thr Ile Ser Ser
1               5

<210> SEQ ID NO 81
<211> LENGTH: 8
<212> TYPE: PRT
<213> ORGANISM: Artificial Sequence
<220> FEATURE:
<223> OTHER INFORMATION: Synthetic peptide

<400> SEQUENCE: 81

Gly Thr Thr Leu Thr Val Ser Ser
1               5

<210> SEQ ID NO 82
<211> LENGTH: 8
<212> TYPE: PRT
<213> ORGANISM: Artificial Sequence
<220> FEATURE:
<223> OTHER INFORMATION: Synthetic peptide

<400> SEQUENCE: 82

Gly Thr Leu Val Thr Val Ser Ala
1               5

<210> SEQ ID NO 83
<211> LENGTH: 8
<212> TYPE: PRT
<213> ORGANISM: Artificial Sequence
<220> FEATURE:
<223> OTHER INFORMATION: Synthetic peptide

<400> SEQUENCE: 83

Gly Thr Ser Val Thr Val Ser Ser
1               5

<210> SEQ ID NO 84
<211> LENGTH: 8
<212> TYPE: PRT
<213> ORGANISM: Artificial Sequence
```

```
<220> FEATURE:
<223> OTHER INFORMATION: Synthetic peptide

<400> SEQUENCE: 84

Gly Thr Glu Val Ile Val Ser Ser
1               5

<210> SEQ ID NO 85
<211> LENGTH: 4
<212> TYPE: PRT
<213> ORGANISM: Artificial Sequence
<220> FEATURE:
<223> OTHER INFORMATION: Synthetic peptide

<400> SEQUENCE: 85

Ala Ser Thr Lys
1

<210> SEQ ID NO 86
<211> LENGTH: 4
<212> TYPE: PRT
<213> ORGANISM: Artificial Sequence
<220> FEATURE:
<223> OTHER INFORMATION: Synthetic peptide

<400> SEQUENCE: 86

Gly Gln Pro Lys
1

<210> SEQ ID NO 87
<211> LENGTH: 4
<212> TYPE: PRT
<213> ORGANISM: Artificial Sequence
<220> FEATURE:
<223> OTHER INFORMATION: Synthetic peptide

<400> SEQUENCE: 87

Ala Gly Pro Thr
1

<210> SEQ ID NO 88
<211> LENGTH: 14
<212> TYPE: PRT
<213> ORGANISM: Artificial Sequence
<220> FEATURE:
<223> OTHER INFORMATION: Synthetic peptide

<400> SEQUENCE: 88

Cys Gly Gly Thr Leu Val Thr Val Ser Ser Gly Gln Pro Lys
1               5                   10

<210> SEQ ID NO 89
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 89

Trp Gly Xaa Gly Thr Leu Val Thr Ser Ser Gly Gln Pro Lys
1               5                   10

<210> SEQ ID NO 90
```

```
<211> LENGTH: 23
<212> TYPE: DNA
<213> ORGANISM: Artificial
<220> FEATURE:
<223> OTHER INFORMATION: synthetic primer

<400> SEQUENCE: 90
caggtccagc tkgtrcagtc tgg                                               23

<210> SEQ ID NO 91
<211> LENGTH: 23
<212> TYPE: DNA
<213> ORGANISM: Artificial
<220> FEATURE:
<223> OTHER INFORMATION: synthetic primer

<400> SEQUENCE: 91
caggtgcagc tggtgsartc tgg                                               23

<210> SEQ ID NO 92
<211> LENGTH: 22
<212> TYPE: DNA
<213> ORGANISM: Artificial
<220> FEATURE:
<223> OTHER INFORMATION: synthetic primer

<400> SEQUENCE: 92
cagrtcacct tgaaggagtc tg                                                22

<210> SEQ ID NO 93
<211> LENGTH: 21
<212> TYPE: DNA
<213> ORGANISM: Artificial
<220> FEATURE:
<223> OTHER INFORMATION: synthetic primer

<400> SEQUENCE: 93
gaggtgcagc tgktggagwc y                                                 21

<210> SEQ ID NO 94
<211> LENGTH: 22
<212> TYPE: DNA
<213> ORGANISM: Artificial
<220> FEATURE:
<223> OTHER INFORMATION: synthetic primer

<400> SEQUENCE: 94
caggtgcagc tgcaggagtc sg                                                22

<210> SEQ ID NO 95
<211> LENGTH: 22
<212> TYPE: DNA
<213> ORGANISM: Artificial
<220> FEATURE:
<223> OTHER INFORMATION: synthetic primer

<400> SEQUENCE: 95
caggtgcagc tacagcagtg gg                                                22

<210> SEQ ID NO 96
<211> LENGTH: 21
<212> TYPE: DNA
<213> ORGANISM: Artificial
<220> FEATURE:
<223> OTHER INFORMATION: synthetic primer

<400> SEQUENCE: 96
```
caggtacagc tgcagcagtc a                                                        21

<210> SEQ ID NO 97
<211> LENGTH: 22
<212> TYPE: DNA
<213> ORGANISM: Artificial
<220> FEATURE:
<223> OTHER INFORMATION: synthetic primer

<400> SEQUENCE: 97
tcaacacaac ggttcccagt ta                                                       22

<210> SEQ ID NO 98
<211> LENGTH: 20
<212> TYPE: DNA
<213> ORGANISM: Artificial
<220> FEATURE:
<223> OTHER INFORMATION: synthetic primer

<400> SEQUENCE: 98
ggttggggcg gatgcactcc                                                          20

<210> SEQ ID NO 99
<211> LENGTH: 21
<212> TYPE: DNA
<213> ORGANISM: Artificial
<220> FEATURE:
<223> OTHER INFORMATION: synthetic primer

<400> SEQUENCE: 99
sgatgggccc ttggtggarg c                                                        21

<210> SEQ ID NO 100
<211> LENGTH: 20
<212> TYPE: DNA
<213> ORGANISM: Artificial
<220> FEATURE:
<223> OTHER INFORMATION: synthetic primer

<400> SEQUENCE: 100
ggctcctggg ggaagaagcc                                                          20

<210> SEQ ID NO 101
<211> LENGTH: 23
<212> TYPE: DNA
<213> ORGANISM: Artificial
<220> FEATURE:
<223> OTHER INFORMATION: synthetic primer

<400> SEQUENCE: 101
gacatccrgd tgacccagtc tcc                                                      23

<210> SEQ ID NO 102
<211> LENGTH: 23
<212> TYPE: DNA
<213> ORGANISM: Artificial
<220> FEATURE:
<223> OTHER INFORMATION: synthetic primer

<400> SEQUENCE: 102
gatattgtgm tgacbcagwc tcc                                                      23

<210> SEQ ID NO 103
<211> LENGTH: 23
<212> TYPE: DNA

<213> ORGANISM: Artificial
<220> FEATURE:
<223> OTHER INFORMATION: synthetic primer

<400> SEQUENCE: 103
gaaattgtrw tgacrcagtc tcc                                              23

<210> SEQ ID NO 104
<211> LENGTH: 22
<212> TYPE: DNA
<213> ORGANISM: Artificial
<220> FEATURE:
<223> OTHER INFORMATION: synthetic primer

<400> SEQUENCE: 104
gaaacgacac tcacgcagtc tc                                               22

<210> SEQ ID NO 105
<211> LENGTH: 20
<212> TYPE: DNA
<213> ORGANISM: Artificial
<220> FEATURE:
<223> OTHER INFORMATION: synthetic primer

<400> SEQUENCE: 105
tttgatttcc accttggtcc                                                  20

<210> SEQ ID NO 106
<211> LENGTH: 20
<212> TYPE: DNA
<213> ORGANISM: Artificial
<220> FEATURE:
<223> OTHER INFORMATION: synthetic primer

<400> SEQUENCE: 106
tttgatctcc ascttggtcc                                                  20

<210> SEQ ID NO 107
<211> LENGTH: 20
<212> TYPE: DNA
<213> ORGANISM: Artificial
<220> FEATURE:
<223> OTHER INFORMATION: synthetic primer

<400> SEQUENCE: 107
tttgatatcc actttggtcc                                                  20

<210> SEQ ID NO 108
<211> LENGTH: 20
<212> TYPE: DNA
<213> ORGANISM: Artificial
<220> FEATURE:
<223> OTHER INFORMATION: synthetic primer

<400> SEQUENCE: 108
tttaatctcc agtcgtgtcc                                                  20

<210> SEQ ID NO 109
<211> LENGTH: 23
<212> TYPE: DNA
<213> ORGANISM: Artificial
<220> FEATURE:
<223> OTHER INFORMATION: synthetic primer

<400> SEQUENCE: 109
cagtctgtsb tgacgcagcc gcc                                              23

```
<210> SEQ ID NO 110
<211> LENGTH: 20
<212> TYPE: DNA
<213> ORGANISM: Artificial
<220> FEATURE:
<223> OTHER INFORMATION: synthetic primer

<400> SEQUENCE: 110
cagcctgtgc tgactcaryc                                                  20

<210> SEQ ID NO 111
<211> LENGTH: 23
<212> TYPE: DNA
<213> ORGANISM: Artificial
<220> FEATURE:
<223> OTHER INFORMATION: synthetic primer

<400> SEQUENCE: 111
cagccwgkgc tgactcagcc mcc                                              23

<210> SEQ ID NO 112
<211> LENGTH: 21
<212> TYPE: DNA
<213> ORGANISM: Artificial
<220> FEATURE:
<223> OTHER INFORMATION: synthetic primer

<400> SEQUENCE: 112
cagtctgyyc tgaytcagcc t                                                21

<210> SEQ ID NO 113
<211> LENGTH: 22
<212> TYPE: DNA
<213> ORGANISM: Artificial
<220> FEATURE:
<223> OTHER INFORMATION: synthetic primer

<400> SEQUENCE: 113
tcctatgwgc tgacwcagcc aa                                               22

<210> SEQ ID NO 114
<211> LENGTH: 23
<212> TYPE: DNA
<213> ORGANISM: Artificial
<220> FEATURE:
<223> OTHER INFORMATION: synthetic primer

<400> SEQUENCE: 114
tcctctgagc tgastcagga scc                                              23

<210> SEQ ID NO 115
<211> LENGTH: 23
<212> TYPE: DNA
<213> ORGANISM: Artificial
<220> FEATURE:
<223> OTHER INFORMATION: synthetic primer

<400> SEQUENCE: 115
tcctatgagc tgayrcagcy acc                                              23

<210> SEQ ID NO 116
<211> LENGTH: 22
<212> TYPE: DNA
<213> ORGANISM: Artificial
<220> FEATURE:
```

-continued

<223> OTHER INFORMATION: synthetic primer

<400> SEQUENCE: 116
aattttatgc tgactcagcc cc                                        22

<210> SEQ ID NO 117
<211> LENGTH: 23
<212> TYPE: DNA
<213> ORGANISM: Artificial
<220> FEATURE:
<223> OTHER INFORMATION: synthetic primer

<400> SEQUENCE: 117
cagdctgtgg tgacycagga gcc                                       23

<210> SEQ ID NO 118
<211> LENGTH: 20
<212> TYPE: DNA
<213> ORGANISM: Artificial
<220> FEATURE:
<223> OTHER INFORMATION: synthetic primer

<400> SEQUENCE: 118
taggacggts ascttggtcc                                           20

<210> SEQ ID NO 119
<211> LENGTH: 20
<212> TYPE: DNA
<213> ORGANISM: Artificial
<220> FEATURE:
<223> OTHER INFORMATION: synthetic primer

<400> SEQUENCE: 119
gaggacggtc agctgggtgc                                           20

<210> SEQ ID NO 120
<211> LENGTH: 123
<212> TYPE: PRT
<213> ORGANISM: Artificial
<220> FEATURE:
<223> OTHER INFORMATION: antibody fragment

<400> SEQUENCE: 120

Gln Val Gln Leu Val Glu Ser Gly Gly Leu Val Gln Pro Gly Arg
1               5                   10                  15

Ser Leu Arg Leu Ser Cys Val Gly Ser Gly Phe Ser Phe Glu Ser Tyr
                20                  25                  30

Ala Met His Trp Val Arg Leu Ala Pro Gly Lys Gly Leu Glu Trp Val
            35                  40                  45

Ala Gly Ile Ser Trp Asp Ser Gly Ala Lys Gly Asn Ala Asp Ser Val
        50                  55                  60

Glu Gly Arg Phe Thr Ile Ser Arg Asp Asn Ala Lys Lys Ser Val Tyr
65                  70                  75                  80

Leu Glu Met Arg Ser Leu Arg Pro Glu Asp Thr Ala Phe Tyr Tyr Cys
                85                  90                  95

Ala Lys Ala Pro Ile Ile Gly Pro Lys Tyr Tyr Phe Tyr Met Asp Val
            100                 105                 110

Trp Gly Lys Gly Thr Ser Val Thr Val Ser Ser
        115                 120

<210> SEQ ID NO 121
<211> LENGTH: 120

-continued

```
<212> TYPE: PRT
<213> ORGANISM: Artificial
<220> FEATURE:
<223> OTHER INFORMATION: antibody fragment

<400> SEQUENCE: 121

Gln Val Gln Leu Val Gln Ser Gly Gly Gly Val Lys Gln Pro Gly Gly
1               5                   10                  15

Ser Leu Arg Leu Ser Cys Thr Ala Ser Gly Phe Thr Phe Glu Asp Phe
            20                  25                  30

Asn Met His Trp Val Arg Gln Ala Pro Gly Lys Gly Leu Glu Trp Ile
        35                  40                  45

Ser Tyr Ile Ser Gly Asp Gly Asp Arg Thr His Tyr Ser Asp Ser Val
    50                  55                  60

Arg Gly Arg Phe Thr Ile Ser Arg Asp Asn Ser Gly Asn Ser Leu Tyr
65                  70                  75                  80

Leu Gln Met Thr Ser Leu Arg Thr Glu Asp Ala Gly Phe Tyr Tyr Cys
                85                  90                  95

Gly Lys Ser Tyr Asp Tyr Ile Arg Glu Asn Leu Asp Ser Trp Gly Gln
            100                 105                 110

Gly Thr Leu Val Thr Val Ser Ser
        115                 120

<210> SEQ ID NO 122
<211> LENGTH: 123
<212> TYPE: PRT
<213> ORGANISM: Artificial
<220> FEATURE:
<223> OTHER INFORMATION: antibody fragment

<400> SEQUENCE: 122

Gln Val Gln Leu Val Gln Ser Gly Ala Glu Val Lys Lys Pro Gly Ala
1               5                   10                  15

Ser Val Arg Val Ser Cys Lys Ala Ser Gly Tyr Thr Phe Thr Arg Tyr
            20                  25                  30

Ala Met His Trp Val Arg Gln Ala Pro Gly Gln Arg Pro Glu Trp Met
        35                  40                  45

Gly Trp Ile Asn Val Asp Asn Gly Asn Thr Glu Tyr Ser Gln Lys Phe
    50                  55                  60

Gln Gly Arg Leu Thr Ile Thr Arg Asp Thr Ser Ala Ser Thr Ala Tyr
65                  70                  75                  80

Met Glu Leu Ser Ser Leu Thr Ser Asp Asp Thr Ala Val Tyr Tyr Cys
                85                  90                  95

Ala Lys Asp Arg Val Arg Val Val Gln Ala Ala Thr Thr Leu Asp Phe
            100                 105                 110

Trp Gly Gln Gly Thr Leu Val Thr Val Ser Ser
        115                 120

<210> SEQ ID NO 123
<211> LENGTH: 121
<212> TYPE: PRT
<213> ORGANISM: Artificial
<220> FEATURE:
<223> OTHER INFORMATION: antibody fragment

<400> SEQUENCE: 123

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Leu Ser Ser
```

```
            20                  25                  30
Gly Met Cys Val Ser Trp Ile Arg Gln Pro Gly Lys Ala Leu Glu
         35                  40                  45

Trp Leu Ala Arg Ile Asp Trp Asp Glu Lys Tyr Tyr Ser Pro Ser
     50                  55                  60

Leu Lys Thr Arg Leu Thr Ile Ser Lys Asp Thr Ser Lys Asp Gln Val
 65                  70                  75                  80

Val Leu Thr Met Thr Asn Met Asp Pro Leu Thr Ala Met Tyr Ser
                 85                  90                  95

Cys Ala Arg Gly Val Val Pro Ala Gly Ile Pro Phe Asp Phe Trp Gly
             100                 105                 110

Gln Gly Ile Met Val Thr Val Ser Ser
         115                 120

<210> SEQ ID NO 124
<211> LENGTH: 126
<212> TYPE: PRT
<213> ORGANISM: Artificial
<220> FEATURE:
<223> OTHER INFORMATION: antibody fragment

<400> SEQUENCE: 124

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Asn Ser Tyr
             20                  25                  30

Tyr Trp Ser Trp Ile Arg Gln Ser Pro Gly Lys Gly Leu Glu Trp Ile
         35                  40                  45

Gly Tyr Ile Tyr Tyr Thr Gly Ile Asn Lys Tyr Asn Pro Ser Leu Lys
     50                  55                  60

Ser Arg Val Thr Ile Ser Met Asp Thr Ser Lys Arg Gln Val Ser Leu
 65                  70                  75                  80

Lys Val Thr Ser Leu Thr Pro Ala Asp Thr Ala Val Tyr Phe Cys Ala
             85                  90                  95

Arg Leu His Pro Thr Cys Ala Ser Thr Arg Cys Pro Glu Asn Tyr Gly
            100                 105                 110

Met Asp Val Trp Gly Gln Gly Thr Thr Val Ala Val Ser Ser
        115                 120                 125

<210> SEQ ID NO 125
<211> LENGTH: 127
<212> TYPE: PRT
<213> ORGANISM: Artificial
<220> FEATURE:
<223> OTHER INFORMATION: antibody fragment

<400> SEQUENCE: 125

Gln Val Gln Leu Gln Glu Ser Gly Gly Gly Lys Leu Val Arg Pro Gly Gly
 1               5                  10                  15

Arg Leu Arg Leu Ser Cys Val Val Ser Gly Phe Thr Phe Ser Asp Phe
             20                  25                  30

Ala Met Ser Trp Val Arg Gln Ala Pro Gly Lys Gly Pro Leu Trp Val
         35                  40                  45

Ala Ala Val Ser Gly Ser Gly Asp Glu Thr Phe Tyr Ala Asp Ser Val
     50                  55                  60

Lys Gly Arg Phe Thr Ile Ser Arg Asp Asn Ser Lys Asn Thr Ile Phe
 65                  70                  75                  80
```

```
Leu Gln Met Thr Ser Leu Gly Val Glu Asp Thr Ala Leu Tyr Tyr Cys
                85                  90                  95
Val Arg Asp Pro Arg His Tyr His Asn Met Gly Arg Tyr Tyr Ala Gly
            100                 105                 110
Trp Phe Asp Ala Trp Gly Gln Gly Thr Arg Val Ile Val Ser Ser
        115                 120                 125
```

<210> SEQ ID NO 126
<211> LENGTH: 122
<212> TYPE: PRT
<213> ORGANISM: Artificial
<220> FEATURE:
<223> OTHER INFORMATION: antibody fragment

<400> SEQUENCE: 126

```
Gln Val Gln Leu Val Glu Ser Gly Ser Glu Val Arg Lys Pro Gly Ala
1               5                   10                  15
Ser Val Lys Val Ser Cys Lys Ala Ser Gly Tyr Thr Phe Ser Arg Tyr
            20                  25                  30
Gly Leu Thr Trp Val Arg Gln Ala Pro Gly Gln Gly Leu Glu Trp Met
        35                  40                  45
Gly Trp Ile Ser Gly Tyr Asn Ser Asn Thr Asn Tyr Ala Pro Lys Phe
    50                  55                  60
Gln Gly Arg Val Thr Met Thr Thr Asp Thr Ser Thr Asn Thr Ala Tyr
65                  70                  75                  80
Leu Glu Leu Arg Ser Leu Arg Ser Asn Asp Thr Ala Val Tyr Tyr Cys
                85                  90                  95
Ala Arg Asp Tyr Phe His Ser Gly Ser Gln Tyr Phe Asp Tyr Trp
            100                 105                 110
Gly Gln Gly Ser Leu Val Thr Val Ser Ser
        115                 120
```

<210> SEQ ID NO 127
<211> LENGTH: 122
<212> TYPE: PRT
<213> ORGANISM: Artificial
<220> FEATURE:
<223> OTHER INFORMATION: antibody fragment

<400> SEQUENCE: 127

```
Gln Val Gln Leu Gln Glu Ser Gly Pro Gly Leu Val Arg Pro Ser Gln
1               5                   10                  15
Thr Leu Ser Leu Thr Cys Thr Val Ser Gly Asp Ser Ile Ser Asp Gly
            20                  25                  30
Asp Ser Phe Trp Ser Trp Ile Arg Gln Pro Pro Gly Lys Gly Pro Glu
        35                  40                  45
Trp Ile Gly Tyr Ile Ser Ser Ser Gly Thr Thr Tyr Tyr Tyr Pro Ser
    50                  55                  60
Leu Arg Gly Arg Leu Thr Val Ser Leu Asp Ala Ser Lys Asn Gln Phe
65                  70                  75                  80
Ser Leu Ser Leu Thr Ser Val Thr Ala Ala Asp Thr Ala Val Tyr Tyr
                85                  90                  95
Cys Ala Arg Ala Arg Asn Tyr Gly Phe Pro His Phe Phe Asp Phe Trp
            100                 105                 110
Gly Arg Gly Thr Leu Val Thr Val Ser Ser
        115                 120
```

<210> SEQ ID NO 128

```
<211> LENGTH: 118
<212> TYPE: PRT
<213> ORGANISM: Artificial
<220> FEATURE:
<223> OTHER INFORMATION: antibody fragment

<400> SEQUENCE: 128
```

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser His Tyr
            20                  25                  30

Ser Met Asn Trp Ile Arg Gln Ala Pro Gly Lys Gly Leu Glu Trp Val
        35                  40                  45

Ala Ser Ile Thr Ser Gly Ser Thr Asn Met Val Tyr Ala Asp Ser Leu
    50                  55                  60

Arg Ala Arg Phe Ser Ile Ser Arg Asp Asn Ala Lys Asn Ser Leu Tyr
65                  70                  75                  80

Leu Gln Met Asp Ser Leu Ser Ala Glu Asp Thr Ala Val Tyr Tyr Cys
                85                  90                  95

Ala Arg Lys Gly Met Gly His Tyr Phe Asp Phe Trp Gly Gln Gly Thr
                100                 105                 110

Pro Val Thr Val Ser Ser
            115

```
<210> SEQ ID NO 129
<211> LENGTH: 122
<212> TYPE: PRT
<213> ORGANISM: Artificial
<220> FEATURE:
<223> OTHER INFORMATION: antibody fragment

<400> SEQUENCE: 129
```

Gln Val Gln Leu Gln Glu Ser Gly Pro Gly Leu Val Lys Pro Ser Gly
1               5                   10                  15

Thr Leu Ser Leu Thr Cys Ala Val Ser Gly Val Pro Val Tyr Thr Gly
            20                  25                  30

His Trp Trp Thr Trp Val Arg Gln Ala Pro Gly Lys Gly Leu Glu Trp
        35                  40                  45

Ile Gly Glu Ile His His Thr Val Thr Thr Asn Tyr Asn Pro Ser Leu
    50                  55                  60

Arg Ser Arg Val Thr Ile Ser Glu Asp Arg Ser Lys Asn Gln Ile Ser
65                  70                  75                  80

Leu Thr Leu Gln Ser Val Thr Ala Ala Asp Thr Ala Val Tyr Phe Cys
                85                  90                  95

Ala Arg Gly Glu Asp Cys Val Gly Gly Ser Cys Tyr Ser Ala Asp Trp
                100                 105                 110

Gly Gln Gly Ile Leu Val Thr Val Ser Ser
            115                 120

```
<210> SEQ ID NO 130
<211> LENGTH: 123
<212> TYPE: PRT
<213> ORGANISM: Artificial
<220> FEATURE:
<223> OTHER INFORMATION: antibody fragment

<400> SEQUENCE: 130
```

Gln Val Gln Leu Gln Glu Ser Gly Gly Gly Leu Val Gln Pro Gly Arg
1               5                   10                  15

Ser Leu Arg Leu Ser Cys Val Gly Ser Gly Phe Ser Phe Glu Ser Tyr
            20                  25                  30

Ala Met His Trp Val Arg Gln Ala Pro Gly Lys Gly Leu Glu Trp Val
            35                  40                  45

Ala Gly Ile Ser Trp Asp Ser Gly Ala Lys Gly Asn Ala Asp Ser Val
50                  55                  60

Glu Gly Arg Phe Thr Ile Ser Arg Asp Asn Ala Lys Lys Ser Leu Tyr
65                  70                  75                  80

Leu Glu Met Arg Ser Leu Arg Pro Glu Asp Thr Ala Phe Tyr Tyr Cys
            85                  90                  95

Ala Lys Ala Pro Ile Ile Gly Pro Lys His Tyr Phe Tyr Met Asp Val
            100                 105                 110

Trp Gly Lys Gly Thr Ser Val Thr Val Ser Ser
            115                 120

<210> SEQ ID NO 131
<211> LENGTH: 120
<212> TYPE: PRT
<213> ORGANISM: Artificial
<220> FEATURE:
<223> OTHER INFORMATION: antibody fragment

<400> SEQUENCE: 131

Gln Phe Lys Leu Val Glu Ser Gly Ser Trp Gly Lys Lys Pro Gly Ser
1               5                   10                  15

Ser Val Lys Val Ser Cys Lys Ala Ser Gly Asp Thr Leu Thr Ser Tyr
            20                  25                  30

Val Ile Thr Trp Leu Arg Gln Ala Pro Gly Gln Gly Pro Glu Trp Met
            35                  40                  45

Gly Glu Ile Ile Thr Met Phe Gly Thr Thr Lys Phe Ala Asn Asn Phe
50                  55                  60

His Gly Arg Met Thr Ile Thr Val Asp Glu Leu Lys Thr Thr Ala Tyr
65                  70                  75                  80

Met Glu Leu Thr Ser Leu Arg Ser Glu Asp Thr Ala Val Tyr Tyr Cys
            85                  90                  95

Ala Arg Gln Arg Pro Ser Pro Arg Trp Ala Phe Asp Ile Trp Gly Gln
            100                 105                 110

Gly Thr Met Val Thr Val Ser Ser
            115                 120

<210> SEQ ID NO 132
<211> LENGTH: 123
<212> TYPE: PRT
<213> ORGANISM: Artificial
<220> FEATURE:
<223> OTHER INFORMATION: antibody fragment

<400> SEQUENCE: 132

Gln Val Gln Leu Val Glu Ser Gly Ala Glu Val Lys Lys Pro Gly Ala
1               5                   10                  15

Ser Val Arg Val Ser Cys Lys Ala Ser Gly Tyr Thr Phe Thr Asn Tyr
            20                  25                  30

Gly Leu Ala Trp Val Arg Gln Ala Pro Gly Gln Gly Leu Glu Trp Met
            35                  40                  45

Gly Trp Ile Thr Val Tyr Asn Gly His Thr Ser Tyr Ala Gln Lys Phe
50                  55                  60

His Asp Arg Val Thr Met Thr Thr Asp Thr Ser Thr Arg Thr Ala Tyr
65                  70                  75                  80

Leu Glu Val Arg Asn Leu Gly Ser Asp Asp Thr Ala Val Tyr Tyr Cys
                85                  90                  95

Ala Arg Lys Pro Arg Phe Tyr Asp Thr Ser Ala Trp Phe Glu Phe
            100                 105                 110

Trp Gly Gln Gly Thr Leu Val Thr Val Ser Ser
            115                 120

<210> SEQ ID NO 133
<211> LENGTH: 108
<212> TYPE: PRT
<213> ORGANISM: Artificial
<220> FEATURE:
<223> OTHER INFORMATION: antibody fragment

<400> SEQUENCE: 133

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Lys Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Val Ala Val Tyr Tyr Cys Gln Gln Tyr Gly Thr Ser Arg
                85                  90                  95

Gly Thr Phe Gly Gln Gly Thr Arg Leu Glu Ile Lys
            100                 105

<210> SEQ ID NO 134
<211> LENGTH: 108
<212> TYPE: PRT
<213> ORGANISM: Artificial
<220> FEATURE:
<223> OTHER INFORMATION: antibody fragment

<400> SEQUENCE: 134

Gln Pro Gly Leu Thr Gln Pro Pro Ser Val Ser Val Ala Pro Gly Gln
1               5                   10                  15

Thr Ala Arg Ile Thr Cys Gly Gly Asn Asn Ile Gly Ser Arg His Val
            20                  25                  30

His Trp Tyr Gln Gln Arg Pro Gly Gln Ala Pro Val Leu Val Val Tyr
        35                  40                  45

Asp Asp Asp Ala Arg Pro Ser Gly Ile Ser Gly Arg Phe Ser Gly Ser
    50                  55                  60

Asn Ser Gly Asn Thr Ala Thr Leu Thr Ile Ser Trp Val Glu Ala Gly
65                  70                  75                  80

Asp Glu Ala Asp Tyr Tyr Cys Gln Val Ser Asp Ser Gly Arg Glu Trp
                85                  90                  95

Gly Val Phe Gly Ser Gly Thr Lys Val Thr Val Leu
            100                 105

<210> SEQ ID NO 135
<211> LENGTH: 109
<212> TYPE: PRT
<213> ORGANISM: Artificial
<220> FEATURE:
<223> OTHER INFORMATION: antibody fragment

<400> SEQUENCE: 135

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Ile Pro Ser Lys
            20                  25                  30

Tyr Leu Gly Trp Tyr Gln Gln Lys Leu Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Ser
                85                  90                  95

Ala Ile Thr Phe Gly Gln Gly Thr Arg Leu Glu Ile Lys
            100                 105

<210> SEQ ID NO 136
<211> LENGTH: 108
<212> TYPE: PRT
<213> ORGANISM: Artificial
<220> FEATURE:
<223> OTHER INFORMATION: antibody fragment

<400> SEQUENCE: 136

Glu Thr Thr Leu Thr Gln Ser Pro Ser Thr Leu Pro Ala Ser Val Gly
1               5                   10                  15

Asp Arg Val Thr Ile Thr Cys Arg Ala Ser Glu Asn Ile Asn Ser Trp
            20                  25                  30

Leu Ala Trp Tyr Gln Gln Lys Pro Gly Lys Ala Pro Lys Ile Leu Ile
        35                  40                  45

Tyr Arg Ala Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Asp Asp Lys Tyr Phe Ser
                85                  90                  95

Trp Thr Phe Gly His Gly Thr Lys Val Glu Ile Lys
            100                 105

<210> SEQ ID NO 137
<211> LENGTH: 107
<212> TYPE: PRT
<213> ORGANISM: Artificial
<220> FEATURE:
<223> OTHER INFORMATION: antibody fragment

<400> SEQUENCE: 137

Asp Ile Arg Leu Thr Gln Ser Pro Ser Ser Leu Ser Ala Ser Val Gly
1               5                   10                  15

Asp Arg Val Thr Ile Thr Cys Arg Ser Ser Gln Thr Ile Ser Thr Tyr
            20                  25                  30

Leu Asn Trp Tyr Gln Gln Lys Pro Gly Glu Ala Pro Lys Ile Leu Ile
        35                  40                  45

Tyr Ala Ala Ser Ser Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ile Tyr His Cys Gln Gln Ser Tyr Ser Thr Pro Tyr
                85                  90                  95

Thr Phe Gly Gln Gly Thr Lys Val Glu Ile Lys
            100                 105

<210> SEQ ID NO 138
<211> LENGTH: 110
<212> TYPE: PRT
<213> ORGANISM: Artificial
<220> FEATURE:
<223> OTHER INFORMATION: antibody fragment

<400> SEQUENCE: 138

Asp Ile Arg Val Thr Gln Ser Pro Glu Ser Leu Gly Met Ser Leu Gly
1               5                   10                  15

Glu Arg Ala Thr Leu Asn Cys Lys Ser Asn Gln Ser Leu Leu Tyr Thr
            20                  25                  30

Ser Lys Asn Tyr Leu Ala Trp Tyr Gln Gln Lys Pro Gly Gln Pro Pro
        35                  40                  45

Lys Leu Leu Ile Tyr Trp Ala Ser Thr Arg Gln Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Ala Glu Asp Val Ala Val Tyr Tyr Cys Gln Gln Tyr Tyr
                85                  90                  95

Asp Thr Pro Ser Phe Gly Pro Gly Thr Lys Val Asp Ile Lys
            100                 105                 110

<210> SEQ ID NO 139
<211> LENGTH: 107
<212> TYPE: PRT
<213> ORGANISM: Artificial
<220> FEATURE:
<223> OTHER INFORMATION: antibody fragment

<400> SEQUENCE: 139

Asp Ile Arg Leu Thr Gln Ser Pro Ser Ser Leu Ser Ala Ser Val Gly
1               5                   10                  15

Asp Arg Val Thr Ile Thr Cys Arg Ser Ser Gln Thr Ile Ser Thr Tyr
            20                  25                  30

Leu Asn Trp Tyr Gln Gln Lys Pro Gly Glu Ala Pro Lys Ile Leu Ile
        35                  40                  45

Tyr Ala Ala Ser Ser Leu His Thr Gly Val Pro Ser Arg Phe Ser Gly
    50                  55                  60

Ser Gly Ser Gly Thr Asp Phe Thr Leu Thr Ile Thr Ser Leu Gln Pro
65                  70                  75                  80

Glu Asp Phe Ala Ile Tyr His Cys Gln Gln Ser Tyr Ser Thr Pro Tyr
                85                  90                  95

Thr Phe Gly Gln Gly Thr Lys Val Glu Ile Lys
            100                 105

<210> SEQ ID NO 140
<211> LENGTH: 108
<212> TYPE: PRT
<213> ORGANISM: Artificial
<220> FEATURE:
<223> OTHER INFORMATION: antibody fragment

<400> SEQUENCE: 140

```
Asp Ile Gln Met Thr Gln Ser Pro Ser Thr Leu Ser Ala Ser Val Gly
1               5                   10                  15

Asp Ser Val Thr Ile Thr Cys Arg Ala Ser Gln Ser Ile Thr Arg Trp
            20                  25                  30

Leu Ala Trp Tyr Gln Gln Lys Pro Gly Lys Ala Pro Lys Leu Leu Ile
        35                  40                  45

Tyr Lys Ala Ser Leu Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Pro
                85                  90                  95

Trp Thr Phe Gly Pro Gly Thr Lys Leu Glu Ile Lys
                100                 105

<210> SEQ ID NO 141
<211> LENGTH: 110
<212> TYPE: PRT
<213> ORGANISM: Artificial
<220> FEATURE:
<223> OTHER INFORMATION: antibody fragment

<400> SEQUENCE: 141

Gln Thr Val Val Thr Gln Glu Pro Ser Ser Val Ser Leu Gly Gly
1               5                   10                  15

Thr Val Thr Leu Thr Cys Gly Leu Thr Ser Gly Pro Val Thr Gly Ala
            20                  25                  30

Tyr Tyr Pro Ser Trp His Gln Thr Pro Gly Gln Ala Pro Arg Thr
        35                  40                  45

Leu Ile Tyr Asn Thr Tyr Ser Leu Ser Ser Gly Val Ser Asp Arg Phe
    50                  55                  60

Ser Gly Ser Ile Leu Gly Asn Lys Ala Ala Leu Thr Ile Ser Gly Ala
65                  70                  75                  80

Gln Ala Asp Asp Glu Ser Asp Tyr Tyr Cys Val Leu Tyr Met Gly Ser
                85                  90                  95

Gly Ile Trp Met Phe Gly Gly Gly Thr Lys Leu Thr Val Leu
                100                 105                 110

<210> SEQ ID NO 142
<211> LENGTH: 107
<212> TYPE: PRT
<213> ORGANISM: Artificial
<220> FEATURE:
<223> OTHER INFORMATION: antibody fragment

<400> SEQUENCE: 142

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Asn Ile His Leu Phe
            20                  25                  30

Leu Asn Trp Tyr Gln Gln Arg Pro Gly Arg Val Pro Lys Val Leu Ile
        35                  40                  45

Tyr Ala Thr Ser Thr Leu Gln Ser Gly Val Pro Ser Arg Phe Ser Gly
    50                  55                  60

Ser Gly Ser Gly Thr Asp Phe Thr Leu Thr Ile Ser Ser Val Gln Pro
65                  70                  75                  80

Glu Asp Phe Ala Thr Tyr Tyr Cys Gln Gln Ser Phe Ser Thr Pro Arg
                85                  90                  95
```

Thr Phe Gly Pro Gly Thr Lys Val Glu Ile Lys
            100                 105

<210> SEQ ID NO 143
<211> LENGTH: 108
<212> TYPE: PRT
<213> ORGANISM: Artificial
<220> FEATURE:
<223> OTHER INFORMATION: antibody fragment

<400> SEQUENCE: 143

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Lys Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Thr Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Val Ala Val Tyr Tyr Cys Gln Gln Tyr Gly Thr Ser Arg
                85                  90                  95

Gly Thr Phe Gly Gln Gly Thr Arg Leu Glu Ile Lys
            100                 105

<210> SEQ ID NO 144
<211> LENGTH: 108
<212> TYPE: PRT
<213> ORGANISM: Artificial
<220> FEATURE:
<223> OTHER INFORMATION: antibody fragment

<400> SEQUENCE: 144

Asp Ile Gln Met Thr Gln Ser Pro Ser Thr Leu Ser Ala Ser Val Gly
1               5                   10                  15

Asp Arg Val Ser Ile Thr Cys Arg Ala Ser Gln Ser Ile Ser Gly Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Asn Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Pro
                85                  90                  95

Ser Thr Phe Gly Gln Gly Thr Lys Val Glu Ile Lys
            100                 105

<210> SEQ ID NO 145
<211> LENGTH: 106
<212> TYPE: PRT
<213> ORGANISM: Artificial
<220> FEATURE:
<223> OTHER INFORMATION: antibody fragment

<400> SEQUENCE: 145

Asp Ile Val Leu Thr Gln Ser Pro Glu Thr Leu Ser Val Ser Pro Gly
1               5                   10                  15

Glu Ser Ala Thr Leu Ser Cys Arg Ala Ser Gln Ser Val Ser Thr Asp
                20                  25                  30

Leu Ala Trp Tyr Gln His Lys Pro Gly Gln Ala Pro Arg Leu Leu Ile
            35                  40                  45

Trp Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Ile Cys Phe Cys His Gln Tyr Asn Asn Trp Pro Thr
                85                  90                  95

Phe Gly Gln Gly Thr Lys Val Glu Ile Lys
            100                 105

<210> SEQ ID NO 146
<211> LENGTH: 16
<212> TYPE: PRT
<213> ORGANISM: Artificial
<220> FEATURE:
<223> OTHER INFORMATION: antibody fragment

<400> SEQUENCE: 146

Ala Lys Ala Pro Ile Ile Gly Pro Lys Tyr Tyr Phe Tyr Met Asp Val
1               5                   10                  15

<210> SEQ ID NO 147
<211> LENGTH: 14
<212> TYPE: PRT
<213> ORGANISM: Artificial
<220> FEATURE:
<223> OTHER INFORMATION: antibody fragment

<400> SEQUENCE: 147

Cys Gly Lys Ser Tyr Asp Tyr Ile Arg Glu Asn Leu Asp Ser
1               5                   10

<210> SEQ ID NO 148
<211> LENGTH: 16
<212> TYPE: PRT
<213> ORGANISM: Artificial
<220> FEATURE:
<223> OTHER INFORMATION: antibody fragment

<400> SEQUENCE: 148

Ala Lys Asp Arg Val Arg Val Val Gln Ala Ala Thr Thr Leu Asp Phe
1               5                   10                  15

<210> SEQ ID NO 149
<211> LENGTH: 12
<212> TYPE: PRT
<213> ORGANISM: Artificial
<220> FEATURE:
<223> OTHER INFORMATION: antibody fragment

<400> SEQUENCE: 149

Ala Arg Gly Val Val Pro Ala Gly Ile Pro Phe Asp
1               5                   10

<210> SEQ ID NO 150
<211> LENGTH: 18
<212> TYPE: PRT
<213> ORGANISM: Artificial
<220> FEATURE:
<223> OTHER INFORMATION: antibody fragment

<400> SEQUENCE: 150

```
Ala Arg Leu His Pro Thr Cys Ala Ser Thr Arg Cys Pro Glu Asn Tyr
1               5                   10                  15

Gly Met

<210> SEQ ID NO 151
<211> LENGTH: 19
<212> TYPE: PRT
<213> ORGANISM: Artificial
<220> FEATURE:
<223> OTHER INFORMATION: antibody fragment

<400> SEQUENCE: 151

Val Arg Asp Pro Arg His Tyr His Asn Met Gly Arg Tyr Tyr Ala Gly
1               5                   10                  15

Trp Phe Asp

<210> SEQ ID NO 152
<211> LENGTH: 15
<212> TYPE: PRT
<213> ORGANISM: Artificial
<220> FEATURE:
<223> OTHER INFORMATION: antibody fragment

<400> SEQUENCE: 152

Ala Arg Asp Tyr Phe His Ser Gly Ser Gln Tyr Phe Phe Asp Tyr
1               5                   10                  15

<210> SEQ ID NO 153
<211> LENGTH: 14
<212> TYPE: PRT
<213> ORGANISM: Artificial
<220> FEATURE:
<223> OTHER INFORMATION: antibody fragment

<400> SEQUENCE: 153

Ala Arg Ala Arg Asn Tyr Gly Phe Pro His Phe Phe Asp Phe
1               5                   10

<210> SEQ ID NO 154
<211> LENGTH: 11
<212> TYPE: PRT
<213> ORGANISM: Artificial
<220> FEATURE:
<223> OTHER INFORMATION: antibody fragment

<400> SEQUENCE: 154

Ala Arg Lys Gly Met Gly His Tyr Phe Asp Phe
1               5                   10

<210> SEQ ID NO 155
<211> LENGTH: 15
<212> TYPE: PRT
<213> ORGANISM: Artificial
<220> FEATURE:
<223> OTHER INFORMATION: antibody fragment

<400> SEQUENCE: 155

Ala Arg Gly Glu Asp Cys Val Gly Gly Ser Cys Tyr Ser Ala Asp
1               5                   10                  15

<210> SEQ ID NO 156
<211> LENGTH: 17
<212> TYPE: PRT
<213> ORGANISM: Artificial
<220> FEATURE:
```

```
<223> OTHER INFORMATION: antibody fragment

<400> SEQUENCE: 156

Ala Lys Ala Pro Ile Ile Gly Pro Lys His Tyr Phe Tyr Met Asp Val
1               5                   10                  15

Trp

<210> SEQ ID NO 157
<211> LENGTH: 17
<212> TYPE: PRT
<213> ORGANISM: Artificial
<220> FEATURE:
<223> OTHER INFORMATION: antibody fragment

<400> SEQUENCE: 157

Ala Arg Gln Arg Pro Ser Pro Arg Trp Ala Phe Asp Ile Trp Gly Gln
1               5                   10                  15

Gly

<210> SEQ ID NO 158
<211> LENGTH: 16
<212> TYPE: PRT
<213> ORGANISM: Artificial
<220> FEATURE:
<223> OTHER INFORMATION: antibody fragment

<400> SEQUENCE: 158

Ala Arg Lys Pro Arg Phe Tyr Tyr Asp Thr Ser Ala Trp Phe Glu Phe
1               5                   10                  15

<210> SEQ ID NO 159
<211> LENGTH: 19
<212> TYPE: DNA
<213> ORGANISM: Artificial
<220> FEATURE:
<223> OTHER INFORMATION: synthetic primer

<400> SEQUENCE: 159
cgcagtagcg gtaaacggc                                            19

<210> SEQ ID NO 160
<211> LENGTH: 22
<212> TYPE: DNA
<213> ORGANISM: Artificial
<220> FEATURE:
<223> OTHER INFORMATION: synthetic primer

<400> SEQUENCE: 160
gcggataaca atttcacaca gg                                        22

<210> SEQ ID NO 161
<211> LENGTH: 38
<212> TYPE: DNA
<213> ORGANISM: Artificial
<220> FEATURE:
<223> OTHER INFORMATION: synthetic primer

<400> SEQUENCE: 161
cgcagtagcg gtaaacggca gggygccagg gggaagac                       38

<210> SEQ ID NO 162
<211> LENGTH: 39
<212> TYPE: DNA
<213> ORGANISM: Artificial
<220> FEATURE:
```

<223> OTHER INFORMATION: synthetic primer

<400> SEQUENCE: 162
cgcagtagcg gtaaacggcc gggaagacct tggggctgg　　　　　　　　　　　　39

<210> SEQ ID NO 163
<211> LENGTH: 39
<212> TYPE: DNA
<213> ORGANISM: Artificial
<220> FEATURE:
<223> OTHER INFORMATION: synthetic primer

<400> SEQUENCE: 163
cgcagtagcg gtaaacggcc acaggagacg aggggggaaa　　　　　　　　　　　　39

<210> SEQ ID NO 164
<211> LENGTH: 42
<212> TYPE: DNA
<213> ORGANISM: Artificial
<220> FEATURE:
<223> OTHER INFORMATION: synthetic primer

<400> SEQUENCE: 164
gcggataaca atttcacaca gggatgaaga cagatggtgc ag　　　　　　　　　　　42

<210> SEQ ID NO 165
<211> LENGTH: 42
<212> TYPE: DNA
<213> ORGANISM: Artificial
<220> FEATURE:
<223> OTHER INFORMATION: synthetic primer

<400> SEQUENCE: 165
gcggataaca atttcacaca ggtcctcaga ggagggyggg aa　　　　　　　　　　　42

<210> SEQ ID NO 166
<211> LENGTH: 40
<212> TYPE: DNA
<213> ORGANISM: Artificial
<220> FEATURE:
<223> OTHER INFORMATION: synthetic primer

<400> SEQUENCE: 166
tattcccatg gcgcgcccag gtccagctkg trcagtctgg　　　　　　　　　　　　40

<210> SEQ ID NO 167
<211> LENGTH: 40
<212> TYPE: DNA
<213> ORGANISM: Artificial
<220> FEATURE:
<223> OTHER INFORMATION: synthetic primer

<400> SEQUENCE: 167
tattcccatg gcgcgcccag gtgcagctgg tgsartctgg　　　　　　　　　　　　40

<210> SEQ ID NO 168
<211> LENGTH: 39
<212> TYPE: DNA
<213> ORGANISM: Artificial
<220> FEATURE:
<223> OTHER INFORMATION: synthetic primer

<400> SEQUENCE: 168
tattcccatg gcgcgcccag rtcaccttga aggagtctg　　　　　　　　　　　　39

```
<210> SEQ ID NO 169
<211> LENGTH: 38
<212> TYPE: DNA
<213> ORGANISM: Artificial
<220> FEATURE:
<223> OTHER INFORMATION: synthetic primer

<400> SEQUENCE: 169
tattcccatg gcgcgccgag gtgcagctgk tggagwcy                    38

<210> SEQ ID NO 170
<211> LENGTH: 39
<212> TYPE: DNA
<213> ORGANISM: Artificial
<220> FEATURE:
<223> OTHER INFORMATION: synthetic primer

<400> SEQUENCE: 170
tattcccatg gcgcgcccag gtgcagctgc aggagtcsg                   39

<210> SEQ ID NO 171
<211> LENGTH: 39
<212> TYPE: DNA
<213> ORGANISM: Artificial
<220> FEATURE:
<223> OTHER INFORMATION: synthetic primer

<400> SEQUENCE: 171
tattcccatg gcgcgcccag gtgcagctac agcagtggg                   39

<210> SEQ ID NO 172
<211> LENGTH: 38
<212> TYPE: DNA
<213> ORGANISM: Artificial
<220> FEATURE:
<223> OTHER INFORMATION: synthetic primer

<400> SEQUENCE: 172
tattcccatg gcgcgcccag gtacagctgc agcagtca                    38

<210> SEQ ID NO 173
<211> LENGTH: 39
<212> TYPE: DNA
<213> ORGANISM: Artificial
<220> FEATURE:
<223> OTHER INFORMATION: synthetic primer

<400> SEQUENCE: 173
tattcccatg gcgcgcctca acacaacggt tcccagtta                   39

<210> SEQ ID NO 174
<211> LENGTH: 43
<212> TYPE: DNA
<213> ORGANISM: Artificial
<220> FEATURE:
<223> OTHER INFORMATION: synthetic primer

<400> SEQUENCE: 174
ggcgcgccat gggaatagcc gacatccrgd tgacccagtc tcc              43

<210> SEQ ID NO 175
<211> LENGTH: 43
<212> TYPE: DNA
<213> ORGANISM: Artificial
<220> FEATURE:
<223> OTHER INFORMATION: synthetic primer
```

<400> SEQUENCE: 175
ggcgcgccat gggaatagcc gatattgtgm tgacbcagwc tcc        43

<210> SEQ ID NO 176
<211> LENGTH: 43
<212> TYPE: DNA
<213> ORGANISM: Artificial
<220> FEATURE:
<223> OTHER INFORMATION: synthetic primer

<400> SEQUENCE: 176
ggcgcgccat gggaatagcc gaaattgtrw tgacrcagtc tcc        43

<210> SEQ ID NO 177
<211> LENGTH: 42
<212> TYPE: DNA
<213> ORGANISM: Artificial
<220> FEATURE:
<223> OTHER INFORMATION: synthetic primer

<400> SEQUENCE: 177
ggcgcgccat gggaatagcc gaaacgacac tcacgcagtc tc         42

<210> SEQ ID NO 178
<211> LENGTH: 43
<212> TYPE: DNA
<213> ORGANISM: Artificial
<220> FEATURE:
<223> OTHER INFORMATION: synthetic primer

<400> SEQUENCE: 178
ggcgcgccat gggaatagcc cagtctgtsb tgacgcagcc gcc        43

<210> SEQ ID NO 179
<211> LENGTH: 40
<212> TYPE: DNA
<213> ORGANISM: Artificial
<220> FEATURE:
<223> OTHER INFORMATION: synthetic primer

<400> SEQUENCE: 179
ggcgcgccat gggaatagcc cagcctgtgc tgactcaryc            40

<210> SEQ ID NO 180
<211> LENGTH: 43
<212> TYPE: DNA
<213> ORGANISM: Artificial
<220> FEATURE:
<223> OTHER INFORMATION: synthetic primer

<400> SEQUENCE: 180
ggcgcgccat gggaatagcc cagccwgkgc tgactcagcc mcc        43

<210> SEQ ID NO 181
<211> LENGTH: 41
<212> TYPE: DNA
<213> ORGANISM: Artificial
<220> FEATURE:
<223> OTHER INFORMATION: synthetic primer

<400> SEQUENCE: 181
ggcgcgccat gggaatagcc cagtctgyyc tgaytcagcc t          41

<210> SEQ ID NO 182
<211> LENGTH: 42

<212> TYPE: DNA
<213> ORGANISM: Artificial
<220> FEATURE:
<223> OTHER INFORMATION: synthetic primer

<400> SEQUENCE: 182
ggcgcgccat gggaatagcc tcctatgwgc tgacwcagcc aa    42

<210> SEQ ID NO 183
<211> LENGTH: 43
<212> TYPE: DNA
<213> ORGANISM: Artificial
<220> FEATURE:
<223> OTHER INFORMATION: synthetic primer

<400> SEQUENCE: 183
ggcgcgccat gggaatagcc tcctctgagc tgastcagga scc    43

<210> SEQ ID NO 184
<211> LENGTH: 43
<212> TYPE: DNA
<213> ORGANISM: Artificial
<220> FEATURE:
<223> OTHER INFORMATION: synthetic primer

<400> SEQUENCE: 184
ggcgcgccat gggaatagcc tcctatgagc tgayrcagcy acc    43

<210> SEQ ID NO 185
<211> LENGTH: 42
<212> TYPE: DNA
<213> ORGANISM: Artificial
<220> FEATURE:
<223> OTHER INFORMATION: synthetic primer

<400> SEQUENCE: 185
ggcgcgccat gggaatagcc aattttatgc tgactcagcc cc    42

<210> SEQ ID NO 186
<211> LENGTH: 43
<212> TYPE: DNA
<213> ORGANISM: Artificial
<220> FEATURE:
<223> OTHER INFORMATION: synthetic primer

<400> SEQUENCE: 186
ggcgcgccat gggaatagcc cagdctgtgg tgacycagga gcc    43

<210> SEQ ID NO 187
<211> LENGTH: 31
<212> TYPE: DNA
<213> ORGANISM: Artificial
<220> FEATURE:
<223> OTHER INFORMATION: synthetic primer

<400> SEQUENCE: 187
atgggccctg sgatgggccc ttggtggarg c    31

<210> SEQ ID NO 188
<211> LENGTH: 30
<212> TYPE: DNA
<213> ORGANISM: Artificial
<220> FEATURE:
<223> OTHER INFORMATION: synthetic primer

<400> SEQUENCE: 188

```
atgggccctg cttggggctg gtcggggatg                                   30

<210> SEQ ID NO 189
<211> LENGTH: 30
<212> TYPE: DNA
<213> ORGANISM: Artificial
<220> FEATURE:
<223> OTHER INFORMATION: synthetic primer

<400> SEQUENCE: 189
atgggccctg ggttggggcg gatgcactcc                                   30

<210> SEQ ID NO 190
<211> LENGTH: 30
<212> TYPE: DNA
<213> ORGANISM: Artificial
<220> FEATURE:
<223> OTHER INFORMATION: synthetic primer

<400> SEQUENCE: 190
gtgcggccgc agatggtgca gccacagttc                                   30

<210> SEQ ID NO 191
<211> LENGTH: 30
<212> TYPE: DNA
<213> ORGANISM: Artificial
<220> FEATURE:
<223> OTHER INFORMATION: synthetic primer

<400> SEQUENCE: 191
gtgcggccgc gagggyggga acagagtgac                                   30

<210> SEQ ID NO 192
<211> LENGTH: 15
<212> TYPE: PRT
<213> ORGANISM: Artificial Sequence
<220> FEATURE:
<223> OTHER INFORMATION: Synthetic peptide

<400> SEQUENCE: 192

Gly Gly Gly Gly Ser Gly Gly Gly Gly Ser Gly Gly Gly Gly Ser
1               5                   10                  15
```

PROTEOMIC IDENTIFICATION OF ANTIBODIES

This application is a continuation of U.S. patent application Ser. No. 13/684,395, filed Nov. 23, 2012, now issued as U.S. Pat. No. 9,146,241, which claims the benefit of U.S. Provisional Patent Application No. 61/563,380, filed Nov. 23, 2011, the entirety of each of which is incorporated herein by reference. This application is also a continuation-in-part of U.S. patent application Ser. No. 14/809,651, filed Jul. 27, 2015, which is a continuation of U.S. patent application Ser. No. 13/109,467, filed May 17, 2011, now issued as U.S. Pat. No. 9,090,674, which claims the benefit of U.S. Provisional Patent Application Nos. 61/345,538 and 61/377,816, filed May 17, 2010 and Aug. 27, 2010, respectively.

This invention was made with government support under Grant no. HR0011-10-1-0052 awarded by the Defense Advanced Research Projects Agency, DARPA. The government has certain rights in the invention.

The present invention was made as a result of activities undertaken within the scope of a joint research agreement that was in effect at the time the present invention was made. The parties to said joint research agreement are Board of Regents of the University of Texas System and Clayton Foundation for Research and its affiliated entity Research Development Foundation.

This application is related to U.S. patent application Ser. No. 13/109,467, filed May 17, 2011, the entirety of which is incorporated herein by reference.

INCORPORATION OF SEQUENCE LISTING

The sequence listing that is contained in the file named "UTSBP1004USC1_ST25.txt", which is 78 KB (as measured in Microsoft Windows®) and was created on Sep. 23, 2015, is filed herewith by electronic submission and is incorporated by reference herein.

BACKGROUND OF THE INVENTION

1. Field of the Invention

The present invention relates generally to the field of antibody analysis and generation, such as antibody discovery from immunized animals. More particularly, it concerns novel methods and compositions for identification and/or production of desired antibodies or antigen-binding fragments.

2. Description of Related Art

Over the last 12 years, the development of cancer therapeutic antibodies, such as Herceptin (Trastuzumab, anti-Her2), Rituxan (Rituximab, anti-CD20), Eribitux/Vectibix (Cetuximab/Panitumumab, anti-EGFR), Avastin (anti-VEGF), and others, have saved many tens of thousands of lives world-wide. Antibody therapeutics offer distinct advantages relative to small molecule drugs, namely: (i) better understood mechanisms of action; (ii) higher specificity and fewer-off target effects; (iii) predictable safety and toxicological profiles. Currently, there are more than 200 antibody therapeutics in clinical trials in the U.S., many of them for cancer treatment.

The discovery of monoclonal antibodies is an immensely important aspect in therapeutic antibody development. Additionally, monoclonal antibodies are widely used for numerous diagnostic and analytical purposes. Since the development of the hybridoma technology by Kohler and Milstein 35 years ago (Kohler and Milstein, 1975), a variety of methods for the generation of MAbs have been developed. Such methods include B-cell immortalization by genetic reprogramming via Epstein-Barr virus (Traggiai et al., 2004) or retrovirus-mediated gene transfer (Kwakkenbos et al., 2010), cloning of V genes by single-cell PCR (Wrammert et al., 2008; Meijer et al., 2008), and methods for in vitro discovery via the display and screening of recombinant antibody libraries (Clackson et al., 1991; Feldhaus et al., 2003; Harvey et al., 2004; Schaffitzel et al., 1999; Hosse et al., 2006; Mazor et al., 2007; Zahnd et al., 2007; Kretzschmar and von Ruden, 2002). Both in vitro and in vivo methods for antibody discovery are critically dependent on high-throughput screening to determine antigen specificity. Recently, B-cell analysis has been expedited by microengraving techniques that utilize soft lithography for the high-throughput identification of antigen-specific B cells; however, this is at the cost of considerable technical complexity due to the need for antibody V gene amplification and cell expansion (Jin et al., 2009; Love et al., 2006).

Similarly, the success of in vitro antibody discovery techniques is dependent on screening parameters including the nature of the display platform, antigen concentration, binding avidity during enrichment, multiple rounds of screening (e.g., panning or sorting), and importantly, on the design and diversity of synthetic antibody libraries (Hoogenboom, 2005; Cobaugh et al., 2008; Persson et al., 2006).

Current use of display technologies coupled with library screening systems, such as a phage display where antibodies are isolated by panning, has a number of significant problems. In particular, some antibodies produced by a library may cause the death of the organism expressing them and therefore they simply cannot be detected. There is a particular problem when one is searching for antibodies specific to an antigen from a pathogen that might be homologous to one produced by the host expression system (e.g., *E. coli*) because, in that instance, important antibodies cannot be expressed. The use of *E. coli* to express libraries of human antibodies also suffers from the problem of codon usage. Codons used by humans for specific amino acids are frequently not the optimum ones for the same amino acid in *E. coli* or other host systems. This means that an important antibody might not be expressed (or at least not in sufficient quantities) since the codons in its sequence are highly inefficient in *E. coli*, resulting in the *E. coli* being unable to read through and express it in full. Codon optimization of antibody libraries is obviously not an option since the libraries would first have to be sequenced, which defeats the main advantages of using libraries.

There is a pressing need to identify biologically relevant antibodies that exhibit a beneficial effect in controlling diseases. Mammals mount antibody (humoral) immune responses against infectious agents, toxins, or cancer cells. Diseased individuals produce circulating antibodies that recognize the disease agent, and in many cases (e.g., in patients that recover from an infection or in cancer patients in remission) these antibodies play a key role in recovery and therapy. Currently there are no methods available to identify the circulating antibodies in blood and to produce the antibodies that are specific to the disease agent and have a therapeutic effect.

On the other hand, the isolation of monoclonal antibodies from different animal species is of great value for the development of therapeutics and diagnostics. A major limitation of the existing methods for isolation of monoclonal antibodies is that their application is limited to a very small number of species. Different animals have evolved distinct ways of diversifying their antibody repertoire and thus can produce antibodies that recognize distinct epitopes on an antigen or display very high affinity for a particular antigen, compared to mice and humans. For example, it is well known in the art that antibodies from rabbits generally display much higher affinity than those produced from mice.

Current production of monoclonal antibodies from a particular species using hybridoma technology necessitates that B cells are immortalized by fusion to a myeloma from that species. Such myeloma cell lines are difficult and time consuming to develop and therefore exist only for mice, primates, rabbits, and sheep. Alternatively, researchers have attempted to generate interspecies hybridomas, by fusing a mouse myeloma cell line with B cells from an animal for which autologous myeloma cell lines are not available. However, interspecies hybrids are generated with very low efficiency and are unstable, ceasing to produce monoclonal antibodies after a few passages. Thus, at present the production of monoclonal antibodies from the vast majority of animals that have an adaptive immunoglobulin system is a major challenge. Moreover, even for species for which stable B-cell fusions can be generated (rabbits, mice, sheep, and primates) the isolation of monoclonal antibodies using hybridoma technology is a lengthy process requiring 2-6 months after animal sacrifice.

Alternatively monoclonal antibodies can be isolated in vitro from large libraries of the variable (V) chains of the immunoglobulin repertoire from an immunized animal and then screening by a variety of display methods, such as phage display, yeast display, or bacterial display. Once again the utility of these methods is limited to the few species for which extensive information on their immunoglobulin repertoire is available, namely mice, primates, and rabbits. This is because the cloning of the immunoglobulin repertoire requires the availability of sets of oligonucleotide primers capable of amplifying the majority, preferably all, of the immunoglobulin variable regions that are generated in that animal via somatic recombination mechanisms. This in turn requires extensive information on the sequences of immunoglobulins expressed in a particular species and it is not available for the vast majority of animals that have an antibody-encoding, humoral immune system. Additionally, it is not known whether the antibodies isolated by combinatorial library screening correspond to those that have been expanded by the immune system and produced in large amounts in animals.

All of these techniques are somewhat complex, inconvenient, and time consuming. Therefore, there remains a need to develop a more efficient and accurate method for identifying antigen-specific antibodies or monoclonal antibodies directly from a patient or any animal.

SUMMARY OF THE INVENTION

Aspects of the present invention overcome a major deficiency in the art by providing novel methods for determining antibody sequences in a biological sample, such as serum. Accordingly, in a first embodiment there is provided a method for determining antibody $V_H$ or $V_L$ sequences in a subject comprising (a) obtaining nucleic acid, and the corresponding amino acid, sequence information of $V_H$ or $V_L$ gene repertoires of a subject; (b) obtaining mass spectra of peptides derived from antibodies of the subject; and (c) using the sequence information and the mass spectra to determine the amino acid sequence of the $V_H$ of $V_L$ of one or more antibodies in the subject, wherein step (a) or (b) comprises obtaining a sample from the subject.

In certain aspects, obtaining mass spectra of peptides derived from antibodies comprises obtaining mass spectra of peptides that have been modified with two different cysteine modifying agents. In some aspects, the mass difference between peptides modified with the two different cysteine modifying agents is determined and correlated spectra exhibiting the expected differential mass shift but identified as different peptide sequences are labeled as misidentified peptides and can be removed or not used to determine an antibody sequence. Examples of cysteine modifying agents for use according to the embodiments include, but are not limited to, iodoacetamide and iodoethanol (e.g., with a mass difference of ~13 Da (12.995 Da)).

In further aspects, using sequence information and mass spectra to determine the amino acid sequence of a $V_H$ or $V_L$ comprises determining the average mass deviation (AMD) for the peptides and retaining sequence with an AMD less than a threshold value. For example, AMD can be determined by comparing the average observed masses of peptides obtained by mass spectrometry to the expected masses based on the amino acid sequence to thereby determine the average difference between obtained and expected peptide masses. For example, the threshold value can be 3.0 ppm or less, such as 3.0 ppm, 2.5 ppm, 2.0 ppm, 1.5 ppm, 1.0 ppm, or 0.5 ppm and only peptides with an AMD below this threshold are used to determine a $V_H$ or $V_L$ sequence.

Thus, in a further embodiment, a method is provided for determining antibody $V_H$ or $V_L$ sequences in a subject (e.g., sequences in circulation) comprising (a) obtaining nucleic acid, and the corresponding amino acid, sequence information of $V_H$ or $V_L$ gene repertoires of a subject; (b) obtaining mass spectra of peptides derived from antibodies of the subject; (c) screening the mass spectra to remove misidentified peptides by determining the average mass deviation (AMD) for the peptides and retaining sequence with an AMD less than a threshold value; and (d) using the sequence information and the screened mass spectra to determine the amino acid sequence of the $V_H$ or $V_L$ of one or more antibodies in the subject, wherein step (a) or (b) comprises obtaining a sample from the subject. As described above, in some aspects, the threshold value can be 3.0 ppm or less, such as 3.0 ppm, 2.5 ppm, 2.0 ppm, 1.5 ppm, 1.0 ppm, or 0.5 ppm.

In a further embodiment a method if provided of identifying a repertoire of different antibodies specific to an antigen in a biological fluid of a subject comprising a) obtaining nucleic acid, and the corresponding amino acid, sequence information of the $V_H$ and natively paired $V_L$ gene repertoires encoded by a plurality of B cells in a subject; b) obtaining mass spectra of peptides derived from antibody $V_H$ or $V_L$ chains of the subject; and c) using the sequence information and the mass spectra to determine the amino acid sequence of the $V_H$ and $V_L$ of antibodies in the biological fluid of the subject, wherein step a) or b) comprises obtaining a sample from the subject. For example, in some aspects, step b) comprises obtaining mass spectra of peptides derived from antibody $V_H$, $V_L$ or $V_H$, and $V_L$ chains of the subject.

In a still a further embodiment a method is provided for of identifying a repertoire of different $V_H$ and/or $V_L$ chains from antibodies specific to an antigen in a biological fluid of a subject comprising: a) obtaining nucleic acid, and the corresponding amino acid, sequence information of the $V_H$ and/or $V_L$ gene repertoires encoded by a plurality of B cells in a subject; b) identifying the clonotype for each of the $V_H$ and/or $V_L$ genes; c) obtaining mass spectra of peptides derived from $V_H$ and/or $V_L$ chains of antibodies of the subject; and d) using the sequence information and the mass spectra to determine the amino acid sequence of the $V_H$ of one or more antibodies in the biological fluid of the subject, wherein step a) or c) comprises obtaining a sample from the subject. Thus, in certain aspects, a method of the embodiments is defined as a method of identifying a repertoire of different antibodies in a subject. In certain aspects, a method comprises identifying 5, 10, 15, 20, 25, 50, 100 or more clonotypes, such as between about 5 and 250 antibody clonotypes.

As used herein an antibody "clonotype" refers to antibodies that are derived from the same B-cell lineage and have the same V and J germ line sequences. Such antibodies bind to substantially the same epitope of an antigen. Antibodies from the same clonotype will comprise highly homologous but not identical variable chain sequences. In certain aspects, antibody chains of the same clonotype are identified by comparing CDR3 sequences (in particular VH CDR3 sequences). For example, for antibody chains having a CDR3 of 1-5 amino acids, antibody chains of the same clonotype have identical CDR3 sequences. For antibody chains with a CDR3 sequence of 6-10 amino acids, antibodies of the same clonotype have no more than a single mismatch in the CDR3 sequence. For antibody chains with a CDR3 sequence of over 10 amino acids, antibodies of the same clonotype have CDR3 sequences that are at least 90% identical.

In yet a further embodiment there is provided a method for determining antibody $V_H$ or $V_L$ sequences to an antigen in a biological fluid of a subject, comprising: a) obtaining nucleic acid, and the corresponding amino acid, sequence information of the $V_H$ or $V_L$ gene repertoires of a subject; b) obtaining mass spectra of peptides derived from antibodies in biological fluids of the subject, wherein the peptides have been modified with a peptide modifying agent (e.g., a cysteine modifying agent); and c) using the sequence information and the mass spectra from (a) and (b) to determine the amino acid sequence of the $V_H$ or $V_L$ of one or more antibodies in a biological fluid of the subject, wherein step a) or b) comprises obtaining a sample from the subject. For example, in some aspects, the peptides (of step b) from a portion of the sample have been modified with a peptide modifying agent and peptides from a portion of the sample have not been modified with a peptide modifying agent (or have been modified with a second peptide modifying agent). Accordingly, in some aspects, step c) comprises using a threshold filter for eliminating false peptide identifications by determining whether the difference in mass spectra of modified peptides from unmodified peptides or peptides modified with a second peptide modifying agent is equal to the expected mass change resulting from the modifying agent. In still further aspects, step c) further comprises determining the average mass deviation (AMD) between observed and estimated peptide masses, for modified and unmodified peptides for the peptides and retaining sequence with an AMD less than a threshold value as correct peptide identifications. For example, the threshold value can be 5.0 ppm, 3.0 ppm, 2.5 ppm, 2.0 ppm, 1.5 ppm, 1.0 ppm, or 0.5 ppm.

Certain aspects of the embodiments concern obtaining nucleic acid, and the corresponding amino acid, sequence information of the $V_H$ and natively paired $V_L$ gene. In some aspects, such a method comprises co-isolating nucleic acid encoding $V_H$ and $V_L$ genes from single B-cells (e.g., as exemplified herein). Thus, in some aspects, a method of the embodiments does not require (and does not comprise) screening for nucleic acids that encode that encode functional antibodies (e.g., screening the $V_H$ and $V_L$ chains pairs that bind to an antigen).

Various aspects of the embodiments concern identifying a repertoire $V_H$ chains, $V_L$ chains or antibodies. For example, in certain aspects, a method comprises identifying at least 5, 10, 15 or 20 distinct antibody chains or antibodies in a repertoire. For example, a method of the embodiments can comprise identifying 20, 40, 60, 80 or 100 to 250 $V_H$ chains, $V_L$ chains or antibodies in a repertoire. In some aspects, a method comprises identify essentially all of the antibodies (binding to a given antigen) in a subject.

In still a further embodiment, a method is provided for determining antibody $V_H$ or $V_L$ sequences in a subject comprising (a) obtaining nucleic acid, and the corresponding amino acid, sequence information of $V_H$ or $V_L$ gene repertoires of a subject; (b) obtaining mass spectra of peptides derived from serum antibodies of the subject wherein the peptides were obtained by proteolytically cleaving antibodies of the subject and isolating peptides corresponding to the CDRH3 or CDRL3 domain using an antibody that specifically binds to a CDRH3-JH or CDRL3-Jκ,λ sequence; (c) using the sequence information and the mass spectra to determine the amino acid sequence of the $V_H$ or $V_L$ of one or more antibodies in the subject, wherein step (a) or (b) comprises obtaining a sample from the subject. In certain aspects, proteolytically cleaving antibodies comprises digesting the antibodies with a protease enzyme (e.g., trypsin). For example, the protease can be selected using the sequence information from the subject to identify enzymes that cleave antibodies adjacent to the CDR3 region. In certain aspects, an antibody that specifically binds to a CDRH3-JH or CDRL3-Jκ,λ sequence is immobilized on a support (e.g., on a column or a bead).

In yet a further embodiment, an isolated antibody that specifically binds to a CDRH3-JH or CDRL3-Jκ,λ sequence is provided. In certain aspects, the antibody specifically binds to a mammalian CDRH3-J sequence, such as a human sequence. For example, the antibody can specifically bind to a polypeptide comprising a GTLVTVSS (SEQ ID NO: 77), GTMVTVSS (SEQ ID NO: 78), or GTTVTVSS (SEQ ID NO: 79) sequence. In further aspects the antibody can be an avian (e.g., chicken) antibody, such as an IgY antibody.

In still yet a further embodiment, a method is provided for purifying peptides corresponding to an antibody comprising (a) contacting a sample comprising antibody peptides with an antibody that specifically binds to a CDRH3-J or CDRL3-J peptide to generate an immunocomplex; and (b) isolating the immunocomplexes to thereby purify peptides corresponding to an antibody CDRH3 domain. For example, the antibody can specifically bind to a CDRH3-JH or CDRL3-Jκ,λ sequence.

In yet still a further embodiment, there is provided a method for generating an antibody, or antigen-binding fragment thereof, comprising (a) obtaining the sequence of an antibody $V_H$ or $V_L$ sequence that was determined in accordance with the present embodiments; (b) identifying the $V_H$ or $V_L$ binding partner of the sequence of step (a); and (c) generating an antibody or antigen-binding fragment thereof that comprises the $V_H$ and $V_L$ sequences of steps (a) and (b). For example, identifying the $V_H$ or $V_L$ binding partner can comprise coexpression of the sequences and screening for $V_H$ and $V_L$ pairs that exhibit antigen binding. In further aspects, identifying the $V_H$ or $V_L$ binding partner can comprise identifying $V_H$ and $V_L$ pairs in circulation that have similar abundance.

In yet a further embodiment, there is provided a method for generating an antibody $V_H$ or $V_L$ comprising (a) obtaining the sequence of an antibody $V_H$ or $V_L$ sequence that was determined in accordance with the present embodiments; and (b) generating an antibody $V_H$ or $V_L$ comprising the obtained sequence.

In an additional embodiment, there is provided a method for generating antibodies comprising (a) obtaining sequence and abundance information of amino acid sequences of $V_H$ and $V_L$ regions of antibodies in a serum-containing sample of a subject; and (b) generating one or more antibodies that comprise $V_H$ and $V_L$ regions of the serum antibodies based on the sequence and abundance information.

In a certain embodiment, there may also be provided a method for preparing CDR3-containing peptide fragments from antibodies of a subject comprising (a) obtaining nucleic acid, and corresponding amino acid, sequence information of at least the CDR3 of $V_H$ and $V_L$ genes in mature B cells of a subject; (b) using the sequence information to select a protease; and (c) preparing CDR3-containing peptide fragments from serum antibodies of the subject with the protease. Such a protease may predominantly not cleave CDR3 of the $V_H$ and $V_L$ peptides. For example, the protease may cleave at sites adjacent to the CDR3 regions, leaving the CDR3 regions substantially intact.

Certain aspects of the embodiments concern obtaining a sample from a subject. Samples can be directly taken from a subject or can be obtained from a third party. Samples include, but are not limited to, serum, mucosa (e.g., saliva), lymph, urine, stool, and solid tissue samples. Similarly, certain aspects of the embodiments concern biological fluids and antibodies and/or nucleic acids therefrom. For example, the biological fluid can be blood (e.g., serum), cerebrospinal fluid, maternal breast milk, umbilical cord blood, synovial fluid, peritoneal fluid, mucosal secretions, tears, nasal, secretions, saliva, milk, or genitourinary secretions In some aspects, antibody genes for sequencing antibody can be genes in B cells, such as B cells from a selected organ, such as bone marrow. For example, the B cells can be mature B cells, such as bone marrow plasma cells, spleen plasma cells, or lymph node plasma cells, or cells from peripheral blood or a lymphoid organ. In certain aspects, B cells are selected or enriched based on differential expression of cell surface markers (e.g., Blimp-1, CD138, CXCR4, or CD45). In some cases, sequences of a selected class of antibodies are obtained, such as IgG, IgM, IgG, or IgA sequences.

In further aspects, a method of the embodiments may comprise immunizing the subject. The method may further comprise isolation of a lymphoid tissue. The lymphoid tissue isolation may at least or about 1, 2, 3, 4, 5, 6, 6, 8, 9, 10 days or any intermediate ranges after immunization. The method may further comprise obtaining a population of nucleic acids of lymphoid tissue, preferably without separating B cells from the lymphoid tissue. The lymphoid tissue may be a primary, secondary, or tertiary lymphoid tissue, such as bone marrow, spleen, or lymph nodes. The subject may be any animal, such as mammal, fish, amphibian, or bird. The mammal may be human, mouse, primate, rabbit, sheep, or pig.

The nucleic acid pool of antibody variable regions may be a cDNA pool. Obtaining the nucleic acid pool may comprise the use of reverse transcriptase. The method for obtaining the nucleic acid pool, for example, may comprise rapid cDNA end amplification (RACE), PCR amplification, or nucleic acid hybridization. Without separation of B cells from the lymphoid tissue, the nucleic acid population of the lymphoid tissue may contain other non-B-cell nucleic acids as well as non-antibody nucleic acids. For the antibody sequence separation, antibody-specific primers or probes may be used, such as primers or probes based on known antibody constant region cDNA sequences. In alternative aspects, the nucleic acid pool may be a genomic nucleic acid pool.

A method may further comprise determining sequences and occurrence frequency of antibody variable region nucleic acids in the pool. In a further embodiment, the method may comprise identifying abundant variable region sequences. In specific embodiments, the method may further comprise identifying CDR3 sequences of the antibody variable region nucleic acid sequences, such as by homolog searching. Since CDR3 is the most variable region, variable region sequence frequency is preferably based on corresponding CDR3 frequency. Particularly, the occurrence frequency of a selected variable region sequence may be further defined as the sum of the occurrence frequency of any variable region sequences having the same or similar CDR3 sequences as that of the selected variable region sequence. The similar CDR3 sequences may be at least about 90%, 91%, 92%, 93%, 94%, 95%, 96%, 97%, 98%, 99% similar or any intermediate ranges. For example, variable region sequences may be grouped based on the same or similar CDR3 sequences and each group has the same frequency as defined by the sum of the frequency of all the sequences in the same group. In other aspects, the frequency of variable region sequences may be the frequency of each different variable region sequence or based on similarity of full-length variable regions, which contain CDR1, CDR2, and CDR3.

In certain aspects, identification of abundant CDR3 sequences may be performed, followed by identification of full-length variable regions containing the identified abundant CDR3 sequences. For example, primers or probes may be generated based on the abundant CDR3 sequences and used to enrich or amplify antibody variable region sequences encoding the abundant CDR3 sequences.

In exemplary aspects, such abundant sequences may occur in total at a frequency of at least 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5%, 5%, 6%, 7%, 8%, 9%, 10% or any intermediate ranges in the sequences so determined. The abundant variable region sequences so identified may be candidate antigen-specific sequences.

For generation of antigen-specific antibody or antibody fragments, the method may further comprise selecting a pair comprising nucleic acid sequences of a $V_H$ and a $V_L$ at similar abundance levels or a pair comprising nucleic acid sequences that belong to a cluster of nucleic acid sequences comprising similar abundance. For example, the $V_H$ nucleic acid sequence in the pair is the most abundant $V_H$ sequence and the $V_L$ nucleic acid sequence in the pair is the most abundant $V_L$ sequence. Alternatively, the $V_H$ and a $V_L$ at similar abundance levels may be any $V_H$ and a $V_L$ having the same relative rank order in the $V_H$ or $V_L$ subpopulation, respectively, or similar concentration levels. For example, the third most abundant $V_H$ may be paired with the third most abundant $V_L$. In still further aspects, a $V_H$ and/or $V_L$ may be aligned with other identified $V_H$ or $V_L$ sequences to identify clusters of highly homologous sequences (e.g., sequences differing by the results of hypermutation) the clusters are then ranked and the $V_H$ can be paired with a $V_L$ that belongs to a cluster of similar rank.

The method may further comprise generating antibody or antibody fragments comprising amino acid sequences encoded by the paired nucleic acid sequences of $V_H$ and $V_L$. At least one of the generated antibody or antibody fragments may bind the antigen that the subject has been exposed to, such as the immunization agent used to immunize the subject. For example, the abundant variable region sequences may be directly chemically synthesized, such as by an automatic synthesis method. The method may further comprise expressing the abundant variable region sequences (e.g., synthesized) in an in vitro expression system or a heterologous cell expression system.

The subject may be any animal, preferably a mammal or a human. The subject may have a disease or a condition, including a tumor, an infectious disease, or an autoimmune disease, or have been immunized. In certain aspects, the subject may recover or survive from a disease or a condition, such as a tumor, an infectious disease, or an autoimmune disease. In further aspects, the subject may be under or have completed prevention and treatment for a disease or a condition, such as cancer therapy or infection disease therapy, or vaccination. For example, the subject has or has been exposed to an antigen that is an infectious agent, a tumor antigen, a tumor cell, an allergen, or a self-antigen. Such an infectious agent may be any pathogenic viruses, pathogenic bacteria, fungi, protozoa, multicellular parasites, and aberrant proteins, such as prions, as wells as nucleic acids or antigens derived therefrom. An allergen could be any nonparasitic antigen capable of stimulating a type-I hypersensitivity reaction in individuals, such as many common environmental antigens.

A tumor antigen can be any substance produced in tumor cells that triggers an immune response in the host. Any protein produced in a tumor cell that has an abnormal structure due to mutation can act as a tumor antigen. Such abnormal proteins are produced due to mutation of the concerned gene. Mutations of protooncogenes and tumor suppressors that lead to abnormal protein production are the cause of the tumor, and thus such abnormal proteins are called tumor-specific antigens. Examples of tumor-specific antigens include the abnormal products of the ras and p53 genes.

Obtaining the nucleic acid sequence information may comprise determining the nucleic acid sequences and optionally the corresponding amino acid sequences in the B cells or in lymphoid tissues, or in other aspects, obtaining such information from a service provider or a data storage device. In further aspects, such nucleic acid sequence information may be used for determining the amino acid sequences of the serum antibodies.

For determining the nucleic acid sequences (e.g., in the B cells or in lymphoid tissues), any nucleic acid sequencing methods known in the art may be used, including high-throughput DNA sequencing. Non-limiting examples of high-throughput sequencing methods comprise sequencing-by-synthesis (e.g., 454 sequencing), sequencing-by-ligation, sequencing-by-hybridization, single molecule DNA sequencing, multiplex polony sequencing, nanopore sequencing, or a combination thereof.

In certain aspects, there may be provided methods for obtaining sequence information of amino acid sequences of at least the CDR3 of the $V_H$ and $V_L$ regions of antibodies in a biological sample of a subject. Obtaining sequence information may comprise determining amino acid or nucleic acid sequences or obtaining such information from a service provider or a data storage device.

Such amino acid sequence determination methods may comprise obtaining mass spectra of peptides derived from serum antibodies of the subject. To separate peptides derived from serum antibodies, any chromatography methods may be used, such as high-performance liquid chromatography (HPLC).

For determining amino acid sequences, there may be provided methods comprising isolating or enriching a selected class of serum antibodies, such as IgG, IgM, IgA, IgE, or other major Ig classes, isolating or enriching serum antibodies that bind to a predetermined antigen, and/or isolating or enriching CDR3-containing fragments of serum antibodies.

In further aspects, the methods may comprise preparing CDR3-containing peptide fragments from antibodies using a protease that is identified based on the sequence information of nucleic acid sequences and corresponding amino acid sequences of at least the CDR3 of $V_H$ and $V_L$ regions in mature B cells of the subject. For example, the protease cleaves $V_H$ and $V_L$ peptides at the site outside or adjacent to CDR3, thus leaving CDR3 regions substantially intact.

In certain aspects, there may also be provided a method comprising enriching or purifying CDR3-containing peptide fragments. For example, such methods may comprise conjugating CDR3-containing peptide fragments with a labeled thiol-specific conjugating agent for specific conjugation of the unique cysteine at the end of the CDR3 sequences. Methods of enriching or purifying conjugated CDR3-containing peptide fragments may be based on the label on the conjugated CDR3-containing peptide fragments. Examples of the label include biotin.

Certain aspects of the invention are based, in part, on the discovery that highly abundant antibody cDNAs in plasma cells or in a lymphoid tissue are correlated with antibody specificity toward an antigen related to a disease or a condition in the subject, such as a tumor. In additional aspects, there may be provided methods comprising determining the abundance level of the amino acid sequences of the serum antibodies or of the nucleic acid sequences of $V_H$ and $V_L$ genes in the B cells or in a lymphoid tissue, for example, by an automated method. For the determination of abundance level of the amino acid sequences of serum antibodies, a quantitative method for mass spectrometry may be used.

In certain methods, there may be provided methods comprising identifying antibody amino acid sequences that exhibit at least a threshold level of abundance. For example, the threshold level of abundance is a concentration of about, at least, or at most 5, 10, 20, 30, 40, 50, 100, 200, 300, 400, 500 µg/mL (or any range derivable therein) or a level of any one of the about 20, 30, 40, 50, 60, 70, 80, 90, 100, 200 (or any numerical range derivable therein) most abundant CDR3-containing amino acid sequences of the serum antibodies.

In certain methods, there may be provided methods comprising identifying antibody nucleic acid sequences that exhibit at least a threshold level of abundance. Such threshold level of abundance may be at least 0.5%, 1%, 2%, 3%, 4%, 5%, 6%, 7%, 8%, 9%, 10%, or 15% of frequency in an antibody gene pool of the subject, for example, antibody genes in a B-cell population or a lymphoid tissue. Such a B-cell population may be a specific mature B-cell population, such as a population of mature B cells from a selected lymphoid tissue, like bone marrow, spleen, or lymph nodes.

In certain further aspects, there may be provided methods comprising reporting any of the determination or identification described above. For example, such report may be in a computer-accessible format.

In certain aspects, there may also be provided methods comprising generating one or more antibodies or antigen-binding fragments comprising one or more of the amino acid sequences as described above. Generation of antibodies or antigen-binding fragments may comprise chemical synthesis of $V_H$ and $V_L$ coding regions corresponding to abundant $V_H$ and $V_L$ amino acid sequences of serum antibodies that exhibit at least a threshold level of abundance, or comprise, in other aspects, chemical synthesis of abundant nucleic acid sequences of $V_H$ and $V_L$ genes in B cells or in a lymphoid tissue.

For example, the antibodies or antigen-binding fragments so generated may bind an antigen the subject has or has not been exposed to. The antigen may be an infectious agent, a tumor antigen, a tumor cell, or a self-antigen. Such binding may have a monovalent affinity of at least or about 100, 200, $10^3$, $10^4$, $10^5$ pM, or 1, 2, 3, 4, 5 µM or any range derivable therein.

There may be further provided methods comprising evaluating the generated antibody or antigen-binding fragments for binding affinity or specificity to a predetermined antigen, such as an infectious agent, a tumor antigen, a tumor cell, or a self-antigen.

In a preferable aspect, each of the antibodies or antigen-binding fragments so generated comprises similarly abundant amino acid or nucleic acid sequences of $V_H$ and $V_L$. For example, a $V_H$ sequence may have a level of abundance ranked as the $3^{rd}$ most abundant $V_H$ sequence in a serum-containing sample, which may be paired with a $V_L$ sequence that has a similar rank level of abundance (for example, $3^{th}$, $4^{th}$, or $5^{th}$) in the same sample. The inventors determined that pairing $V_H$ genes with $V_L$ genes having a rank-order abundance within +/−3 (e.g., the $3^{rd}$ most abundant $V_H$ with any of the $1^{st}$-$6^{th}$ most abundant $V_L$) results in antigen-specific antibodies at a frequency greater than 50%.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan; however, these terms may be used interchangeably with "comprise" or "comprising," respectively.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features, and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

I. Introduction

Figure 1:
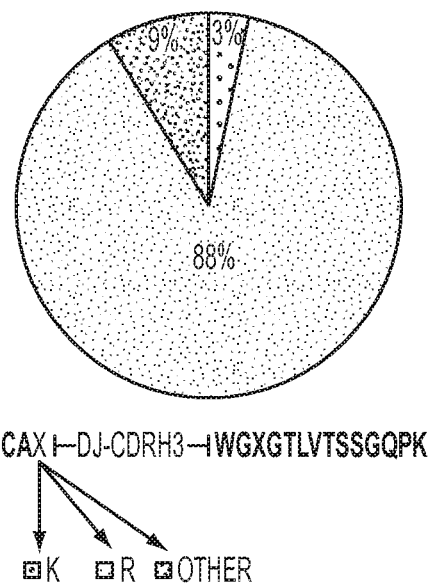
FIG. 1: Occurrences of tryptic sites (K/R) in flanking CDRH3 region. X represents the potential trypsin cleavage site that in 91% of instances exhibits the amino acid R/K (SEQ ID NO:89).

This year marks the 100th anniversary of the first Nobel Prize in Medicine to Emil von Behring who, in collaboration with Kitasato Shibasaburo and also Paul Ehrlich, discovered serum anti-toxins (Browning et al. 1955; Kantha 1991). Remarkably, after 100 years of intense research in immunology, there is practically nothing known about the clonality, relative concentrations, amino acid sequences, and binding properties of the antibodies that comprise the antigen-specific immunoglobulin pool in serum. For both clinical and research purposes, antibody responses are characterized only in terms of the serum titer that is sufficient to detect binding to antigens in ELISAs or other related assays. Being able to determine the clonality of the response, and to sequence, produce, and characterize the antigen-binding affinities of the constituent monoclonal antibodies in serum samples, is of utmost importance for immunology and biomedical research. Such information can provide invaluable insights on the molecular nature of the protective responses following challenge with a pathogen or following vaccination, help the identification of physiologically relevant antibodies, i.e., those present at sufficient concentrations in serum to be important for protection against disease (or alternatively, those that may contribute to a disease state in the case of autoimmunity) and finally, establish the link between the well studied programs for B-cell differentiation with the most important end-point of humoral immunity, namely antibody production.

Several fundamental technical limitations have so far precluded the molecular analysis of serological responses. First, most circulating antibodies are produced by plasma cells, which are terminally differentiated B lymphocytes that are able to survive only in specialized niches within lymphoid organs and thus cannot be readily accessed in living individuals (Radbruch et al., 2006). Second, even in instances where the totality of immunoglobulins expressed by bone marrow plasma cells is interrogated post-mortem using high-throughput DNA sequencing (Reddy et al., 2010), it is immensely challenging to correlate the immune repertoire expressed by plasma cells with the composition of the serum polyclonal pool, since antibodies remain in circulation for many days. Third, proteomic analysis of serum immunoglobulins presents formidable challenges for several reasons: (i) antibody genes are not simply encoded in the germline but are extensively diversified by somatic recombination, revision, and/or mutation, and therefore, the sequence database required for the interpretation of mass spectra is not available a priori (Dekker et al., 2011; de Costa et al., 2010) from genomic data; (ii) because antibodies share a high degree of identity, proteolytic digestion yields numerous non-informative and very similar peptides, producing very complex mass spectra that are difficult to interpret; and (iii) mass spectrometry methods for the de novo sequencing of peptides and their absolute quantification in a complex mixture have not been available until relatively recently (Malmstroem et al., 2009; Olsen et al., 2007).

Aspects of the invention provide methods for the molecular deconvolution of antibody responses in humans and other animals. For example, high-throughput sequencing and proteomic and/or bioinformatic analyses can be combined to identify the sequence and relative abundance of highly represented immunoglobulins (Igs) in circulation or in lymphoid tissues. In certain further embodiments, the genes for the variable domains of these antibodies can then be synthesized, the respective Igs or antibody fragments, such as scFvs, expressed and purified, and then the antibodies or antibody fragments analyzed for binding to an antigen in the source of the subject, such as infectious agents or cancer cells of interest.

In general, molecular deconvolution of antibody response from serum comprises three steps:

(1) high-throughput sequencing (e.g., NextGen sequencing) of portions of V gene cDNAs from a subject. For example, high-throughput sequencing of B lymphocyte cDNAs to generate a database of class-switched antibody variable domain heavy chain ($V_H$) or light chain ($V_L$) sequences in a particular subject;

(2) proteomic analysis of the immunoglobulin fraction from a subject's serum. A protein biochemistry and shot-gun mass spectrometry (MS) proteomic pipeline is used for preparation and sequence assignment of information-rich peptides from which the identity of the corresponding $V_H$ and/or $V_L$ polypeptides can be deduced. In certain aspects it may be preferred that antigen-specific $V_H$ polypeptides are used because the immunoglobulin heavy chain is subject to more extensive sequence diversification than the light chain and plays a far more significant role in antigen recognition for the vast majority of antibodies; and (3) comparison of sequence and proteomic information from steps (1) and (2). Proteomic information obtain is compared to the sequence information to identify (and in some aspects quantify) $V_H$ and/or $V_L$ sequences that are circulating in the subject.

In certain aspects, proteomic analysis of the immunoglobulin of a subject can be focused on the CDRH3 and/or CDRL3 regions of the V domain, which typically display the greatest sequence diversity and are the primary determinants of binding specificity. In these aspects, CDR3-containing peptides are selectively purified prior to proteomic analysis. For example, antibody polypeptides can be fragmented by a protease selected to cleave close to, but not within, the CDR3 domain of the $V_H$ and/or $V_L$. Resulting fragment sequences can then be purified by use of an antibody that binds to the J domain adjacent to the CDR3. After such isolation, proteomic analysis is significantly more efficient, as the amount of "background" peptide has been greatly reduced.

In a further independent aspect, antibody preparations can be treated with two or more Cys-modifying agents prior to proteomic analysis. For example, preparations of antigen-specific F(ab)$_2$ fragments including alkylation (e.g., carboxymethylation) of free Cys residues with two different reagents (e.g., iodoethanol and iodoacetamide) can be analyzed in parallel, followed by proteolytic fragmentation into peptides suitable for quantitative, shot-gun analysis by liquid chromatography-tandem mass spectrometry (LC-MS/MS). The data obtained from these analyses are then compared to identify (and in some embodiments quantify) the sequence of antibodies expressed in the subject. In particular, mis-identified peptides can be revealed when cysteine containing peptides are differentially alkylated (e.g., with either iodoethanol or iodoacetamide), which results in a mass difference. In the case of iodoethanol and iodoacetamide the expected mass difference is 13.00 Da. Peptides with correlated spectra that exhibit a mass difference across treatments but are identified as different peptide sequences are considered misidentifications and removed from analysis. Likewise, peptides that exhibited the mass difference signature should contain a Cys in the identified sequence, and those that did not can thus also be deemed incorrect. Again, removal of non-informative peptides is achieved, which significantly enhances the efficiency of the analysis.

In still a further aspect, proteomic analysis of serum or secretory immunoglobulins can be enhanced by identifying uninformative peptide fragments by determining the average observed masses of peptides that are measured (e.g., by LC-MS/MS) and comparing these values to the expected mass values based on the amino acid sequence. This comparison yields an average mass deviation (AMD). In this case, when the AMD of a peptide is above a certain threshold value, such as about 3 ppm, then the indicated peptide is not informative and not considered in the analysis. Again by sorting the peptide results using peptide AMD analysis, the "background" of the assay can be greatly reduced and the efficiency increased.

Accordingly, entire repertoires of $V_H$ and/or $V_L$ sequences can be determined and quantified for a subject. In certain aspects, identified $V_H$ and/or $V_L$ sequences can then be expressed either individually or in combination. In some embodiments, the relative abundance of $V_H$ and $V_L$ domains can be used to identify antigen-specific antibodies by pairing relevant $V_H$ and $V_L$ chains. Alternatively or additionally, $V_H$ and $V_L$ chains identified by the instant methods can be screened by a combinatorial affinity assay (e.g., ELISA) to identified paired chains.

II. Definitions

Unless defined otherwise, all technical and scientific terms used herein have the meaning commonly understood by one of ordinary skill in the art relevant to the invention. The definitions below supplement those in the art and are directed to the embodiments described in the current application.

The term "antibody" is used herein in the broadest sense and specifically encompasses at least monoclonal antibodies, polyclonal antibodies, multi-specific antibodies (e.g., bispecific antibodies), naturally polyspecific antibodies, chimeric antibodies, humanized antibodies, human antibodies, and antibody fragments. An antibody is a protein comprising one or more polypeptides substantially or partially encoded by immunoglobulin genes or fragments of immunoglobulin genes. The recognized immunoglobulin genes include the kappa, lambda, alpha, gamma, delta, epsilon, and mu constant region genes, as well as myriad immunoglobulin variable region genes.

"Antibody fragments" comprise a portion of an intact antibody, for example, one or more portions of the antigen-binding region thereof. Examples of antibody fragments include Fab, Fab', F(ab')$_2$, and Fv fragments, diabodies, linear antibodies, single-chain antibodies, and multi-specific antibodies formed from intact antibodies and antibody fragments.

"Average mass deviation" or "AMD" refers to a method for analysis of peptide mass spectrometry information. AMD can be determined by comparing the average observed masses of peptides obtained by mass spectrometry to the expected masses based on the amino acid sequence to thereby determine the average difference between obtained and expected peptide masses.

An "intact antibody" is one comprising full-length heavy- and light-chains and an Fc region. An intact antibody is also referred to as a "full-length, heterodimeric" antibody or immunoglobulin.

The term "variable" refers to the portions of the immunoglobulin domains that exhibit variability in their sequence and that are involved in determining the specificity and binding affinity of a particular antibody.

As used herein, "antibody variable domain" refers to a portion of the light and heavy chains of antibody molecules that include amino acid sequences of Complementarity Determining Regions (CDRs; i.e., CDR1, CDR2, and CDR3), and Framework Regions (FRs; i.e., FR1, FR2, FR3, and FR4). FRs include the amino acid positions in an antibody variable domain other than CDR positions as defined herein. $V_H$ refers to the variable domain of the heavy chain. $V_L$ refers to the variable domain of the light chain.

As used herein, the term "complementary nucleotide sequence" refers to a sequence of nucleotides in a single-stranded molecule of DNA or RNA that is sufficiently complementary to that on another single strand to specifically hybridize to it with consequent hydrogen bonding.

An "expression vector" is intended to be any nucleotide molecule used to transport genetic information.

III. Antibody Variable Domains

Certain aspects of the invention provide methods for identifying antibody variable domains or variable domain-coding sequences that are over-represented in serum or B cells. Such skewed representation of antibody variable domains is useful to identify novel antigen-binding molecules having high affinity or specificity. The present invention is based, in part, on the discovery that abundancy levels of regions of an antibody variable domain that form the antigen-binding pocket, for example CDR3 regions, could correlate with the desired affinity specificity or biological function.

For identifying desired antibody variable domains, certain aspects of the present invention provide methods of determining sequences and distributions of antibody complementarity determining regions (CDRs). Specifically, the sequences of one to six of the CDRs on $V_H$ and/or $V_L$ could be determined by MS proteomics and nucleic acid sequencing methods. The level of abundancy of variable domains or CDRs could be determined as an absolute level, like a concentration, or a relative level, like a rank-order.

Antibodies are globular plasma proteins (~150 kDa) that are also known as immunoglobulins. They have sugar chains added to some of their amino acid residues. In other words, antibodies are glycoproteins. The basic functional unit of each antibody is an immunoglobulin (Ig) monomer (containing only one Ig unit); secreted antibodies can also be dimeric with two Ig units as with IgA, tetrameric with four Ig units, like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds. Each chain is composed of structural domains called Ig domains. These domains contain about 70-110 amino acids and are classified into different categories (for example, variable or IgV, and constant or IgC) according to their size and function. They have a characteristic immunoglobulin fold in which two beta sheets create a "sandwich" shape, held together by interactions between conserved cysteines and other charged amino acids.

There are five types of human Ig heavy chain denoted by the Greek letters: α, δ, ε, γ, and μ. The type of heavy chain present defines the class of antibody; these chains are found in IgA, IgD, IgE, IgG, and IgM antibodies, respectively. Distinct heavy chains differ in size and composition; Ig heavy chains α and γ contain approximately 450 amino acids, while μ and ε have approximately 550 amino acids. Other animals encode analogous immunoglobulin heavy chain classes.

Each heavy chain has two regions, the constant region and the variable region. The constant region is identical in all antibodies of the same isotype, but differs in antibodies of different isotypes. Heavy chains γ, α, and δ have a constant region composed of three tandem (in a line) Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B-cell clone. The variable region of each heavy chain is approximately 110 amino acids long and is composed of a single Ig domain.

In humans (and mice) there are two types of immunoglobulin light chain, which are called lambda (λ) and kappa (κ). A light chain has two successive domains: one constant domain and one variable domain. The approximate length of a light chain is 211 to 217 amino acids. Each antibody contains two light chains that are always identical; only one type of light chain, κ or λ, is present per antibody in these species.

The antigen-binding fragment (Fab fragment) is a region on an antibody that binds to antigens. It is composed of one constant and one variable domain of each of the heavy and the light chain. These domains shape the paratope—the antigen-binding site—at the amino terminal end of the monomer.

The two variable domains bind the epitope on their specific antigens. The variable domain is also referred to as the $F_V$ region and is the most important region for binding to antigens. More specifically, variable loops, three each on the light ($V_L$) and heavy ($V_H$) chains, are responsible for binding to the antigen. These loops are referred to as the complementarity determining regions (CDRs).

A complementarity determining region (CDR) is a short amino acid sequence found in the variable domains of antigen receptor (e.g., immunoglobulin and T cell receptor) proteins that complements an antigen and therefore provides the receptor with its specificity for that particular antigen. CDRs are supported within the variable domains by conserved framework regions (FRs).

Each polypeptide chain of an antigen receptor contains three CDRs (CDR1, CDR2, and CDR3). Since the antigen receptors are typically composed of two polypeptide chains, there are six CDRs for each antigen receptor that can come into contact with the antigen (each heavy and light chain contains three CDRs), twelve CDRs on a single antibody molecule, and sixty CDRs on a pentameric IgM molecule. Since most sequence variation associated with immunoglobulins and T cell receptors are found in the CDRs, these regions are sometimes referred to as hypervariable domains. Among these, CDR3 shows the greatest variability as it is encoded by a recombination of the VJ (VDJ in the case of heavy chain) regions.

IV. Antibody Variable Region Analysis

In certain aspects of the invention, antibody variable gene (V gene) sequences derived from cDNA may be analyzed. For example, information from such analysis may be used to generate a database of the V genes (V gene database) that give rise to circulating antibodies so that mass spectrometry (MS) spectra of peptides derived from serum antibodies can be assigned and in turn used to identify the respective full-length V genes in the database encoding those peptides.

In another embodiment, the sequence information may be used to identify abundant variable gene nucleic acids, such as mRNA transcripts, and generate antibody or antibody fragments based on the abundant variable genes. The abundant variable genes so identified may correspond to antibodies or antibody fragments that have desired specificity or affinity.

From the nucleotide sequences determined by the initial sequencing, putative amino acid sequences for the $V_H$ and $V_L$ regions can be determined using standard algorithms and software packages (e.g., see the World Wide Web at mrc-lmb.cam.ac.uk/pubseq/, the Staden package and Gap4 programs). These can be further characterized to determine the CDR (Complementarity Determining Region) parts of the $V_H$ and $V_L$ sequences, particularly CDR1, CDR2, and CDR3. Methods for determining the putative amino acid sequences and identifying CDR regions are well known in the art. In one particular embodiment, CDR3 sequences are identified by searching for a highly conserved sequence motif at the N-terminal region preceding the CDR3. This method could correctly identified >90% of the CDR3 sequences in antibodies. The putative amino acid sequence derived based on the nucleic acid sequencing of B-cell cDNA could be used for the shot gun proteomic analysis of serum antibodies in some embodiments.

A variety of methods have been developed for the immortalization or cloning of antibodies from individual B cells. These techniques include hybridoma technology, memory B-cell immortalization by viral (EBV) infection, the engineering of memory B cells that express both surface and secreted antibodies, and the cloning of antigen-specific, antibody genes from transient ASC populations, from memory B cells, or from splenic plasma cells. Recently, microfluidic and nanopatterning devices have been used to increase the throughput of B cells interrogated for antigen binding and for the subsequent cloning of the $V_H$ and $V_L$ genes.

While invaluable for the isolation of monoclonal antibodies, these techniques have several drawbacks. First, most have focused on and, in some cases, are only compatible with certain stages of the B-cell life cycle. This leaves unresolved the central issue of whether a particular antibody isolated from B cells is represented at a significant amount in the serum of that individual. Also, there is evidence that plasma cells in the bone marrow are the main compartment for antibody synthesis and are selected on the basis of their affinity and perhaps protective function. Second, single B-cell cloning methods are still not efficient enough to provide complete information on the diversity of antibodies in serum, especially with respect to serum concentration and abundancy of specific antibody clones. Third, current attempts to pool recombinant mAbs in order to reconstitute a polyclonal antibody that displays higher therapeutic efficacy cannot possibly capture the true protective effect of sera since the mixing of cloned antibodies is completely ad hoc. The present invention could avoid one or more of these problems by the methods described herein.

In certain embodiments, the mRNA from B cells or directly from one or more lymphoid tissues could be isolated and converted to cDNA. In further embodiments, the cDNA may be subject to $V_H$ and $V_L$ gene isolation. For example, the genes encoding the variable heavy and the variable light ($V_H$ and Vκ,λ) genes could be amplified using specific primers that hybridize to the 5' and 3' ends of the cDNA. Depending on the primers used for cDNA construction, V genes of different Ig classes could be distinguished. For example, the $V_H$ and $V_L$ gene isolation may be based on Ig classes either by using known primer sets of variable gene amplification or, preferably by 5' RACE (rapid amplification of cDNA ends) using a class-specific 3' primer. For example, the class-specific 3' primer may hybridize to the $C_{H2}$ domain.

V. Lymphoid Tissues

In certain embodiments, there may be provided methods of identifying antigen-specific variable region sequences by obtaining nucleic acid sequences directly from lymphoid tissues. In optional aspects, B cells may not be separated from the lymphoid tissue where the B cells reside. The method may comprise isolation of primary, secondary, or tertiary lymphoid tissues. Any methods known for isolation of lymphoid tissues may be used.

Lymphoid tissue associated with the lymphatic system is concerned with immune functions in defending the body against the infections and spread of tumors. It consists of connective tissue with various types of white blood cells enmeshed in it, most numerous being the lymphocytes.

The lymphoid tissue may be primary, secondary, or tertiary depending upon the stage of lymphocyte development and maturation it is involved in. The tertiary lymphoid tissue typically contains far fewer lymphocytes, and assumes an immune role only when challenged with antigens that result in inflammation. It achieves this by importing the lymphocytes from blood and lymph.

The central or primary lymphoid organs generate lymphocytes from immature progenitor cells. The thymus and the bone marrow constitute the primary lymphoid tissues involved in the production and early selection of lymphocytes.

Secondary or peripheral lymphoid organs maintain mature naive lymphocytes and initiate an adaptive immune response. The peripheral lymphoid organs are the sites of lymphocyte activation by antigen. Activation leads to clonal expansion and affinity maturation. Mature lymphocytes recirculate between the blood and the peripheral lymphoid organs until they encounter their specific antigen.

Secondary lymphoid tissue provides the environment for the foreign or altered native molecules (antigens) to interact with the lymphocytes. It is exemplified by the lymph nodes and the lymphoid follicles in tonsils, Peyer's patches, spleen, adenoids, skin, etc. that are associated with the mucosa-associated lymphoid tissue (MALT).

A lymph node is an organized collection of lymphoid tissue, through which the lymph passes on its way to returning to the blood. Lymph nodes are located at intervals along the lymphatic system. Several afferent lymph vessels bring in lymph, which percolates through the substance of the lymph node, and is drained out by an efferent lymph vessel.

The substance of a lymph node consists of lymphoid follicles in the outer portion called the "cortex," which contains the lymphoid follicles, and an inner portion called "medulla," which is surrounded by the cortex on all sides except for a portion known as the "hilum." The hilum presents as a depression on the surface of the lymph node, which makes the otherwise spherical or ovoid lymph node bean-shaped. The efferent lymph vessel directly emerges from the lymph node here. The arteries and veins supplying the lymph node with blood enter and exit through the hilum.

Lymph follicles are a dense collection of lymphocytes, the number, size, and configuration of which change in accordance with the functional state of the lymph node. For example, the follicles expand significantly upon encountering a foreign antigen. The selection of B cells occurs in the germinal center of the lymph nodes.

Lymph nodes are particularly numerous in the mediastinum in the chest, neck, pelvis, axilla (armpit), inguinal (groin) region, and in association with the blood vessels of the intestines.

VI. B Cell Sample Preparation

In certain embodiments, B cells may be extracted for isolation of variable region nucleic acid sequences. In other embodiments, B cells may not need to be separated from a lymphoid tissue, thus saving cost and time for B-cell isolation. Without B-cell separation, lymphoid tissues may be directly used to obtain a pool of antibody variable gene sequences, for example, by using antibody-specific primers or probes, such as primers or probes based on antibody constant region sequences.

In one embodiment, mature, circulating B-cells (memory cells and/or antigen secreting cells (ASCs)) in peripheral blood (for example, about or at least or up to 3, 4, 5, 6, 7, 8, 9, 10, 15, 20 mL or any ranges derivable therefrom) may be used. The circulating B cells may be separated by magnetic sorting protocols (Jackson et al., 2008; Scheid et al., 2009; Smith et al., 2009; Kwakkenbos et al., 2010) as described in the Examples. Alternatively, plasma cells, which are terminally differentiated B cells that reside in the bone marrow, spleen, or in secondary lymphoid organs, could be isolated and used for the determination of the B-cell repertoire in an individual animal or human. In particular aspects, plasma cells could be mobilized from the bone marrow into circulation, e.g., by administration of G-CSF (granulocyte colony-stimulating factor), and isolated.

ASC are terminally or near terminally differentiated B cells (including plasma cells and plasmablasts) that are demarcated by surface markers (for example, syndecan-1). They lack surface IgM and IgD and other typical B-cell surface markers (e.g., CD19) and importantly, they express the repressor Blimp-1, the transcription factor Xbp-1, and down-regulate Pax-5. Antibody secreting cells can be generated from: (i) B1 cells that produce low specificity "innate-like" IgM, (ii) B cells that do not reside in the follicles of lymphoid organs (extrafollicular) and include marginal zone (MZ, $IgM^+$, $IgD^+$, $CD27^+$) cells that generally produce lower affinity antibodies (the latter mostly in the absence T-cell help), and finally, (iii) cells of the B2 lineage that have circulated through the lymphoid follicles. B2 cells progress to the plasma stage either directly from the germinal centers where they undergo selection for higher antigen affinity (following somatic hypermutation) or after they have first entered the memory compartment. Regardless of their precise origin, these cells express high affinity antibodies predominantly of the IgG isotype and constitute the major component of the protective immune response following challenge.

Plasma cells are typically unable to proliferate or de-differentiate back to earlier B-cell lineages. Most plasma cells are short-lived and die within a few days. In contrast, a fraction of the plasma cells occupy "niches" (primarily in bone marrow) that provide an appropriate cytokine microenvironment for survival and continued antibody secretion that may last from months to years; i.e., these are the cells that produce antibodies primarily involved with protection to re-challenge and constitute the "humoral memory" immune response.

A particularly preferred site for ASC isolation is the bone marrow where a large number of plasma cells that express antibodies specific for the antigen are found. It should be noted that B cells that mature to become plasma cells and to reside in the bone marrow predominantly express high affinity IgG antibodies. Mature plasma cells in the bone marrow are selected based on cell surface markers well known in the field, e.g., $CD138^{++}$, $CXCR4^+$, and $CD45^{-/weak}$. Mature plasma cells can also be isolated based on the high expression level of the transcription factor Blimp-1; methods for the isolation of Blimp-1$^{high}$ cells, especially from transgenic animals carrying reporter proteins linked to Blimp-1, are known in the art.

On the other hand, memory B cells are formed from activated B cells that are specific to the antigen encountered during the primary immune response. These cells are able to live for a long time, and can respond quickly following a second exposure to the same antigen. In the wake of first (primary response) infection involving a particular antigen, the responding naïve (ones which have never been exposed to the antigen) cells proliferate to produce a colony of cells, most of which differentiate into plasma cells, also called effector B cells (which produce antibodies), and clear away with the resolution of infection, and the rest persist as the memory cells that can survive for years, or even a lifetime.

VII. Nucleic Acid Sequencing

Any sequencing methods, particularly high-throughput sequencing methods, may be used to determine one or more of the $V_H$ and $V_L$ nucleotide sequences in the B-cell repertoire. For example, the nucleotide sequence of the $V_H$ and $V_L$ could be determined by 454 sequencing (Fox et al., 2009) with a universal primer and without amplification to allow accurate quantitation of the respective mRNAs. Reads longer than 300 bp may be processed for further analysis (Weinstein et al., 2009). Non-limiting examples of high-throughput sequencing technologies are described below.

High-throughput sequencing technologies are intended to lower the cost of DNA sequencing beyond what is possible with standard dye-terminator methods. Most of such sequencing approaches use an in vitro cloning step to amplify individual DNA molecules, because their molecular detection methods are not sensitive enough for single molecule sequencing. Emulsion PCR isolates individual DNA molecules along with primer-coated beads in aqueous droplets within an oil phase. Polymerase chain reaction (PCR) then coats each bead with clonal copies of the DNA molecule followed by immobilization for later sequencing. Emulsion PCR is used in the methods by Marguilis et al. (commercialized by 454 Life Sciences), Shendure and Porreca et al. (also known as "Polony sequencing"), and SOLiD sequencing, (developed by Agencourt, now Applied Biosystems). Another method for in vitro clonal amplification is bridge PCR, where fragments are amplified upon primers attached to a solid surface, used in the Illumina Genome Analyzer. Alternatively, single-molecule methods developed by Stephen Quake's laboratory (later commercialized by Helicos) and by others use bright fluorophores and laser excitation to detect pyrosequencing events from individual DNA molecules fixed to a surface, eliminating the need for molecular amplification.

In parallelized sequencing, DNA molecules are physically bound to a surface, and sequenced in parallel. Sequencing by synthesis, like dye-termination electrophoretic sequencing, uses a DNA polymerase to determine the base sequence. Reversible terminator methods (used by Illumina and Helicos) use reversible versions of dye-terminators, adding one nucleotide at a time and detecting fluorescence at each position in real time by repeated removal of the blocking group to allow polymerization of another nucleotide. Pyrosequencing (used by Roche 454 and others) also uses DNA polymerization, adding one nucleotide species at a time and detecting and quantifying the number of nucleotides added to a given location through the light emitted by the release of attached pyrophosphates.

Sequencing by ligation uses a DNA ligase to determine the target sequence. Used in the polony method and in the SOLiD technology, it uses a pool of all possible oligonucleotides of a fixed length, labeled according to the sequenced position. Oligonucleotides are annealed and ligated; the preferential ligation by DNA ligase for matching sequences results in a signal informative of the nucleotide at that position.

In microfluidic Sanger sequencing the entire thermocycling amplification of DNA fragments, as well as their separation by electrophoresis, is done on a single glass wafer (approximately 10 cm in diameter) thus reducing the reagent usage as well as cost.

Sequencing by hybridization is a non-enzymatic method that uses a DNA microarray. A single pool of DNA whose sequence is to be determined is fluorescently labeled and hybridized to an array containing known sequences. Strong hybridization signals from a given spot on the array identify the sequence of the DNA. Mass spectrometry may be used to determine mass differences between DNA fragments produced in chain-termination reactions.

DNA sequencing methods currently under development include labeling the DNA polymerase (Scheid et al., 2009), reading the sequence as a DNA strand transits through nanopores, and microscopy-based techniques, such as atomic force microscopy (AFM) or electron microscopy that are used to identify the positions of individual nucleotides within long DNA fragments (>5,000 bp) by nucleotide labeling with heavier elements (e.g., halogens) for visual detection and recording.

The inventors found that less than $10^5$ reads for each of the $V_H$ and $V_L$ pools could be sufficient to provide information on the variable gene sequences that correspond to the most abundant antibodies found in serum.

VIII. Sequence Abundancy Determination

Bioinformatic methods for the automated analysis of sequencing results, such as 454 reads, statistical sequencing error analysis, and finally identification and classification of CDRs, especially of CDR3, the most hypervariable region in antibodies, have been developed by the inventors.

In certain embodiments, for example, to account for sequencing/PCR uncertainties, antibody sequences, particularly CDR3 sequences, could be grouped into families, with each family consisting of all the CDR3 sequences differing by one or two nucleotides or amino acids.

For example, the abundancy level of antibody variable region sequences may be based on the CDR3 sequences as identifiers. The sequences for determination of a level of abundancy may be a family, including an identical CDR3 sequence (amino acid sequence or nucleic acid sequence) and a CDR3 sequence having at least 80% homology, for example 85%, 90%, 95%, 96%, 97%, 98%, or 99% homology therewith. Sequence homology is as determined using the BLAST2 program (Tatusova et al., 1999) at the National Center for Biotechnology Information, USA (World Wide Web at ncbi.nlm.nih.gov) with default parameters. For example, the sequences occurring in total at a relative level of abundancy represented by a frequency at least 1 percent in the set of sequences may be a combination of the CDR3 sequences or a sequence having 1 or 2 amino acid changes therefrom. For example, a first sequence may occur at a frequency of 0.7 percent, and second, third, and fourth sequences each having a single amino acid change therefrom each occur at a frequency of 0.1%—the total occurrence in abundancy is therefore 1.1% and the dominant antibody sequence (occurring at a frequency of 0.7%) is therefore a candidate CDR3 sequence that could be used for antibody generation/characterization.

IX. Use of Antibody Variable Sequence Information

In addition to providing a reference database for interpreting mass spectra data of serum antibody analysis, the nucleic acid information through analysis of the variable region, especially CDR, sequence and abundancy could also be used to provide potential antigen-specific antibody or antibody fragments. In certain aspects, the resulting $V_H$ and Vκ, λ libraries based on the abundant variable region especially CDR information could be inserted into an appropriate expression vector suitable for the production of either full-length IgG proteins or of antibody fragments (scFv or Fab or single domain antibodies comprised of only the $V_H$ or the Vκ, λ chain). Libraries comprising $V_H$ and Vκ, λ could result in combinatorial pairing of the heavy and light chains.

Some of the randomly paired $V_H$ and Vκ, λ chains may be active while others will not give rise to functional antibodies. However, the inventors have found that, because of the very high representation of antigen-specific plasma cells in bone marrow, a large fraction of the resulting clones following challenge with an immunogen or pathogen express functional and high affinity recombinant antibodies. In one example, in a scFv library constructed from $V_H$ and Vκ, λ genes isolated from bone marrow plasma cells, >5% of the clones contained antigen-specific antibodies.

For example, the inventors analyzed $V_H$ and $V_L$ transcript levels in bone marrow plasma cells isolated five days after booster immunization (incomplete Freund's adjuvant) with four different protein antigens in two mice each. Patterns of V-D-J usage and somatic hypermutation were determined and correlated with representation within the bone marrow plasma cell population. Consistent with the pivotal role of bone marrow plasma cells on antibody secretion, antigen-specific $V_H$ and $V_L$ cDNA levels were found to be highly enriched to between 1% and 20% of the total Ig RNA. For each of the four antigens tested, 2-4 $V_H$ and $V_L$ cDNAs were represented at frequencies >4% of the total $V_H$ cDNA pool. The four most abundant $V_H$ and $V_L$ genes for each antigen and from each mouse were synthesized, the heavy and light chains paired as discussed below, and the resulting antibody fragments were expressed in bacteria. Importantly, on average, >80% of the antibody fragments corresponding to the most highly expressed $V_H$ and $V_L$ genes in the immunized animals were found to be antigen-specific by ELISA (enzyme-linked immunosorbent assay) and BIACore analysis.

Thus, the inventors have found that manual ELISA screening of a few hundred clones from such libraries is sufficient to allow the generation of antibodies with high affinity and specificity. Manual ELISA screening of additional clones can be used to reveal different combinations of $V_H$ and Vκ, λ genes that give rise to a diverse set of antibodies. This method is simple and fast, and the inventors believe that it is likely to replace the hybridoma technology for the isolation of antibodies from animals.

X. Quantitative Serum Antibody Analysis

To identify a pool of abundant amino acid sequences of CDR regions, especially CDR3 regions of circulating antibodies, MS shotgun proteomics or protein sequencing methods may be used to determine the amino acid sequences.

Any protein sequencing methods determining the amino acid sequences of its constituent peptides may be used. The two major direct methods of protein sequencing are mass spectrometry and the Edman degradation reaction. It is also possible to generate an amino acid sequence from the DNA or mRNA sequence encoding the protein, if this is known. However, there are also a number of other reactions that can be used to gain more limited information about protein sequences and can be used as preliminaries to the aforementioned methods of sequencing or to overcome specific inadequacies within them.

For example, a shotgun proteomic strategy based on digesting proteins into peptides and sequencing them using tandem mass spectrometry and automated database searching could be the method of choice for identifying serum antibody sequences. "Shotgun proteomics" refers to the direct analysis of complex protein mixtures to rapidly generate a global profile of the protein complement within the mixture. This approach has been facilitated by the use of multidimensional protein identification technology (MudPIT), which incorporates multidimensional high-pressure liquid chromatography (LC/LC), tandem mass spectrometry (MS/MS), and database-searching algorithms.

A. IgG Fractionation

Ig proteins of a particular class could be isolated, for example, by affinity chromatography using protein A (or anti-IgA and anti-IgM antibodies for affinity purification of the other major Ig classes).

In certain aspects, antibodies or antibody fragments, such as Fab fractions from digestion of purified Igs with papain and Fab purification, could be affinity enriched for binding to desired antigen or pathogen (e.g., a cancer cell, a tumor antigen, or an infection agent), or host tissue for the isolation of antibodies suspected to have a role in autoimmunity. Antibodies may be eluted under denaturing conditions. In further embodiments, several fractions or pools of serum-derived Fabs could be generated, including those that are: (a) enriched for antigen, (b) enriched for host tissue, and (c) antibodies with unrelated or unknown specificities.

B. Proteolytic Fragmentation

For quantitative shotgun proteomics mass spectrometry analysis, antibodies or antibody fragments, such as Fab, could be digested using proteases that cleave after amino acids/amino acid pairs that are under-represented in CDR3 but present in the adjacent framework regions. The appropriate proteases for proteomic processing may be identified by bioinformatic analysis of the V gene sequence database.

In one example, the Fab fractions are subjected to proteolysis with proteomics grade trypsin (Sigma) at 37° C. for 4 h. As an alternate method, a combination of other proteases, such as GluC (NEB) and LysC (Sigma), could be used in place of trypsin to generate a distinct set of proteolytic peptides that in computational tests provide better coverage of the CDR3s (i.e., so that cleavage occurs at positions flanking the CDR3s and therefore peptides with intact CDR3s are produced).

In certain embodiments, CDR3 peptides could be enriched from unrelated peptides via specific conjugation of the unique Cys at the end of the CDR3 sequence with a thiol-specific reagent that allows the purification of such peptides.

The inventors have developed protocols that deploy a combination of appropriate proteases for peptide generation and Cys-specific pull down of thiol-containing CDR3 peptides that result in a peptide mixture comprising of at least 30% CDR3 peptide sequences. In one example, CDR3 peptides are enriched via reversible thiol-specific biotinylation. In another example, CDR3 peptides are reacted with special chromophores that allow their specific excitation and detection during MS analysis. Using appropriate proteases, CDR3 peptides almost universally (>99%) containing cysteine can be generated and, a biotinylated thiol-specific cross-linking agent is then used to affinity isolate these peptides for mass spectral analysis thus greatly simplifying the complexity of the spectra.

C. Shotgun MS (Mass Spectrometry) Proteomics

In certain exemplary aspects, the peptides of antibody molecules could be resolved by reverse phase chromatography and in-line nanoelectrospray ionization/high-resolution tandem mass spectrometry, using well-established protocols (Ong and Mann, 2005; Pandey and Mann, 2000; Shevchenko et al., 1996; Hunt et al., 1986; Link et al., 1999; Washburn et al., 2001; Lu et al., 2007) and Fourier-transform LTQ-Orbitrap mass spectrometry (Hu et al., 2005) to collect hundreds of thousands of tandem mass spectra from CDR3 and other Fab-derived peptides.

For example, peptides were separated on a reverse phase Dionex Acclaim C-18 column (Thermo Scientific) running an elution gradient from 5% to 38% acetonitrile, 0.1% formic acid. Peptides were eluted directly into an Orbitrap Velos mass spectrometer (Thermo Scientific) by nano-electrospray ionization. Data-dependant ion selection could be enabled, with parent ion mass spectra (MS1) collected at 100 k resolution. Ions with known charge >+1 may be selected for CID fragmentation spectral analysis (MS2), with a maximum of 20 parent ions selected per MS1 cycle. Dynamic exclusion is activated for 45 seconds with ions selected for MS2 twice within 30 sec. Ions identified in an LC-MS/MS run as corresponding to peptides from the constant regions of the heavy and light chains may be excluded from data-dependent selection in subsequent experiments in order to increase selection of peptides from the variable region.

D. MS Proteomic Data Analysis

The variable gene sequencing data from B cells of the same subject are employed to supplement the protein sequence database for interpreting peptide mass spectra in shotgun proteolysis (Marcotte, 2007). With the aid of the sample-specific sequence database, CDR3 peptides were identified from the tandem mass spectra controlling for false discovery rate using standard methods (Keller et al., 2002; Nesvizhskii et al., 2009).

Several recent advances in shotgun proteomics enable protein quantification to ~2-fold absolute accuracy without introducing additional requirements for isotope labels or internal calibrant peptides (Lu et al., 2007; Malmstrom et al., 2009; Silva et al., 2006a; Vogel and Marcotte, 2008; Ishihama et al., 2005; Liu et al., 2004). Among these approaches, two are well-suited to quantification of individual IgGs: the APEX approach is based upon weighted counts of tandem mass spectra affiliated with a protein (the weighting incorporates machine learning estimates of peptide observability (Lu et al., 2007; Vogel, 2008), and the average ion intensity approach is based on mass spectrometry ion chromatogram peak volumes (Silva et al., 2006a).

For example, both methods could be employed to measure abundances of each of the identified antigen-specific IgGs in the serum-containing sample. Combinations (Malmstrom et al., 2009) and single peptide quantitation methods could also be used as alternatives. Algorithms for subtraction of non-CDR3 peptides could be used. On the basis of these measured abundances, at least the 50 or 100 most highly abundant $V_H$ and $V_L$ proteins in the sample could be rank-ordered.

For example, sample-specific protein sequence databases are created from high-throughput V region cDNA transcript data. VH and VL genes represented by >2 reads by 454 sequencing are compiled into a database that in turn is added to a database of all known protein-coding sequences for the subject organism, as well as a database containing common sample contaminants. The LC-MS/MS data is searched against this database using the Sequest search algorithm as part of the Proteome Discoverer software package (Thermo Scientific). The confidence of peptide identifications is determined using the Percolator algorithm in Proteome Discoverer (Thermo Scientific). In certain embodiments, the amino acid sequence analysis coupled with the nucleic acid information from various V gene pools of different B-cell sources (e.g., the particular organ-specific ASC population that expresses $V_H$ and $V_L$ genes whose products are found in serum) could be employed to identify whether a particular serum antibody originated preferentially in the bone marrow, in secondary lymphoid tissues (as is likely to be the case early in the immune response), or in the case of persistent infection, possibly in tertiary lymphoid tissues. The possibility that a particular antibody is secreted by plasma cells that have migrated to different tissues could also be addressed. At a systems level, the inventors could employ this information to estimate the contribution of different compartments to humoral immunity in a quantitative fashion and could generate antibody or antibody fragments involved in different stages of the immune response.

XI. Antibody Generation and Characterization

Certain embodiments described above lead to the identification and quantitation of abundant serum antibodies of interest or the most abundant variable region sequences in B cells or in a selected lymphoid tissue. Such information may be used to develop antibody or antibody fragments that have desired binding affinity or antigen response. In certain aspects, their binding specificities or therapeutic utility could be evaluated. For example, antibody or antibody fragments that are cytotoxic towards cancer cells could be generated from the abundant serum polyclonal antibody pool. In further embodiments, antibody or antibody-specific fragments that are specific for the antigen used to immunize any animal may be provided by analyzing sequence and abundance information of variable region nucleic acids in B cells or directly from lymphoid tissues.

A. Gene Synthesis for Antibody Generation

To generate antibody or antibody fragments with the desired binding specificity, the V genes could be synthesized, assembled into Fab or IgG, and expressed. $V_H$ and $V_L$ genes may be generated by high-throughout gene synthesis based on the sequence information obtained by the methods described above.

For example, automated gene synthesis could be used. Briefly, gene fragments (lengths from 200 to 500 nucleotides) are generated using inside-out nucleation PCR reactions under carefully controlled conditions to ensure construction of the desired final fragment. Subsequently stitchoverlap extension PCR is used to synthesize the gene of interest. The design of these fragments and relevant overlaps is automated, with oligonucleotide synthesizer worklists and robot operation scripts for synthesis and assembly. Alignment of sequences so as to maintain maximal conservation and subsequent "padding" of the sequences at either end to maintain identical length permits the use of a generic overlapping oligonucleotide assembly strategy and also ensures the most oligonucleotide re-use. Currently throughput stands at 50 $V_H$ and 50 $V_L$ genes (i.e., >38,000 bp of DNA) synthesized and validated for correct ORF by one researcher within a week and at a reagent cost <$2,000.

B. Pairing of $V_H$ and $V_L$

For expression, a particular $V_H$ has to be paired with cognate $V_L$. The pairing problem could be addressed as follows: First, the inventors have empirically found that the correct pairings of $V_H$ and $V_L$s in a sample correlate well with the rank-ordered abundancy of the proteins in the sample. For example, the fifth most abundant $V_H$ pairs with the fifth most abundant $V_L$. So far with this approach, using $V_H$ and $V_L$ bioinformatic rank-ordering information for pairing, the inventors have achieved 75% success in pairing $V_H$ and $V_L$ genes to produce high affinity antigen-specific antibodies from four different mice. Further, the inventors have found that even if the optimal VL for pairing is not the one having similar abundancy based on proteomic analysis and because antigen recognition is dominated by the $V_H$ sequence, antigen binding could be still observed, albeit with lower affinity.

In certain aspects, $V_H$ and $V_L$ chains can be identified by grouping together related $V_H$ and $V_L$ sequences. For example, identified $V_H$ and/or $V_L$ sequences can be aligned and clustered base on the relatedness of the sequences. For example, each group may comprise antibody sequences that differ from each other only by the result of somatic hypermutation. In some cases, clusters of sequences can be ranked and the rank of the clusters used to guide paring between $V_H$ and $V_L$ sequences.

In still further aspects, $V_H$ and $V_L$ chains can be paired based on combinatorial library screening where one V gene is synthesized and the second V gene that comprises a functional antibody is obtained via the screening of a combinatorial library comprising said synthetic V gene paired with cDNA encoding all V genes in an individual. In this case, $V_H$ and $V_L$ pairs for testing can be guided by abundance ranking and/or by clustering of related sequences as outlined above.

The pairing could also be addressed or confirmed by other approaches. For example, in situ hybridization (ISH) of fixed plasma cells with $V_H$ and candidate $V_L$ probes, for example, identified from the abundancy analysis. ISH can easily be applied in a high-throughput manner using appropriate robotic automation. Alternatively, ESI-MS (electrospray ionization mass spectrometry) of the FAB pool, coupled with matching of these spectra to the expected molecular weight, can in certain cases determine $V_H$ and $V_L$ pairing.

C. Antibody Expression

In further aspects, the synthesized $V_H$ and $V_L$ genes may be inserted into appropriate vectors for expression, for example, as Fabs in *E. coli* or as full-length IgGs in *E. coli* or by transient transfection of HEK293 cells.

Binding between candidate antibody or antibody fragments and antigen could then be evaluated by any methods for binding detection and quantification, particularly ELISA. For example, cancer-specific antibodies or antibody fragments could be characterized by cancer and host cell binding by fluorescence-activated cell sorting (FACS) following fluorescent labeling of antibodies.

Antibodies, according to certain aspects of the invention, may be labeled with a detectable label or may be conjugated with an effector molecule, for example, a drug, e.g., an antibacterial agent or a toxin or an enzyme, using conventional procedures, and the invention extends to such labeled antibodies or antibody conjugates.

Antibodies usable or produced in the present invention may be a whole antibody or an antigen-binding fragment thereof and may in general belong to any immunoglobulin class. Thus, for example, it may be an IgM or an IgG antibody. The antibody or fragment may be of animal, for example, mammalian origin and may be, for example, of murine, rat, sheep, or human origin. Preferably, it may be a recombinant antibody fragment, i.e., an antibody or antibody fragment that has been produced using recombinant DNA techniques. Such recombination antibody fragments may comprise prevalent CDR or variable domain sequences identified as above.

Particular recombinant antibodies or antibody fragments include (1) those having an antigen binding site at least part of which is derived from a different antibody, for example, those in which the hypervariable or complementarity determining regions of one antibody have been grafted into the variable framework regions of a second, different antibody (as described in, for example, EP 239400); (2) recombinant antibodies or fragments wherein non-Fv sequences have been substituted by non-Fv sequences from other, different antibodies (as described in, for example, EP 171496, EP 173494, and EP 194276); or (3) recombinant antibodies or fragments possessing substantially the structure of a natural immunoglobulin but wherein the hinge region has a different number of cysteine residues from that found in the natural immunoglobulin but wherein one or more cysteine residues in a surface pocket of the recombinant antibody or fragment is in the place of another amino acid residue present in the natural immunoglobulin (as described in, for example, WO 89/01782 and WO 89/01974).

Teachings of texts, such as Harlow and Lane (1998), further detail antibodies, antibody fragments, their preparation, and use.

The antibody or antibody fragment may be of polyclonal or monoclonal origin. It may be specific for at least one epitope.

Antigen-binding antibody fragments include, for example, fragments derived by proteolytic cleavage of a whole antibody, such as F(ab')2, Fab', or Fab fragments, or fragments obtained by recombinant DNA techniques, for example, Fv fragments (as described, for example, in WO 89/02465).

XII. Therapeutic Applications

The present invention may involve methods that have a wide range of therapeutic applications, such as cancer therapy, enhancing immune response, vaccination, or treatment of infectious disease or autoimmune diseases.

In some embodiments, the present methods may be used for the quantitative molecular deconvolution of antibody response in cancer patients in remission to identify the sequence and abundancy of the highly represented antibodies in circulation that may contribute to the eradication of the tumor in the patient. Such antibodies could be very useful as therapeutic agents on their own or for the identification of new antigens on cancer cells that can serve as therapeutic targets. Similarly in some embodiments the present methods can be used to identify antibodies that can protect patients from a particular infectious agent. Such antibodies may be identified either from patients that had been infected and then recovered from the infection or alternatively, from vaccinated patients. These antibodies or antibody fragments could be produced and their specificity and cytotoxicity toward cancer cells or neutralization potency towards infectious agents could be evaluated. The ability to deconvolute the serum polyclonal response by characterizing the relative abundancy and amino acid sequences of its antibody components and then to individually evaluate cancer cell binding and cytotoxicity could provide an unprecedented wealth of information on the nature of adaptive immune responses to malignancies. Such identified antibodies could lead to the discovery of potent cytotoxic cancer therapeutics and the identification of novel tumor antigens used for cancer detection and therapy.

For example, therapeutic antibodies for leukemia, via the deconvolution of antibody responses in patients in remission following allogeneic hematopoietic stem cell (HSC) transplantation, could be identified by the methods described above. Promising antibodies could then be taken through pharmacological engineering and animal evaluation.

Certain aspects of the present invention may involve the passive transfer of antibody or antibody fragments generated by certain aspects of the present invention to non-immune individuals (e.g., patients undergoing chemo/radio therapy, immunosuppression for organ transplantation, patients immunocompromised due to underlying conditions, such as diabetes, trauma etc, and the very young or very old). For example, the sequences of antibodies conferring immunity can be determined by looking for over-represented $V_H$ and $V_L$ sequences in patients who have overcome infection. These protective antibodies can be re-synthesised at the genetic level, over-expressed in $E.$ $coli$ (or other expression systems) and purified. The resultant purified recombinant antibody can then be administered to patients as a passive immunotherapy. Antibodies can also be ordered from commercial suppliers, such as Operon Technologies Inc., USA (on the World Wide Web at operon.com), by simply supplying them with the sequence of the antibody to be manufactured.

Vaccination protects against infection by priming the immune system with pathogen-derived antigen(s). Vaccination is effected by a single or repeated exposure to the pathogen-derived antigen(s) and allows antibody maturation and B-cell clonal expansion without the deleterious effects of the full-blown infectious process. T cell involvement is also of great importance in effecting vaccination of patients. Certain aspects of the present invention can also be used to monitor the immunization process with experimental vaccines along with qualitative and quantitative assessment of antibody response. For example, one or more subjects are given the experimental vaccine, $V_H$ and $V_L$ sequences are amplified from the subjects, and the serum antibodies that are specific for the immunogen and the V antibody repertoires in the vaccines are analyzed as described above. The respective antibodies can be produced in viro and their neutralization potency and breadth can be determined. Knowing the clonality and time course of the change in the concentration of monoclonal antibodies that comprise the polyclonal response can be of great significance for evaluating vaccine efficacy.

XIII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Processing of Serum Antibodies from an Immunized Rabbit for Mass Spectrometry Analysis High titer immunized mammal serum (2.5 mL, e.g., $Concholepas$ $concholepas$ hemocyanin (CCH), Pierce, Ill.) was diluted 4-fold in PBS and IgG proteins were purified by affinity chromatography using a protein A agarose (Pierce, Ill.) column in gravity mode. Diluted serum was recycled six times through the protein A affinity column and then the column was washed with PBS followed by elution of IgG using 100 mM glycine, pH 2.7.

Approximately 10 mg of protein A-purified serum IgG was digested with pepsin to produce $F(ab)_2$ fragments using 500 µL of immobilized pepsin agarose (Pierce, Ill.) in 20 mM sodium acetate, pH 4.5, and digestion was allowed to proceed for seven hours, shaking vigorously at 37° C. The degree of digestion was evaluated by non-reducing 4%-20% SDS-PAGE (FIG. 1).

Affinity chromatography for the isolation of antigen-specific IgG-derived $F(ab)_2$ was carried out by coupling the 100 mg antigen, CCH, onto 1 g of dry N-hydroxysuccinimide (NHS)-activated agarose (Pierce, Ill.) by overnight incubation at 4° C. The coupled agarose beads were washed with PBS and unreacted NHS groups were blocked with 1 M ethanolamine, pH 8.3 for 60 min at room temperature, washed with PBS, and packed into a chromatography column. IgG $F(ab)_2$ fragments were applied to the antigen affinity column in gravity mode, with the flow-through collected and reapplied to the column five times. The column was subsequently washed with PBS and eluted using 100 mM glycine, pH 2.7.

Protein fractions from the antigen affinity chromatography flow through, wash buffer, and elution were L-Cys alkylated with 2-iodoethanol and then digested with trypsin in the presence of urea. Specifically, protein was first denatured in 8 M urea. The denatured protein was then dissolved in a solution containing (final concentrations): 2.4 M urea, 200 mM ammonium carbonate, pH 11.0, 48.75% v/v acetonitrile, 65 mM iodoethanol as the Cys alkylating agent, and 8.5 mM triethylphosphine as the reducing agent. The final pH of the solution was adjusted to 10 and then it was incubated at 37° C. for 60 min. To avoid urea carbamylation, urea solutions were made freshly and deionized on AG-5Ol-X8 resin (Biorad, CA) just before use. Samples were dewatered using a Speedvac® and resuspended in 100 mM Tris-HCl, pH 8.5 to reach a final urea concentration of 1.6 M prior to trypsin digestion. Trypsin digestion was carried out by adding trypsin at a ratio of 1:75 trypsin:protein and incubating at 37° C. for five hours. Lowering the pH with 1% v/v formic acid was employed to deactivate the trypsin.

For differential L-Cys labeling, protein fractions from the antigen affinity chromatography flow through, wash buffer, and elution were separately alkylated with iodoacetamide and then digested with trypsin in the presence of 2,2,2-trifluoroethanol (TFE, Sigma). Specifically, protein fractions following antigen affinity chromatography were mixed with reaction solution that consisted of (final concentrations): 50% v/v TFE, 50 mM ammonium bicarbonate, and 10 mM DTT at 55° C. for 60 min. TFE denatured, reduced F(ab')$_2$ were then L-Cys alkylated by incubation with 32 mM iodoacetamide (Sigma, MO) for one hour at room temperature and then the alkylation reaction was quenched by addition of 7.7 mM DTT for one hour at room temperature. Samples were diluted with water to reach a final TFE concentration of 5% v/v. Trypsin digestion was carried out by adding trypsin at a ratio of 1:75 trypsin:protein and incubating at 37° C. for 5 hours. Lowering the pH with 1% v/v formic acid was employed to deactivate the trypsin.

Peptides derived from differential labeling of cysteine residues with either iodoacetamide or iodoethanol followed by proteolytic digestion were subject to chromatographic separation on a C18 reverse phase column using an acetonitrile elution gradient. Peptides were eluted onto an LTQ Orbitrap™ Velos mass spectrometer (Thermo Scientific) using a Nano-spray source. The LTQ Orbitrap Velos was operated in the data dependent mode with scans collected at 60,000 resolution. Ions with charge >+1 were selected for fragmentation by collision-induced dissociation (CID) with a maximum of 20 fragmentation scans per full scan, or alternatively by higher energy collision dissociation (HCD) with a maximum of 10 fragmentation scans per full scan.

Example 2: Detection of MS Peptide Mis-Identification by Exploiting Differential L-Cys Labeling The resulting spectra from Example 1 were searched against a protein sequence database consisting of a rabbit full protein-coding sequence database (OryCun2) and common contaminant proteins combined with in-house rabbit $V_H$ and $V_L$ sequences, using SEQUEST® and Percolator (Proteome Discoverer 1.2, Thermo Scientific) to generate a high-confidence dataset of top-ranked protein-spectrum matches (PSMs) at <1% FDR as determined by Percolator. Only $V_H$ and $V_L$ sequences with ≥2 reads were included in the search. The search specified tryptic peptides with up to two missed tryptic cleavages allowed. A precursor mass tolerance of 5 ppm was used, with fragment mass tolerance set to 0.5 Da for spectra generated by CID and 0.02 Da for spectra generated by HCD. Static cysteine modifications of either carbamidomethylation (iodoacetamide, +57.021) or ethanolyl (iodoethanol, +44.026) were included based on which modifying reagent was used. Oxidized methionine was allowed as a dynamic modification.

Figure 6:
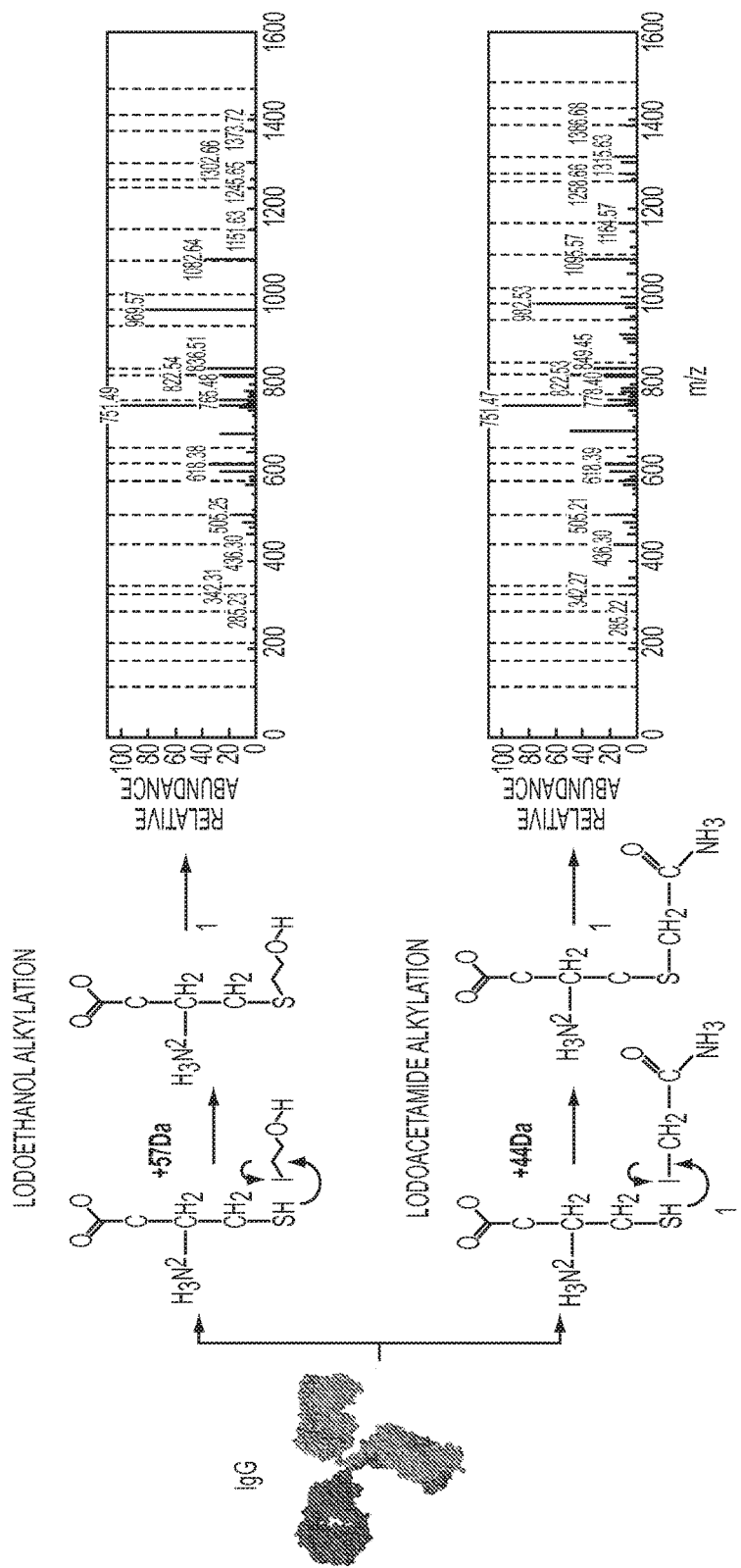
FIG. 6: Schematic shows an example cysteine alkylation of the embodiments and resulting mass spectra obtained from differentially alkylated peptides.
Figure 7A:
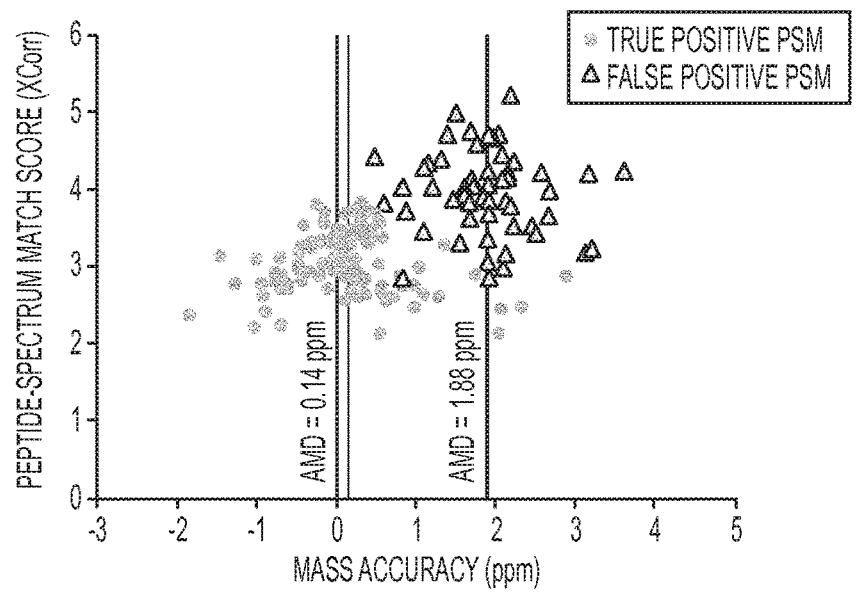
FIG. 7A-7B: 7A, plot shows the observed protein-spectrum match scores for peptides analyzed by mass spectrometry. Grey line indicates the average mass accuracy for "true positive" results. Black line indicates the average mass accuracy for "false positive" results. 7B, plot shows the density of spectra vs. AMD for all peptides, "true positives" and "false positives. True positives show a clustered density below 1 ppm AMD, while false positives show a density that only slightly decreases across the entire range of AMD depicted.
Figure 7B:
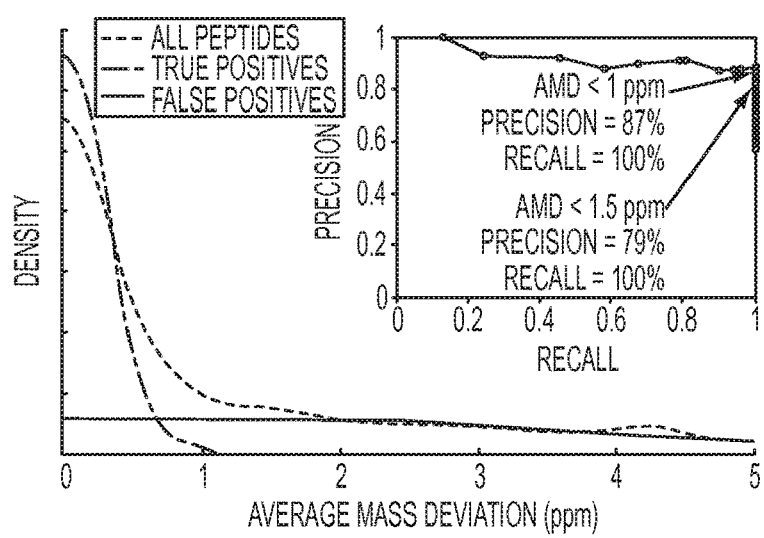

Following SEQUEST® sequence assignment, identified peptides were subject to further analysis to determine their consistency with secondary sequence information derived from differential cysteine labeling. The monoisotopic difference in mass between the iodoacetamide modification (carbamidomethyl) and iodoethanol modification (ethanolyl) is 12.995 Da. Thus, parent ions of peptides containing a cysteine residue would exhibit a shift corresponding to ~13.00 Da between the differentially labeled samples (FIG. 6). Pairs of parent ions exhibiting this mass difference between samples, and exhibiting similar relative elution profiles were flagged as putative cysteine-containing peptides. Corresponding fragmentation spectra from differentially-labeled ions of flagged peptides were compared for consistency to confirm that the spectra were derived from the same parent peptide. Spectral pairs identified as the same peptide (inherently requiring the presence of a cysteine to match) were flagged as a "true positives", while parent ions exhibiting a confirmed 13 Da mass shift butan assigned peptide sequence lacking cysteine residues were deemed "false positives" (Table 1).

TABLE 1

Confirmation of peptide sequence by mass shift following differential cysteine labeling.

| Peptide Sequence | Iodoethanol | Iodoacetamide | Δ Mass |
|---|---|---|---|
| Correct Identifications | | | |
| NVAGYLCAPAFNFR (SEQ ID NO: 1) | 1586.7791 | 1599.7743 | 12.9952 |
| VCGMDLWGPGTLVTVSSGQPK (SEQ DI NO: 2) | 2176.0789 | 2189.0745 | 12.9956 |
| ETGGGLVQPGGSLTLSCK (SEQ DI NO: 3) | 1747.8899 | 1760.8851 | 12.9953 |
| MTSLTAADTATYFCAR (SEQ ID NO: 4) | 1766.8093 | 1779.8049 | 12.9956 |
| LTAADTATYFCAR (SEQ ID NO: 5) | 1447.6896 | 1460.6842 | 12.9946 |
| Misidentifications | | | |
| DGGIYGTMFNFWGPGTLVTVSSGQPK (SEQ ID NO: 6) | 2716.2971 | — | 12.9949 |
| NYGGAASYGmDLWGPGTLVTVSSGQPK (SEQ ID NO: 7) | — | 2729.2920 | |

Example 3: Development of Novel Bioinformatic Filters for the Correct Identification of Peptide Sequences from High-Resolution Mass Spectrometry Data of Serum Antibodies Standard bioinformatics filters for mass spectrometry analysis of highly complex peptide mixtures involve evaluation of individual spectra independent of cumulative information derived from related spectra originating from the same parent ion. By grouping spectra based on relation to one another, more precise filters can be employed to better discriminate between correct and incorrect sequence identifications. Spectra identified by SEQUEST® as belonging to the same peptide sequence were grouped, and an average was calculated for the difference between the observed experimental mass of parent ions and the theoretical mass of the sequence. This average mass deviation (AMD) was effective in differentiating between "true" and "false" identifications determined by differential cysteine labeling (FIG. 6), and was used as a filter to distinguish between high-confidence peptide sequence identifications and dubious sequence identifications that were subsequently removed from the dataset. Employing a filter cut-off of AMD <1.5 ppm, sequences previously flagged by differential cysteine labeling as misidentifications were removed from the dataset. Table 2 shows representative AMD data for the top 20 most abundant CDRH3 peptides. Those marked with a "*" display an AMD above the threshold and were flagged as misidentifications.

Following filtering to remove peptide sequence misidentifications, the remaining high-confidence peptide sequences were classified as informative CDRH3 (iCDRH3) peptides and non-iCDRH3 (niCDRH3). The iCDRH3 peptides were defined as proteolytic fragmentation products of sufficient length and uniqueness to identify a single CDRH3 in the V sequence database used for LC-MS/MS analysis (defined as the set of NextGen sequences with ≥2 reads). As an example, a peptide corresponding to a unique CDRH3 sequence in the database is classified an iCDRH3 peptide whereas an antibody proteolytic fragmentation product containing amino acids from the J-D region that are found in many CDRH3s is a niCDRH3. Identification of an iCDRH3 thus enables the determination of the corresponding V gene(s) from the DNA database. Only high-confidence iCDRH3 peptide sequences were deemed legitimate candidates for further analysis (Table 3).

TABLE 2

Top 20 most abundant unique CDRH3-containing peptides and their respective average mass deviation (AMD).

| Sequence | SEQ ID NO: | Ave ppm | Spectral Count | AMD > 1.5 ppm |
|---|---|---|---|---|
| MDSHSDGFDPWGPGTLVSVSSGQPK | 8 | 0.0996 | 245 | |
| VCGMDLWGPGTLVTVSSGQPK | 9 | 0.3839 | 232 | |
| DGGIYGTMFNFWGPGTLVTVSSGQPK | 10 | -4.0523 | 197 | * |
| NVAGYLCAPAFNFR | 11 | 0.4799 | 184 | |
| NFKLWGPGTLVTVSSGQPK | 12 | 0.5146 | 152 | |
| NFGLWGPGTLVTVSSGQPK | 13 | 0.3818 | 140 | |
| ELTGNGIYALK | 14 | 0.6036 | 129 | |
| AFNLWGPGTLVTVSSGQPK | 15 | 0.0338 | 125 | |
| SPSSGSSNLWGPGTLVTVSSGQPK | 16 | 0.2109 | 106 | |
| GMDLWGPGTLVTVSSGQPK | 17 | -1.1565 | 105 | |
| GAGWVDYSLWGPGTLVTVSSGQPK | 18 | 0.4812 | 99 | |
| YAPFNLWGPGTLVTVSSGQPK | 19 | 2.9729 | 99 | * |
| GYGSSSDGWLTR | 20 | -0.0177 | 94 | |
| AFTLWGPGTLVTVSSGQPK | 21 | 0.3959 | 91 | |
| NPGGTSNLWGPGTLVTVSSGQPK | 22 | 0.2329 | 87 | |
| APAASTNYGYDLWGPGTLVTVSSGQPK | 23 | 0.1546 | 85 | |
| NSGSASNLWGPGTLVTVSSGQPK | 24 | 0.9042 | 83 | |
| FDFWGPGTLVTVSSGQPK | 25 | 0.0334 | 82 | |
| KFNLWGPGTLVTVSSGQPK | 26 | 0.2351 | 77 | |
| NYGGAASYGMDLWGPGTLVTVSSGQPK | 27 | 2.0078 | 77 | * |

TABLE 3

Top 20 most abundant high-confidence iCDRH3s identified by the analysis pipeline. Amino acids that are designated in lower case indicates that a post translation modification was detected

| Peptide Sequence | SEQ ID NO: | Full v-Gene Degenerate | CDR3 Degenerate | Total Peptide Count | AMD (ppm) |
|---|---|---|---|---|---|
| MDSHSDGFDPWGPGTLVSVSSGQPK | 28 | 1 | 1 | 245 | 0.0996 |
| VcGMDLWGPGTLVTVSSGQPK | 29 | 2 | 1 | 232 | 0.3839 |
| NVAGYLcAPAFNFR | 30 | 1 | 1 | 184 | 0.4799 |
| NFKLWGPGTLVTVSSGQPK | 31 | 13 | 1 | 152 | 0.5146 |
| ELTGNGIYALK | 32 | 1 | 1 | 129 | 0.6036 |
| AFNLWGPGTLVTVSSGQPK | 33 | 1 | 1 | 117 | 0.0338 |
| SPSSGSSNLWGPGTLVTVSSGQPK | 34 | 2 | 1 | 106 | 0.2109 |
| GMDLWGPGTLVTVSSGQPK | 35 | 3 | 1 | 104 | -1.1565 |
| GAGWVDYSLWGPGTLVTVSSGQPK | 36 | 5 | 1 | 99 | 0.4812 |
| GYGSSSDGWLTR | 37 | 1 | 1 | 94 | -0.0177 |
| NPGGTSNLWGPGTLVTVSSGQPK | 38 | 1 | 1 | 87 | 0.2329 |
| APAASTNYGYDLWGPGTLVTVSSGQPK | 39 | 1 | 1 | 85 | 0.1546 |
| NSGSASNLWGPGTLVTVSSGQPK | 40 | 2 | 1 | 83 | 0.9042 |
| FDFWGPGTLVTVSSGQPK | 41 | 1 | 1 | 82 | 0.0334 |
| KFNLWGPGTLVTVSSGQPK | 42 | 3 | 1 | 77 | 0.2351 |
| SDEINDYNLWGPGTLVTVSSGQPK | 43 | 3 | 1 | 74 | 0.1766 |
| AFTLWGPGTLVTVSSGQPK | 44 | 9 | 1 | 70 | 0.3959 |
| NFGLWGPGTLVTVSSGQPK | 45 | 1 | 1 | 69 | 0.3818 |
| NAGTASNLWGPGTLVTVSSGQPK | 46 | 1 | 1 | 61 | 0.5918 |
| NWGLWGPGTLVTVSSGQPK | 47 | 1 | 1 | 55 | 0.0854 |
| DAGDAGYHLTLWGPGTLVTVSSGQPK | 48 | 1 | 1 | 55 | 0.4637 |
| TDSSDHTYFILWGPGTLVTVSSGQPK | 49 | 1 | 1 | 51 | 0.1340 |
| AAGYGADAYAWNLWGPGTLVTVSSGQPK | 50 | 2 | 1 | 51 | 0.2310 |

Example 4: Validation of the Antigen Specificity of the Proteomically-Predicted $V_H$ Sequences Select full-length $V_H$ genes identified by the proteomic pipeline in Example 3 above were synthesized by in-house automated gene synthesis (Cox et al., 2007) with the following modifications. The coding sequences for the selected $V_H$ genes were designed using GeneFab software. After reverse translation of the primary amino acid sequences for each $V_H$ using an E. coli class II codon table, the coding sequences were built with a designed (GGGGS)$_3$ (SEQ ID NO: 192) polyglycine-serine linker at the C-terminus for overlap reassembly scFv construction. A 5' SfiI restriction endonuclease site was added to facilitate cloning of the scFv constructs into the pAK200 phage display vector (Hayhurst et al., 2003). The $V_H$ genes were aligned using the sequence encoding the common Gly-Ser linker sequence and a universal randomly generated stuffer sequence was applied to the ends of the $V_H$ sequences to ensure that all of the constructs were of the same length. The $V_H$ genes were synthesized from overlapping oligonucleotides using a modified thermodynamically balanced inside-out nucleation PCR (Gao et al., 2003). The 80-mer oligonucleotides necessary for the construction of the various scFv genes were designed using the GeneFab software with a minimal overlap of 30 nucleotides between oligonucleotide fragments. The oligonucleotides were synthesized using standard phosphoramidite chemistry at a 50 nmol scale using a Mermade 192 oligonucleotide synthesizer (Bioautomation, TX, USA) using synthesis reagents from EMD Chemical and phosphoramidites from Glen Research. All of the oligonucleotide liquid-handling operations necessary for assembling the various genes were done on a Tecan Evo 200 workstation (Tecan, Calif., USA) with reagent management and instrument control done through the FabMgr software component of the PFA platform (Malmstroem et al., 2009). Gene assembly PCR was performed using KOD-Hotstart polymerase using the buffers and reagents supplied with the enzyme (Novagen, Mass., USA). Table 4 lists the full sequences of the seven $V_H$ genes that were synthesized, notated by the corresponding iCDRH3 peptide identified in the proteomics and mass spectrometry in Example 3. These represent a sample of the highest ranked iCDRH3 that were identified to be antigen-specific based on exclusivity to the elution fraction during affinity chromatography against the target antigen CCH.

TABLE 4

$V_H$ genes synthesized.

| iCDRH3 Rank | iCDRH3 Peptide Sequence | $V_H$ Gene Sequence |
|---|---|---|
| 1 | NVAGYL CAPAFN PR (SEQ ID NO: 51) | ATGGCCCAGCCGGCCATGGCGCAGGAACAGCTGGAAGAATCTG GTGACCTGGTTAAACCGGGTGCTTCTCTGACCCTGACCTGCACC GCTTCTGGTTTCTCTTTCTCTTCTTCTTACTACATGGCTTGGGTTC GTCAGGCTCCGGGTAAAGGTCTGGAATGGATCGGTTGCATGAAC TCTGGTGGTGACACCGCTTACGCTTCTTGGGCTAAAGGTCGTTTC TCTATCTCTAAAACCTCTTCTACCACCATGACCCTGCAGCTGACC TCTCTGACCGCTGCTGACACCGCTACCTACTTCTGCGCTCGTAAC GTTGCTGGTTACCTGTGCGCTCCGGCTTTCAACTTCCGTTCTCCG GGTACCCTGGTTACCGTTTCTTCTGGTGGTGGCGGTAGCGGTGG TGGTGGTAGCGGT (SEQ ID NO: 52) |
| 2 | MDSHSD GFDPWG PGTLVS VSSGQP K (SEQ ID NO: 53) | ATGGCCCAGCCGGCCATGGCGCAGGAACAGCTGGAAGAATCTG GTGGTGACCTGGTTAAACCGGAAGGTTCTCTGACCCTGACCTGC ACCGCTTCTGGTTTCTCTTTCTCTTCTTCTTACTGGATCTGGTGGG TTCGTCAGGCTCCGGGTAAAGGTCTGGAATGGATCGCTTGCATC TACACCGGTTCTGGTACCACCTACTACGCTAACTGGGCTAAAGG TCGTTTCACCATCTCTAAAACCTCTTCTACCACCGTTACCCTGCA GATGACCTCTCTGACCGCTGCTGACACCGCTACCTACTTCTGCGC TCGTATGGACTCTCACTCTGACGGTTTCGACCCGTGGGGTCCGG GTACCCTGGTTTCTGTTTCTTCTGGTGGTGGCGGTAGCGGTGGTG GTGGTAGCGGT (SEQ ID NO: 54) |
| 3 | NFKLWG PGTLVT VSSGQP K (SEQ ID NO: 55) | ATGGCCCAGCCGGCCATGGCGCAGTCTCTGGAAGAATCTGGTGG TGGTCTGGTTAAACCGGGTGGTACCCTGACCCTGACCTGCACCG CTTCTGGTTTCGACTTCTCTTTCTAACCCGATCAACTGGGTTCGTC AGGCTCCGGGTAAAGGTCCGGAATGGATCGGTTACATCAACAA CGGTAACTCTAAAACCTACTACGCTTCTTGGGCTAAAGGTCGTT TCACCATCTCTAAAACCTCTTCTACCACCGTTACCCTGCAGATGA CCTCTCTGACCGCTGCTGACACCGCTACCTACTTCTGCGCTCGTA ACTTCAAACTGTGGGGTCCGGGTACCCTGGTTACCGTTTCTTCTG GTGGTGGCGGTAGCGGTGGTGGTGGTAGCGGT (SEQ ID NO: 56) |
| 4 | VCGMDL WGPGTL VTVSSG QPK (SEQ ID NO: 57) | ATGGCCCAGCCGGCCATGGCGCAGTCTCTGGAAGAATCTGGTGA CCTGGTTAAACCGGGTGCTTCTCTGACCCTGACCTGCACCGCTTC TGGTTTCTCTTTCTCTTCTGGTTACTACATGTGCTGGGTTCGTCA GGCTCCGGGTAAAGGTCTGGAACTGATCGCTTGCATCTACGCTA CCACCTCTGCTACCTACTACGCTTCTTGGGCTAAAGGTCGTTTCA CCATCTCTCAGACCTCTTCTACCACCGTTACCCTGCAGATGACCT CTCTGACCGCTGCTGACACCGCTACCTACTTCTGCGCTCGTAACG TTTACGGTGCTTCTCGTGTTTGCGGTATGGACCTGTGGGGTCCGG GTACCCTGGTTACCGTTTCTTCTGGTGGTGGCGGTAGCGGTGGT GGTGGTAGCGGT (SEQ ID NO: 58) |
| 5 | NPGGTS NLWGPG TLVTVS SGQPK (SEQ ID NO: 59) | ATGGCCCAGCCGGCCATGGCGCAGTCTCTGGAAGAATCTGGTGA CCTGGTTAAACCGGGTTCTTCTCTGACCCTGACCTGCACCGGTTC TGGTTTCTCTTTCTCTAACAAATACTGGATCTGCTGGGTTCGTCA GGCTCCGGGTAAAGGTCTGGAATGGATCGGTTGCATCTACATCG GTAACATCGACAACACCGACTACGCTTCTTGGGCTAAAGGTCGT TTCACCATCTCTTCTACCTCTTCTACCACCGTTACCCTGCAGATG ACCTCTCTGACCGCTGCTGACACCGCTACCTACTTCTGCGCTCGT AACCCGGGTGGTACCTCTAACCTGTGGGGTCCGGGTACCCTGGT TACCGTTTCTTCTGGTGGTGGCGGTAGCGGTGGTGGTGGTAGCG GT (SEQ ID NO: 60) |
| 8 | SPSSGSS NLWGPG TLVTVS SGQPK (SEQ ID NO: 61) | ATGGCCCAGCCGGCCATGGCGCAGCAGCTGGAAGAATCTGGTG ACCTGGTTAAACCGGGTGGTACCCTGACCCTGTCTTGCACCGCT TCTGGTTTCTCTTTCTCTTCTTCTTACTACATGTGCTGGGTTCGTC AGGCTCCGGGTAAAGGTCTGGAATGGATCGCTTGCATCTACACC GGTTCTGGTTCTACCAACTACGCTTCTTGGGCTAAAGGTCGTTTC ACCATCTCTAAATCTTCTTACCACCGTTACCCTGCAGATGACC TCTCTGACCGCTGCTGACACCGCTACCTACTTCTGCGCTCGTTCT CCGTCTTCTGGTTCTTCTAACCTGTGGGGTCCGGGTACCCTGGTT ACCGTTTCTTCTGGTGGTGGCGGTAGCGGTGGTGGTGGTAGCGG T (SEQ ID NO: 62) |
| 10 | GMDLW GPGTLV TVSSGQ PK | ATGGCCCAGCCGGCCATGGCGCAGGAACAGCTGGAAGAATCTG GTGGTCTGGTTCAGCCGGAAGGTTCTCTGACCCTGACCTGCACC GCTTCTGGTTTCTCTTTCACCGTTGGTTACGACATGTGCTGGGTT CGTCAGGCTCCGGGTAAAGGTCTGGAATGGATCGGTTGCATCCC |

TABLE 4-continued

V_H genes synthesized.

| iCDRH3 Rank | iCDRH3 Peptide Sequence | V_H Gene Sequence |
|---|---|---|
| | (SEQ ID NO: 63) | GTCTGCTGACACCACCTACTACGCTTCTTGGGCTAAAGGTCGTTT CACCATCTCTAAAACCTCTTCTACCTCTGTTACCCTGCAGATGAC CCGTCTGACCGTTGCTGACACCGCTACCTACTTCTGCGCTCGTGA AGACACCTACGGTGACGCTAACACCGACTACCTGTACCGTGGTA TGGACCTGTGGGGTCCGGGTACCCTGGTTACCGTTTCTTCTGGTG GTGGCGGTAGCGGTGGTGGTGGTAGCGGT (SEQ ID NO: 64) |

Phage Panning Library Construction.

To analyze the antigen binding affinity and specificity of the identified $V_H$ requires that a $V_L$ be paired to produce a full-length antibody fragment that can then be tested for binding against the target antigen CCH. Combinatorial pairing of the cDNA with each of the synthesized $V_H$ genes was employed to construct a scFv library that was screened for antigen specificity by phage panning. This methodology yielded $V_L$ genes that paired with the synthetic $V_H$ genes to give antibodies with high antigen affinity and specificity.

Rarefaction analysis and species richness estimation (Chao et al., 2009) on the bone marrow (BM) CD138+ $V_L$ high-throughput sequencing data from the immunized animal revealed that the $V_L$ repertoire encoded by bone marrow CD138+ cells consisted of an estimated 10,252 unique CDRL3. Species richness estimation of a sample size (e.g., library size) comprising approximately $10^5$ clones captures 99% of the $V_L$ repertoire. A $V_L$ library was prepared by amplification of periferial blood cell PBC and BM cDNA in a reaction containing: 40.25 μL H_2O, 5 μL 10× Advantage-2 buffer, 2 μL cDNA, 0.75 μL Advantage-2 polymerase mix, 1 μL 10 mM dNTP mix, 0.5 μL 100 μM RLR1/RLR2 equimolar degenerate primer mix, and 0.5 μL 100 μM FLR1 degenerate primer. The PCR program used for $V_H$ amplification described above was used. The PCR product (~400 bp) was gel-purified and quantified with an ND-1000 spectrophotometer. DNA encoding each of the synthetic $V_H$ genes was heated, hybridized, and treated with the SUR-VEYOR mutation detection kit (Transgenomic, NE, USA) according to the manufacturer's protocol. The undigested full-length product for each $V_H$ reaction was gel-purified and quantified using an ND-1000 spectrophotometer. scFv overlap reassembly PCR libraries were prepared in reactions containing: 100 ng of full-length synthetic $V_H$ gene DNA, 50 ng each of gel-purified $V_L$ PCR product from BM CD138+ and PBC CD138+, 5 μL 10× Thermopol buffer (NEB, MA, USA), 0.5 μL Taq DNA polymerase (NEB), 200 μM dNTP mix, 1 μM rabbit $V_H$ forward primer, 1 μM OE-R primer, and filled to 50 μL final volume with ddH_2O. The PCR thermocycle program was 94° C. for 1 min, 25 cycles of amplification (94° C. for 15 sec, 60° C. for 15 sec, 72° C. for 2 min), and a final 72° C. extension for 5 min. The overlap PCR product (~750 bp) was gel-purified twice, digested with SfiI (NEB), and ligated into the pAK200 phage display vector (Krebber et al., 1997). The ligation product was transformed into XL1-Blue E. coli (recA1 endA1 gyrA96 thi-1 hsdR17 supE44 relA1 lac [F' proAB lacIqZΔM15 Tn10 (Tetr)]) to give seven separate libraries (one for each synthesized $V_H$) comprising between $10^6$ and $10^7$ transformants each.

TABLE 5

Primers used for V_L and full length scFV library construction.

| Primer | Sequence | Description of Use |
|---|---|---|
| RLR1 | GATGACGATGCGGCCCCCGAGGCCTTGATTTCYA CMTTGGTGCCAG (SEQ ID NO: 65) | Rabbit V_L repertoire reverse primer mix (equimolar) |
| RLR2 | GATGACGATGCGGCCCCCGAGGCCTYGACSACCA CCTCGGTCCCTC (SEQ ID NO: 66) | Rabbit V_L repertoire reverse primer mix (equimolar) |
| FLR1 | GGTGGTGGTGGTAGCGGTGGTGGTGGCAGCGMN NHHGWDMTGACCCAGACTS (SEQ ID NO: 67) | Rabbit V_L repertoire forward primer |
| VHF-QQL | GGCCCAGCCGGCCATGGCTCAGCAGCTGGAAG (SEQ ID NO: 68) | scFv V_H gene forward primer(s) |
| VHF-QEQ | GGCCCAGCCGGCCATGGCTCAGGAACAGCTG (SEQ ID NO: 69) | scFv V_H gene forward primer(s) |
| VHF-QSL | GGCCCAGCCGGCCATGGCTCAGTCTCTGGAAG (SEQ ID NO: 70) | scFv V_H gene forward primer(s) |
| OE-R | GATGACGATGCGGCCCCCGAG (SEQ ID NO: 71) | scFv gene reverse primer |

Phage Panning of the $V_H$-Restricted scFv Libraries.

Cells for the seven scFv libraries, each comprising a synthetic $V_H$ gene joined to the amplified $V_L$ cDNA library, were scraped from agar plates containing LB, chloramphenicol (35 μg/mL), and 1% w/v glucose and then diluted into 25 mL of 2YT growth media supplemented with chloramphenicol (35 μg/mL), tetracycline (10 μg/mL), and 1% w/v glucose to a final $OD_{600}$ ~0.1. Cells were grown at 37° C. with shaking at 250 rpm until they reached log phase growth ($OD_{600}$ ~0.5), then infected with 100 MOI of M13KO7 helper phage, and incubated without shaking at 37° C. for one hour. The cells were pelleted and resuspended in 25 mL of fresh 2YT media with chloramphenicol (35 µg/mL), kanamycin (35 µg/mL), 1% w/v glucose, and 0.5 mM IPTG. Cultures were grown at 25° C. with shaking at 250 rpm overnight (~14 hours). The cells were pelleted by centrifugation and phage were isolated from the supernatant by PEG-NaCl precipitation. For panning, immunotubes were coated overnight at 4° C. with either BSA or antigen (CCH) resuspended in PBS at 10 µg/mL and then blocked for two hours at room temperature with either 2% milk dissolved in PBS or 3% BSA in PBS (blocking solutions were alternated during sequential rounds of panning) Phage-scFv (dissolved in PBS) were diluted into 2% milk to input $10^{13}$ phage into each of two BSA-coated, blocked immunotubes and rotated end-over-end at room temperature for 1.5 h. One immunotube of the depleted phage-scFv was then directly transferred into a CCH-coated blocked immunotube and the other to a BSA-coated, blocked immunotube. Each immunotube was subsequently rotated at room temperature for two hours for binding of the phage-scFv. The immunotubes were then washed six times with 4 mL PBST (0.05% v/v Tween 20) and four times with 4 mL PBS. Elution was accomplished using 1 mL 100 mM triethylamine, rotating at room temperature for 8 min, and then immediately transferring the solution to a 2 mL microcentrifuge tube containing 700 µL 1.5 M Tris-HCl, pH 8.0. Subsequently, 250 µL of Tris-HCl, pH 8.0 was added directly into the emptied immunotube to neutralize any residual elution solution. Both elution fractions (700 µL and the residual 250 µL) were used to infect 12 mL of log phase *E. coli* XL1-Blue cells, with 3 mL of the culture placed in the neutralized immunotubes to capture remaining bound phage. After one hour at 37° C., the infected culture was plated onto LB agar plates containing chloramphenicol (35 µg/mL) and 1% w/v glucose for titering both the BSA-specific elution and the CCH-specific elution. The entire CCH-specific elution solution (~12 mL infected culture spun down and resuspended in 2 mL 2YT) was spread onto large LB-chloramphenicol-glucose plates and incubated overnight 37° C. Colonies were scraped and cells were resuspended and used for subsequent rounds of phage amplification and panning After three rounds of panning, 10-20 clones were sequenced from each $V_H$-restricted library. For four of the seven $V_H$ examined, a single (or in one case two highly related) $V_L$ was found to pair with each unique $V_H$. These $V_L$ were each unique to their respective $V_H$ and likely represent a native $V_L$ pairing of the $V_H$ in the immunized animal. Table 6 lists the full-length scFv amino acid sequences of the five dominant clones (panned from four $V_H$-restricted libraries) with the iCDRH3 peptide sequence bolded and the CDRL3 sequence underlined.

TABLE 6

Sequences of the five dominant full-length clones isolated from three rounds of phage panning on the $V_H$-restricted libraries.

| $V_H$/Clone ID | scFv Amino Acid Sequence |
|---|---|
| 1 | QEQLEESGDLVKPGASLTLTCTASGFSFSSSYYMAWVRQAPGKGLEWIGCMNS GGDTAYASWAKGRFSISKTSSTTMTLQLTSLTAADTATYFCARNVAGYLCAP AFNFRSPGTLVTVSSGGGGSGGGGSADVMTQTPSSVTAAVGGTVSISCRSSKSVY NNNWLSWYQQKPGQPPKLLIYETSKLPSGVPSRFSGSGSGTQFTLTISDLECDD AATYYC<u>AGGYRSSSD</u>NGFGGGTEVVVK (SEQ ID NO: 72) |
| 2 | QEQLEESGGDLVKPEGSLTLTCTASGFSFSSSYWIWWVRQAPGKGLEWIACIYT GSGTTYYANWAKGRFTISKTSSTTVTLQMTSLTAADTATYFCARMDSHSDGF DPWGPGTLVSVSSGGGGSGGGGSGVELTQTPASVSEPVGGTVTIKCQASQNIY SDLAWYQQKPGQPPKRLIYDASKLPSGVPSRFKGSGSGTEYTLTISDLECADAA TYYC<u>QTYHDFDVYG</u>VAFGGGTEVVVE (SEQ ID NO: 73) |
| 5A2 | QSLEESGDLVKPGSSLTLTCTGSGFSFSNKYWICWVRQAPGKGLEWIGCIYIGNI DNTDYASWAKGRFTISSTSSTTVTLQMTSLTAADTATYFCARNPGGTSNLWG PGTLVTVSSGGGGSGGGGSGAIVLTQTPSSVEAAVGGTVTIKCQASQSIGSILA WYQQKPGQRPKLLIYYASTLASGVPSRFKGSGSGTQFILTISDLECADAATYYC <u>QSYGYSSSGSYGYR</u>NAFGGGTEVVVE (SEQ ID NO: 74) |
| 5F4 | QSLEESGDLVKPGSSLTLTCTGSGFSFSNKYWICWVRQAPGKGLEWIGCIYIGNI DNTDYASWAKGRFTISSTSSTTVTLQMTSLTAADTATYFCARNPGGTSNLWG PGTLVTVSSGGGGSGGGGSGDVVMTQTPSSVEAAVGGTVTIKCQASQSIGNVL AWYQQKPGQRPKLLIYLASTLASGVPSRFKGSGSGTQFILTISDLECADAATYY C<u>QSYGYSSSSSYGYR</u>NAFGGGTEVVVK (SEQ ID NO: 75) |
| 8 | QQLEESGDLVKPGGTLTLSCTASGFSFSSSYYMCWVRQAPGKGLEWIACIYTGS GSTNYASWAKGRFTISKSSSTTVTLQMTSLTAADTATYFCARSPSSGSSNLWG PGTLVTVSSGGGGSGGGGSGDVMTQTPASVSAAVGGTVTIKCQASQSISNYLS WYQQKPGQRPKLLIDAASTLASGVPSRFKGSGSGTESTLTISDLECADAATYYC <u>LYGYYGVSSTS</u>VAFGGGTEVVVE (SEQ ID NO: 76) |

Monoclonal ELISA of Full-Length $V_H$-$V_L$ Clones Panned from the $V_H$-Restricted scFv Libraries.

Figure 2:
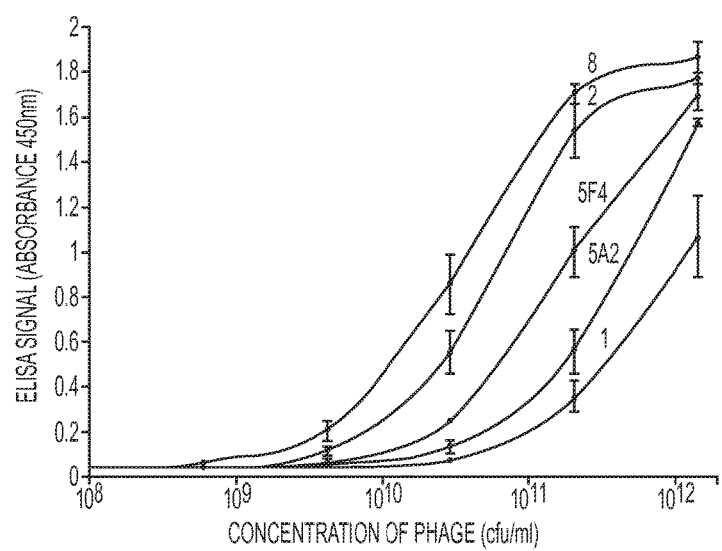
FIG. 2: Monoclonal phage ELISA of antigen-specific scFvs containing the $V_H$ genes corresponding to select abundant iCDRH3s. scFvs were isolated by three rounds of phage display of libraries constructed by pairing each of the synthetic $V_H$ genes with the cDNA $V_L$ library from the immunized animal (Table 6 for $V_H$-$V_L$ sequences). 5A2 and 5F4 represent two clones with the same heavy chain, but paired to a different light chain sequence.

To evaluate binding of the clones obtained by phage panning, single colonies from each $V_H$-$V_L$ library were inoculated into 150 µL 2YT media with chloramphenicol (35 µg/mL), tetracycline (10 µg/mL), and 1% w/v glucose to a final OD$_{600}$ of ~0.5 in a 96-well round bottom plate. Each culture was then infected with 100 MOI of M13KO7 helper phage and incubated at 37° C. for one hour. Cells were then pelleted by centrifugation and resuspended in 25 mL 2YT media with chloramphenicol (35 µg/mL), kanamycin (35 µg/mL), 1% w/v glucose, and 0.5 mM IPTG. Phage displaying scFv antibodies were produced by growing the cells at 25° C. with shaking at 250 rpm overnight (~14 hours). Cells were pelleted by centrifugation and 50 µL of supernatant was transferred to ELISA plates previously coated with CCH (10 µg/mL overnight at 4° C.) and blocked with 2% milk in PBS (two hours, room temperature). An equal volume of 2% milk in PBS was added to each well and phage-scFv were allowed to bind with gentle shaking for one hour. After binding, ELISA plates were washed three times with PBST and incubated with 50 µL of anti-M13-HRP secondary antibody (1:5000, 2% milk in PBS) for 30 min at 25° C. Plates were washed three times with PBST, then 50 µL Ultra TMB substrate (Thermo Scientific) was added to each well and incubated 25° C. for 5 min. Reactions were stopped using equal volume of 1 M $H_2SO_4$ and absorbance was read at 450 nm (BioTek, VT, USA). Dilution series of the purified phage were examined by ELISA as described above, with two replicates of a 7-fold serial dilution of each of the five winners analyzed. The averaged ELISA signals at each phage titer are shown in FIG. 2.

Example 5: J Peptide Synthesis and α-CDR3-J Peptide Antibody Production

CDRH3 is the most hypervariable region in immunoglobulins and is overwhelmingly responsible for antigen specificity. Accordingly, the quantitation and sequence determination of CDRH3 peptides was a primary focus of study. Isolating peptides exhibiting intact CDRH3 regions from a complex peptide mixture improves signal/noise ratio when applying IgG protease digestion products to LC-MS/MS analysis. It was found that CDRH3 containing peptides can be selectively enriched from other antibody proteolytic fragments by affinity chromatography using antibodies specific for J region peptides, i.e., peptides encoded by a portion of the J segment of the V(D)J locus comprising the region of the V gene adjacent to the CDRH3.

Generating peptides including intact CDRH3 regions was based on the selection of the proper proteases. Bioinformatic analysis of the V domain protein sequences revealed that combinations of known proteases can cleave V gene polypeptides in a manner that results in the generation of peptides that cleave N- and C-terminal of the CDR3, leaving the CDR3 sequence largely intact in most sequences. For example, inspection of the V gene database from the immunized rabbit used in Example 1 verified that digestion with trypsin, which cleaves after R/K, should be sufficient to generate peptide fragments comprising amino acids from the CDRH3 region and of lengths appropriate for identification for most of the putative immunoglobulins expressed by the immunized animal (e.g., 91.4% of the putative immunoglobulins expressed by the CCH-immunized rabbit, FIG. 1).

In one embodiment proteolytic cleavage was accomplished using sequencing grade trypsin (Sigma) at 37° C. for 5 h. In a separate embodiment combinations of proteases, such as GluC (Sigma) and LysC (Sigma), were used to generate a distinct set of proteolytic peptides that in computational tests provide better coverage of the CDR3.

Anti-CDRH3-J peptide antibodies were produced in chickens (*Gallus Gallus domesticus*) in order to avoid cross-reactivity between the antibody that was generated and the peptides that were being affinity purified. The J regions of various species were analyzed and lowest similarity was found between J regions of chicken IgY and those of other mammals (Table 7). The N-terminal residues from the CH1 region of these species were different from the chicken CH1 regions as well (Table 8).

TABLE 7

J regions by species.

| Species | J Family | Sequence |
|---|---|---|
| Human | IGHJ1 | GTLVTVSS (SEQ ID NO: 77) |
|  | IGHJ2 | GTLVTVSS (SEQ ID NO: 77) |
|  | IGHJ3 | GTMVTVSS (SEQ ID NO: 78) |
|  | IGHJ4 | GTLVTVSS (SEQ ID NO: 77) |
|  | IGHJ5 | GTLVTVSS (SEQ ID NO: 77) |
|  | IGHJ6 | GTTVTVSS (SEQ ID NO: 79) |
| Rabbit | IGHJ1 | GTLVTISS (SEQ ID NO: 80) |
|  | IGHJ2 | GTLVTVSS (SEQ ID NO: 77) |
|  | IGHJ3 | GTLVTVSS (SEQ ID NO: 77) |
|  | IGHJ4 | GTLVTVSS (SEQ ID NO: 77) |
|  | IGHJ5 | GTLVTVSS (SEQ ID NO: 77) |
|  | IGHJ6 | GTLVTVSS (SEQ ID NO: 77) |
| Mouse | IGHJ1 | GTTVTVSS (SEQ ID NO: 79) |
|  | IGHJ2 | GTTLTVSS (SEQ ID NO: 81) |
|  | IGHJ3 | GTLVTVSA (SEQ ID NO: 82) |
|  | IGHJ4 | GTSVTVSS (SEQ ID NO: 83) |
| Chicken | IGHJ1 | GTEVIVSS (SEQ ID NO: 84) |

TABLE 8

N-terminal sequence of the CH1 domain by species.

| Species | Sequence |
|---|---|
| Human | ASTK (SEQ ID NO: 85) |
| Rabbit | GQPK (SEQ ID NO: 86) |
| Mouse | AK |
|  | AT |
| Chicken | AGPT (SEQ ID NO: 87) |

Figure 3:
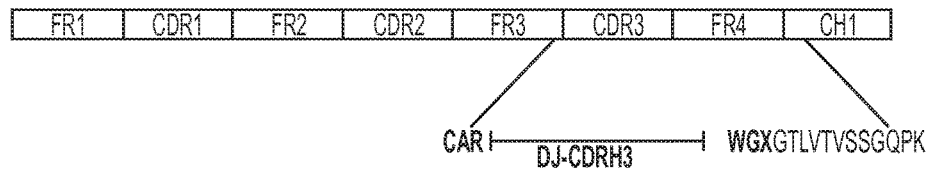
FIG. 3: CDR3-J peptide sequence (in red) based on the rabbit CDRH3 region. The peptide sequence consists of the C-terminal portion of the rabbit J region and four residues from the CH1 region (SEQ ID NO:89).

CDR3-J peptide sequence was designed to exhibit amino acids from the C-terminal portion of the CDRH3 segment, full FR4, and the N-terminal portion of the constant region CH1 (FIG. 3). The sequence CG was padded to the N-terminal of the peptide for conjugation of a carrier protein (e.g., Keyhole Limpet Hemocyanin (KLH, Pierce, Ill.)). The peptide NH2-CGGTLVTVSSGQPK-COOH (SEQ ID NO:88) was synthesized, purified, and the amino acid sequence was validated by MS (Abgent Inc., CA). This peptide was conjugated to KLH as a carrier and the conjugate was used to immunize chickens for IgY production (Ayes Labs Inc., OR).

Figure 4:
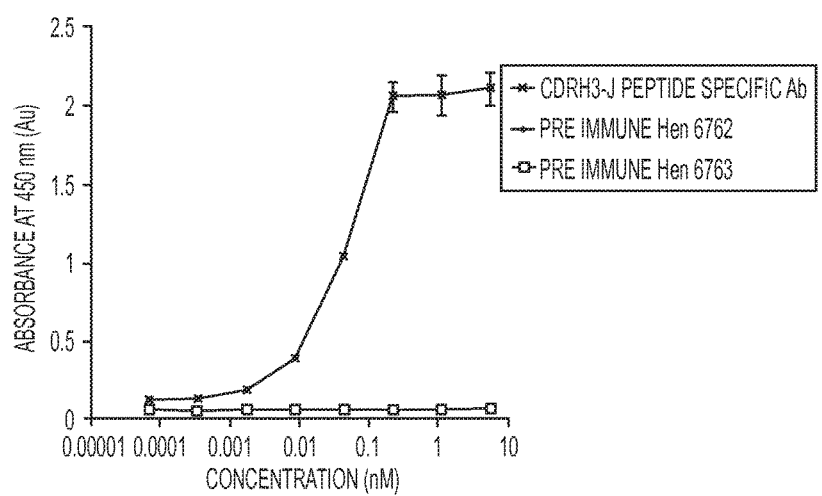
FIG. 4: Polyclonal ELISA of anti-CDRH3-J peptide IgY.

To evaluate the binding affinity of the chicken anti-CDRH3-J peptide antibodies, an ovalbumin-conjugate of the CDRH3-J peptide was first absorbed onto the ELISA plates at a concentration of 1 µg/mL in phosphate-buffered isotonic saline (PBS). After an overnight incubation at 4° C., a 1:100 dilution of BlokHen® (Ayes Labs, diluted in PBS) was added to each well for a two hour incubation at room temperature to block nonspecific sites. After thorough washing, wells on the plate were incubated with varying concentrations of either purified pre-immune IgY (i.e., purified from eggs collected prior to the first injection) or affinity-purified IgY. After a two-hour incubation at 4° C., the plate was washed thoroughly and then incubated with HRP-labeled goat anti-chicken IgY (1:5000 dilution, Ayes Labs) for another one-hour incubation period at room temperature (with rocking). The plate was then washed thoroughly, and HRP activity bound to the plate was determined using ortho-phenylenediamine and stable peroxide substrate buffer (Pierce), following the manufacturer's instructions. Finally, the plate was read by measuring absorbance at 450 nm (FIG. 4).

Example 6: Proteomic Pipeline for CDRH3-J Peptide Isolation

Purified IgG proteins were denatured in 50% 2,2,2-trifluoroethanol (TFE), 10 mM dithiothreitol was added to reduce proteins, samples were incubated at 55° C. for 60 min followed by alkylation with 32 mM iodoacetamide for 60 min at room temperature, and samples were quenched by addition of 7.7 mM DTT for 60 min at room temperature. Samples were diluted 10-fold to 5% TFE concentration and subjected to digestion by appropriate proteases that preserve the CDR3 domains largely intact (e.g., Trypsin, GluC).

Affinity chromatography for the isolation of CDRH3-J peptides was carried out by coupling 100 mg of IgY onto 1 g of dry N-hydroxysuccinimide (NHS)-activated agarose (Pierce, Ill.) by overnight incubation at 4° C. The coupled agarose beads were washed with PBS, incubated with 1 M ethanolamine, pH 8.3 for 60 min at room temperature to block unreated NHS groups, washed with PBS, and packed into a chromatography column. Digested IgG fragments were applied to the affinity column in gravity mode with the flow-through collected and reapplied to the column five times. The column was subsequently washed with PBS and eluted using 100 mM glycine, pH 2.7. MS analysis of the eluent peptide mixture was carried out using the bioinformatics filters described in Example 3.

Figure 5:
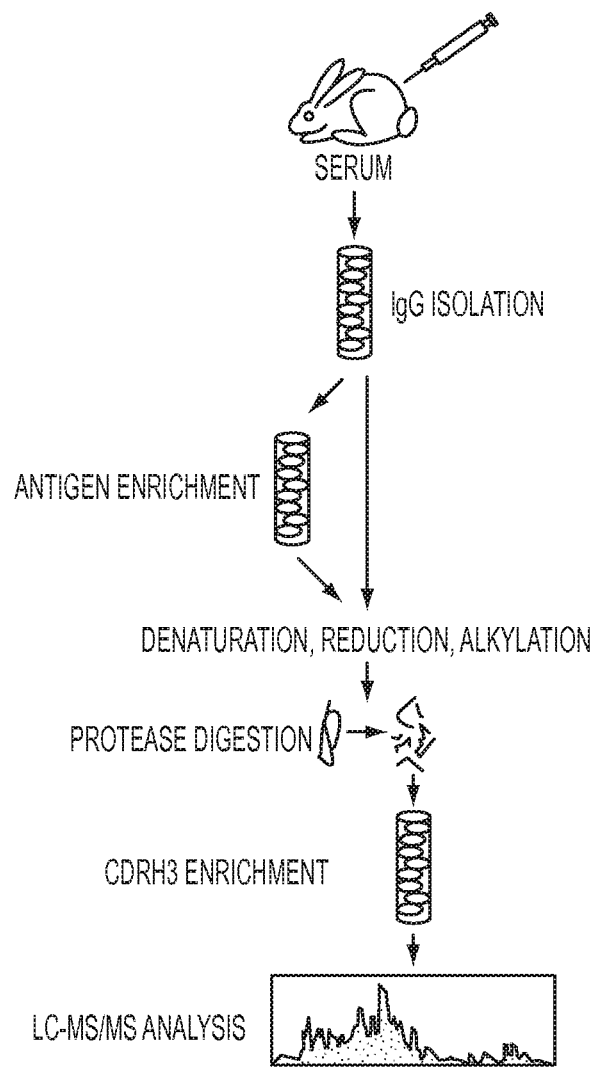
FIG. 5: Schematic of an example CDRH3-J peptide isolation pipeline.

In a separate embodiment, purified serum IgG was first enriched towards antigen-specific IgGs as described in Example 1, followed by anti-CDRH3-J peptide affinity chromatography. In both embodiments, fractions from the affinity chromatography flow through, wash, and elution were collected for LC-MS/MS analysis (FIG. 5).

Example 7: Preparation of Variable Light ($V_L$) and Variable Heavy ($V_H$) Genes for High-Throughput DNA Sequencing RNA Isolation.

CD138$^+$CD45R$^-$ bone marrow plasma cells or peripheral ASC and B cells isolated as described in Examples 2 and 3 above were centrifuged at 2000 rpm and 4° C. for 5 min. Cells were then lysed with TRI reagent and total RNA was isolated according to the manufacturer's protocol in the Ribopure RNA isolation kit (Ambion). mRNA was isolated from total RNA through with oligo(dT) resin and the Poly (A) purist kit (Ambion) according to the manufacturer's protocol. mRNA concentration was measured with an ND-1000 spectrophotometer (Nanodrop).

PCR Amplification.

The isolated mRNA was used for first strand cDNA synthesis by reverse transcription with the Maloney murine leukemia virus reverse transcriptase (MMLV-RT, Ambion). For cDNA synthesis, 50 ng of mRNA was used as a template and oligo(dT) primers were used. RT-PCR was performed using a Retroscript kit (Ambion) according to the manufacturer's protocol. Following cDNA construction, PCR amplification was performed to amplify the $V_L$ and $V_H$ genes using 2 μL of unpurified cDNA product and established $V_L$ and $V_H$ degenerate primer mixes (Krebber et al., 1997; Mazor et al., 2007).

A 50 μL PCR reaction consisted of 0.2 mM of forward and reverse primer mixes, 5 μL of Thermopol buffer (NEB), 2 μL of unpurified cDNA, 1 μL of Taq DNA polymerase (NEB), and 39 μL of double distilled $H_2O$. The PCR thermocycle program was 92° C. for 3 min; 4 cycles of 92° C. for 1 min, 50° C. for 1 min, and 72° C. for 1 min; 4 cycles of 92° C. for 1 min, 55° C. for 1 min, and 72° C. for 1 min; 20 cycles of 92° C. for 1 min, 63° C. for 1 min, and 72° C. for 1 min; 72° C. for 7 min; and 4° C. storage. PCR gene products were gel purified and submitted to SeqWright (Houston, Tex.) and the Genomic Sequencing and Analysis Center at the University of Texas Austin for Roche GS-FLX 454 DNA sequencing.

Rapid cDNA End (RACE) Amplification.

Alternatively, a cDNA amplicon library specific for the variable light ($V_L$) and variable heavy ($V_H$) genes was constructed from the isolated mRNA. To start, first-strand cDNA was synthesized from mRNA using the SMART-Scribe Maloney murine leukemia virus reverse transcriptase (MMLV-RT, Clonetech). The cDNA synthesis utilized 25 ng mRNA and template switching specific 5' primers and 3' gene-specific primers. Buffers and reaction conditions were used according to manufacturer's protocol. Primers were used that already incorporated 454 sequencing primers (Roche) on both 5' and 3' ends along with multiplex identifiers (MID) so that the cDNA synthesized and amplified could be directly used in the 454 emPCR step. The 5' forward primer utilized MMLV-RT template switching by the addition of three cytosine residues at the 3' end of first-strand cDNA along with a portion of the 5' sequencing Primer B of 454 Titanium (SRp#1). For the reverse primer, primers were used to amplify the $V_L$ gene and a small portion of the 3' end of the light chain constant region Cκ along with the Primer A of 454 Titanium including 3 unique MIDs (SRp#2,3,4). Similarly, $V_H$ genes were amplified along with a small portion of the 3' end of the heavy chain constant 1 (CH1) region along with the Primer A of 454 Titanium including 3 unique MIDs (SRp#5,6,7).

Following first-strand cDNA synthesis, PCR was performed to amplify cDNA with primers based on the 5' and 3' ends of the added 454 sequencing primers (SRp#8 and 9, respectively; note that 5' forward primer SRp#8 was biotinylated on the 5' end). Standard PCR conditions were used according to the Advantage 2 PCR kit (Clontech). The cDNA samples were then run on a 1% agarose gel and the bands corresponding to $V_L$ or $V_H$ at ~450 and ~500 bp, respectively, were extracted and further purified (Zymogen). cDNA concentration was measured using a Nanodrop spectrophotometer. Five hundred nanograms of cDNA per sample was then used for 454 sequencing.

High-Throughput Sequencing of $V_L$ and $V_H$ Repertoires.

V gene repertoires isolated from BM CD138$^+$ of eight mice were sequenced using high-throughput 454 GS-FLX sequencing (University of Texas, Austin, Tex.; SeqWright, Houston, Tex.). In total, 415,018 sequences were generated, and 454 data quality control filtered and grouped >97% of the sequences into datasets for each mouse according to their Multiplex Identifiers (MID) usages.

Example 8: Statistical Methods for Determining Antibody Clonotype

A $V_H$ clonotype is the set of genes that derive from the same B cell lineage, and it is generally accepted that members of a clonotype share identical germline V and J segments and show up to 10 or 20% variation within the CDR3 at the amino acid level. The determination of the clonotypes encoded within a set of V gene DNA sequences is critical for the interpretation of IgG proteomic data.

Antibodies that belong to the same clonotype are expected to be derived from the same progenitor B cell and to have the same epitope specificity. The proteomic analysis described in this application enable the determination of antibody clonotypes present in serum via the identification of CDR3 peptides that map to a particular clonotype, as set forth in example 10.

The present example discloses preferred embodiments for the informatics determination of clonotyopes.

To determine the clonotype groupings from sequencing data, CDR3 amino acid sequences were clustered using a variety methods. UCLUST, part of the USEARCH package, returned fragmented clusters that artificially split true-seeming clonotypes at the 80% (amino acid) identity threshold. Because it is a greedy hierarchical algorithm and calculates distance only between a single seed CDR3 and potential members, members of one cluster often matched more closely those of another. This lead to miscalculation of the clonotypes from the analysis of peptide MS from serum IgGs. To address this problem, single-linkage hierarchical clustering was implemented using the following algorithm:
1. Pick an arbitrary CDR3 amino acid (or nucleotide) sequence not belonging to a cluster to seed a new cluster
2. Find all CDR3 amino acid (or nucleotide) sequences above a given similarity to seed and add them to the cluster
3. Mark the seed CDR3 as complete and choose a new seed as the next incomplete CDR3 in cluster
4. Repeat steps 2, 3 until all CDR3s in the cluster are marked as searched
5. Repeat from step 1 until no CDR3s are left unclustered Additionally the following rules were implemented to improve the accuracy of clonotype determination: CDR3s of length 1 to 5 amino acids must be identical, those between 6 and 10 amino acids are allowed a single mismatch, and those of above 10 amino acids must show 90% identity. These requirements allow for length variation of a single residue for CDR3s ranging from 11 to 19 amino acids and two residues for those up to 29 in length.

In addition to the scheme outlined above, dynamic clustering methods such as k-means provide an alternative to the hierarchical methods above and can alternatively be employed for determining the V gene clonotypes encoded by a set of High throughput V gene sequencing data.

Example 9: Deep Sequencing of Human B Cell Populations from the Peripheral Blood at Different Times after Tetanus Toxoid Vaccination In this example the methodology set forth in this application is demonstrated as applied to human samples and specifically to the analysis of the serum antibody repertoire observed after boost immunization with tetanus toxoid.

Two healthy human donors, a 52 year old male and a 35 year old female, each received a booster vaccination against tetanus toxoid (TT)/diphteria toxoid (TD; 20 I.E. TT and 2 I.E. diphteria toxoid, Sanofi Pasteur MSD GmbH, Leimen, Germany). Approximately 40 mL of blood was collected pre-vaccination (day 0) and subsequently at days 7, 56, 109, and ~9 months after vaccination. 10 mL of peripheral blood was collected into a single K-EDTA collection tube (BD Vacutainer REF 367525). The additional 30 mL of peripheral blood was collected into three (3×10 mL) serum collection tubes (BD Vacutainer SST II serum tube, REF 367953), with approximately 15 mL of serum resultant at each time point. Collection of PBCs from the K-EDTA blood was performed by density gradient centrifugation over Histopaque 1077 (Sigma) according to the manufacturer's protocol.

The antibody response to vaccination is probed through establishing a database of the B cell sequences from which the antibody sequence and clonality (origin) is matched via proteomic approaches described in example 11. The relevant B cell populations in the peripheral blood consist of, but are not necessarily limited to: antigen-sorted plasmablasts, total plasmablasts, pre-class switched memory B cells, and post-class switched memory B cells. Total PBCs can also be sequenced with IgG/IgA-specific primers to garner sequence information from total class-switched B cells without prior cell sorting.

FACS Analysis and Sorting of B Cell Populations.

For the two donors receiving the tetanus/diphtheria booster vaccination, PBCs were stained for 15 minutes in PBS/0.2% BSA at 4° C. in the dark using the following antibodies: anti-CD3-Pacific Blue (PacB; clone UCHT1, Becton Dickinson (BD), San Jose, Calif., USA), anti-CD14-PacB (clone M5E2, BD), anti-CD19-Phycoerythrin-Cyanine7 (PECy7, clone SJ25C1, BD), anti-CD27-Cy5 (clone 2E4, BD), anti-CD38-PE (clone HIT2, BD), anti-CD20-Pacific Orange (clone HI47, Invitrogen Corporation, Frederick, Md., USA) and anti-IgD-Peridinin-chlorophyll-protein complex-Cy5.5 (clone L27, BD). TT-specific B cells were identified by binding to TT labelled with digoxigenin (TT-Dig; Novartis Behring, Marburg, Germany), washed in PBS/0.2% BSA, and bound by the secondary antibody anti-Dig-fluorescein isothiocyanate (FITC; Roche Diagnostics GmbH, Mannheim, Germany). Specificity of the staining was confirmed each time by blocking with pure TT. 4,6 diamidino-2-phenylindole (DAPI; Molecular Probes, Eugene, Oreg., USA) was added before cell sorting to exclude dead cells. The following B-cell populations were sorted using a FacsAriaII cell sorter (BD): CD3−CD14−CD19+CD27++CD38++CD20− plasma cells (PC), CD3−CD14−CD19+CD27+CD20+IgD− memory B cells (mBC), CD3−CD14−CD19+CD27+CD20+IgD+ mBC, and CD3−CD14−CD19+CD27++CD38++CD20−TT+ plasma cells (TT+PC).

These B-cell populations were sorted and collected into PBS/0.2% BSA, centrifuged at 500×g for 10 minutes, aspirated, and then resuspended in TRI Reagent Solution (Life Technologies, San Diego, Calif., USA) and then frozen at −80° C. Serum was collected from whole blood by centrifugation at 1100×g for 10 min and then frozen at −80° C. B cell populations of PC, mBC, TT+PC, and TT depleted PC were examined at day 7 after vaccination. At day 109, B cell populations of PC, mBC, and total PBC were sorted/isolated. Further analysis of extended time points after vaccination will allow further analysis of the temporal changes in these B cell populations long into the steady state anti-TT B cell and IgG response.

Amplification of the VH and VL Repertoires from B Cells.

Beginning with B cells lysed and frozen in TRI Reagent, whole RNA was prepared, first-strand cDNA generated, and PCR amplicon libraries generated for Roche 454 or Illumina deep sequencing as previously described (Ippolito et al., *PLoS ONE,* 2012). Briefly, total RNA was isolated according to the manufacturer's RiboPure Kit protocol (Life Technologies). First-strand cDNA generation was performed with 500 ng of isolated total RNA using SuperScript RT II kit (Invitrogen) and Oligo-dT primer. After cDNA construction, PCR amplification was performed to amplify the $V_\lambda$, $V_\kappa$, and $V_H$ genes separately with a respective standard mix of primers as described (Ippolito et al., *PLoS ONE*, 2012) and as listed in Table 9. PCR reactions were carried out using Taq polymerase with Thermpol reaction buffer (New England Biolabs, MA, USA) and the following cycling conditions: 92° C. denaturation for 3 min; 92° C. 1 min, 50° C. 1 min, 72° C. 1 min for 4 cycles; 92° C. 1 min, 55° C. 1 min, 72° C. 1 min for 4 cycles; 92° C. 1 min, 63° C. 1 min, 72° C. 1 min for 20 cycles; and a final extension of 72° C. for 7 minutes. PCR products were gel-purified before sequencing.

Table 9

Primers used for amplification of the VH and VL human repertoires fromB cells

| Primer Name | SEQUENCE (5'->3') | SEQ ID NO: |
|---|---|---|
| $V_H$ | | |
| VH1-fwd | CAGGTCCAGCTKGTRCAGTCTGG | 90 |
| VH157-fwd | CAGGTGCAGCTGGTGSARTCTGG | 91 |
| VH2-fwd | CAGRTCACCTTGAAGGAGTCTG | 92 |
| VH3-fwd | GAGGTGCAGCTGKTGGAGWCY | 93 |
| VH4-fwd | CAGGTGCAGCTGCAGGAGTCSG | 94 |
| VH4-DP63-fwd | CAGGTGCAGCTACAGCAGTGGG | 95 |
| VH6-fwd | CAGGTACAGCTGCAGCAGTCA | 96 |
| VH3N-fwd | TCAACACAACGGTTCCCAGTTA | 97 |
| IgM-rev | GGTTGGGGCGGATGCACTCC | 98 |
| IgG-all-rev | SGATGGGCCCTTGGTGGARGC | 99 |
| IgA-all-rev | GGCTCCTGGGGGAAGAAGCC | 100 |
| Vκ | | |
| VK1-fwd | GACATCCRGDTGACCCAGTCTCC | 101 |
| VK246-fwd | GATATTGTGMTGACBCAGWCTCC | 102 |
| VK3-fwd | GAAATTGTRWTGACRCAGTCTCC | 103 |
| VK5-fwd | GAAACGACACTCACGCAGTCTC | 104 |
| VK1-rev | TTTGATTTCCACCTTGGTCC | 105 |
| VK2-rev | TTTGATCTCCASCTTGGTCC | 106 |
| VK3-rev | TTTGATATCCACTTTGGTCC | 107 |
| VK5-rev | TTTAATCTCCAGTCGTGTCC | 108 |
| Vλ | | |
| VL1-fwd | CAGTCTGTSBTGACGCAGCCGCC | 109 |
| VL1459-fwd | CAGCCTGTGCTGACTCARYC | 110 |
| VL15910-fwd | CAGCCWGKGCTGACTCAGCCMCC | 111 |
| VL2-fwd | CAGTCTGYYCTGAYTCAGCCT | 112 |
| VL3-fwd | TCCTATGWGCTGACWCAGCCAA | 113 |
| VL3-DPL16-fwd | TCCTCTGAGCTGASTCAGGASCC | 114 |
| VL3-38-fwd | TCCTATGAGCTGAYRCAGCYACC | 115 |
| VL6-fwd | AATTTTATGCTGACTCAGCCCC | 116 |
| VL78-fwd | CAGDCTGTGGTGACYCAGGAGCC | 117 |

Table 9-continued

Primers used for amplification of the VH and VL human repertoires fromB cells

| Primer Name | SEQUENCE (5'->3') | SEQ ID NO: |
|---|---|---|
| VL1-rev | TAGGACGGTSASCTTGGTCC | 118 |
| VL7-rev | GAGGACGGTCAGCTGGGTGC | 119 |

High-throughput sequencing of VH and VL repertoires. V gene repertoires isolated from sorted B cell populations of both vaccinated human donors were sequenced using high-throughput 454 GS-FLX sequencing (University of Texas, Austin, Tex.; SeqWright, Houston, Tex.). In total, between the two vaccinated human donors, >220,000 VH sequences and >16,000 VL sequences were generated after raw 454 nucleotide data passed quality control and length cutoff filters. Both VH and VL sequences were subsequently grouped according to unique full length V gene amino acid sequence for generation of the sequence database utilized for proteomic bioinformatics. Sequences were also further grouped by unique CDR-H3 amino acid sequence for clonotype analysis.

Example 10: Proteomic Analysis of the Serum Antibodies to Tetanus Toxoid in Human Volunteers Serum was collected from human volunteers at day 0 (pre-immune), day 7, day 109 and day 256 following immunization with tetanus toxoid as described in example 8. For each time point, ~7-10 mL of serum was diluted 4-fold with Protein G binding buffer (Pierce, Ill.), filtered, and passed over a Protein G affinity column. The diluted serum was recycled three times over the column, which was subsequently washed with 15 volumes of PBS, and eluted with 5 volumes of 100 mM glycine-HCl, pH 2.7. The purified IgG was dialyzed into 20 mM sodium acetate, pH 4.5 and concentrated to 10 mg/mL. Approximately 40-80 mg of protein G-purified IgG was digested with 1 mL immobilized pepsin resin (Pierce, Ill.) per 10 mg of IgG in 20 mM sodium acetate. Pepsin digestion was allowed to proceed for seven hours, shaking vigorously at 37° C. The digestion of the IgG into F(ab)$_2$ was monitored by SDS-PAGE to ensure >95% cleavage.

Affinity chromatography for the isolation of antigen-specific F(ab)$_2$ was carried out by coupling 5 mg of the antigen, TT, onto 0.25 g of dry N-hydroxysuccinimide (NHS)-activated agarose (Pierce, Ill.) by overnight incubation at 4° C. The coupled agarose beads were washed with PBS and unreacted NHS groups were blocked with 1 M ethanolamine, pH 8.3 for 30 min at room temperature, washed with PBS, and packed into a chromatography column. The column was then washed with 5 volumes of 100 mM glycine, pH 2.7 to elute non-specifically bound (unconjugated) antigen and then 5 volumes of PBS to equilibrate. F(ab)$_2$ fragments (from ~40-80 mg of IgG) were applied to the antigen affinity column in gravity mode, with the flow-through collected and reapplied to the column three times. The column was subsequently washed with 15 volumes of PBS, 5 volumes of ddH$_2$O, and eluted using 1 mL fractions of 20 mM HCl, pH 1.7. The flow-through, wash, and each 1 mL elution fraction (neutralized with NaOH/Tris) were analyzed by indirect ELISA against TT to monitor affinity purification. Elution fractions showing an ELISA signal were combined and concentrated under vacuum to ~0.5 mL volume and the combined, concentrated affinity column elution was desalted into ddH$_2$O using a 2 mL Zeba spin column (Pierce, Ill.).

The combined, desalted elution and an aliquot of the flow-through from the antigen affinity chromatography were each denatured in 50% v/v TFE, 50 mM ammonium bicarbonate, and 10 mM DTT at 60° C. for 60 min. The denatured, reduced F(ab')$_2$ were then alkylated by incubation with 32 mM iodoacetamide (Sigma, MO) for one hour at room temperature and then quenched by addition of 20 mM DTT for one hour at room temperature. Denatured, alkylated F(ab')$_2$ samples were diluted 10-fold into 50 mM sodium bicarbonate to reach a final TFE concentration of 5% v/v. Trypsin digestion was carried out by adding trypsin at a ratio of 1:35 trypsin:protein and incubated overnight at 37° C. Digestion was halted by addition of formic acid to 1% final concentration.

Peptides derived from proteolytic digestion were subject to chromatographic separation on a C18 reverse phase tip, eluted with 60% acetonitrile in 0.1% TFA. C18 elution was dried under vacuum to ~5 ul and diluted to ~50 ul to 5% acetonitrile in 0.1% TFA. Peptides were injected onto an LTQ Orbitrap™ Velos mass spectrometer (Thermo Scientific) using a Nano-spray source. The LTQ Orbitrap Velos was operated in the data dependent mode with scans collected at 60,000 resolutions. Ions with charge >+1 were selected for fragmentation by collision-induced dissociation with a maximum of 20 fragmentation scans per full scan.

The resulting spectra from above were searched against a protein sequence custom database consisting of a human full protein-coding sequence database (ENS64) combined with in-house human V$_H$ and V$_L$ sequences, using SEQUEST® (Proteome Discoverer 1.2, Thermo Scientific). The search specified tryptic peptides with up to two missed tryptic cleavages allowed. A precursor mass tolerance of 5 ppm was used, with fragment mass tolerance set to 0.8 Da. Static cysteine modifications carbamidomethylation (iodoacetamide) was included as well as oxidized methionine was allowed as a dynamic modification. The confidence of peptide identifications was determined using the Percolator algorithm as part of the Proteome Discoverer software package (Thermo Scientific), with only top-ranked peptide identifications at <1% FDR considered.

Following filtering to remove peptide sequence misidentifications, the remaining high-confidence peptide sequences were classified as informative CDRH3 (iCDRH3) peptides and non-iCDRH3 (niCDRH3). The iCDRH3 peptides were defined as proteolytic fragmentation products of sufficient length and uniqueness to identify a TT specific clonotype in the V sequence database (See example 8 for definition and determination of clonotype) used for LC-MS/MS analysis. As an example, a peptide corresponding to a unique clonotype in the database is classified an iCDRH3 peptide whereas an antibody proteolytic fragmentation product containing amino acids from the J-D region that are found in many clonotypes is a niCDRH3. Identification of an iCDRH3 thus enables the determination of the corresponding V gene(s) from the DNA database. Only high-confidence iCDRH3 peptide sequences were deemed legitimate candidates for further analysis (top-ranked protein-spectrum matches (PSMs) at <1% FDR as determined by Percolator). Additionally, to further increase confidence in the identification of the proteolytic peptides, only peptides observed in 3 injections were considered as legitimate and clonotype frequencies within each sample were calculated using peptides derived only from the CDRH3 region.

Figure 9:
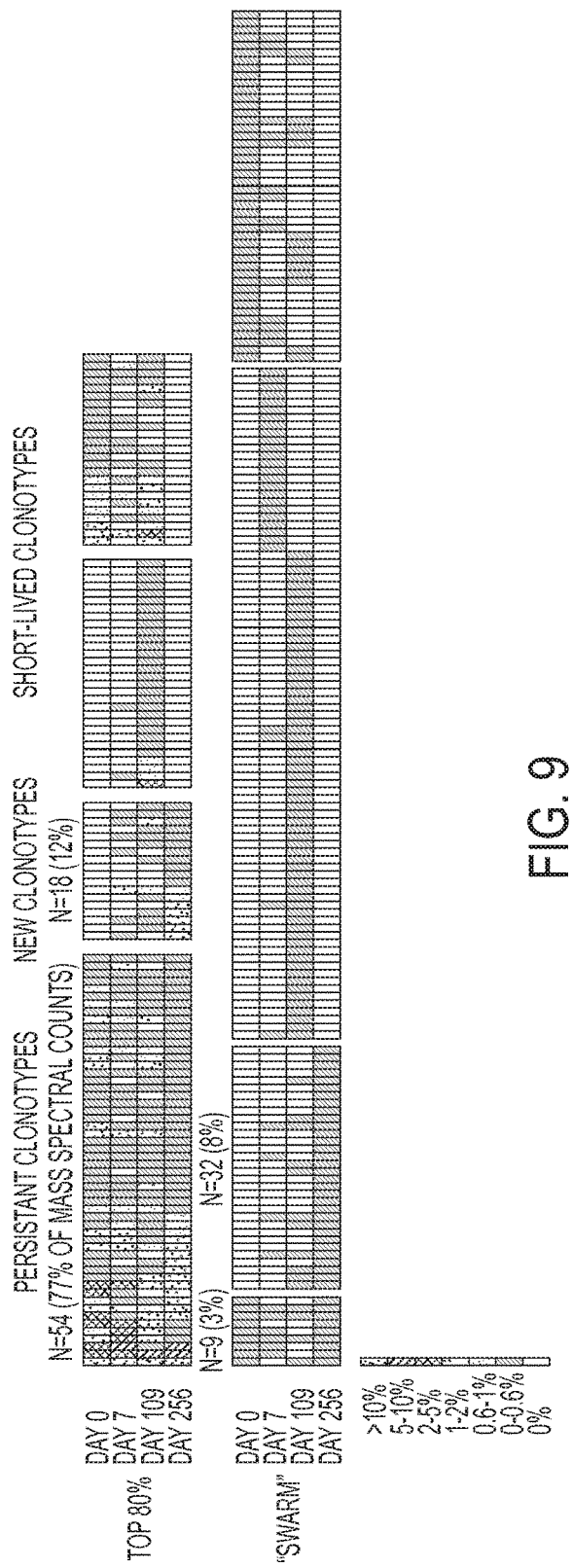
FIG. 9: A mass spectral count heat map of proteomically identified TT-specific serum IgG clonotypes in a healthy donor (HD2) across each of the four time points examined. The heat map is vertically split into two populations of TT-specific IgG clonotypes. Clonotypes that are identified in the top 80% (by frequency of mass spectral counts) of any of the four time points are included in the top heat map, whereas clonotypes not present at the 80% cutoff at any time point are considered "swarm" clonotypes that are only present at very low levels. This donor exhibited 54 IgG clonotypes persistent across all four time points, representing 77% of the heavy chain CDR3-peptide mass spectral counts in the TT affinity column elution fraction at day 256 (steady state after vaccination). An additional 18 new clonotypes (12% of day 256 mass spectral counts) are identified at day 256 were not present at day 0. A number of short lived clonotypes are also identified at earlier time points, but are not detected at steady state post-vaccination.

Following analysis of proteomic high confidence identified peptides, a heatmap was constructed to reflect the temporal changes of clonotypes (as shown in FIG. 9). Over 250 VH genes were identified with high confidence as shown in FIG. 9. Clonotypes were grouped into the following groups: i) persistent clonotypes that appear at all time points; ii) new clonotypes that do not appear in the sample taken pre-immunization; iii) short lived clonotypes that do not appear at steady state time point (day 256) and iv) low abundance (or low frequency) "swarm" colonotypes that appear at low frequencies in any time point. Groups i-iii accounted for peptides that comprise 80% of the spectral counts in the sample and the "swarm" group accounts for the remaining 20% of the spectral counts.

Figure 8:
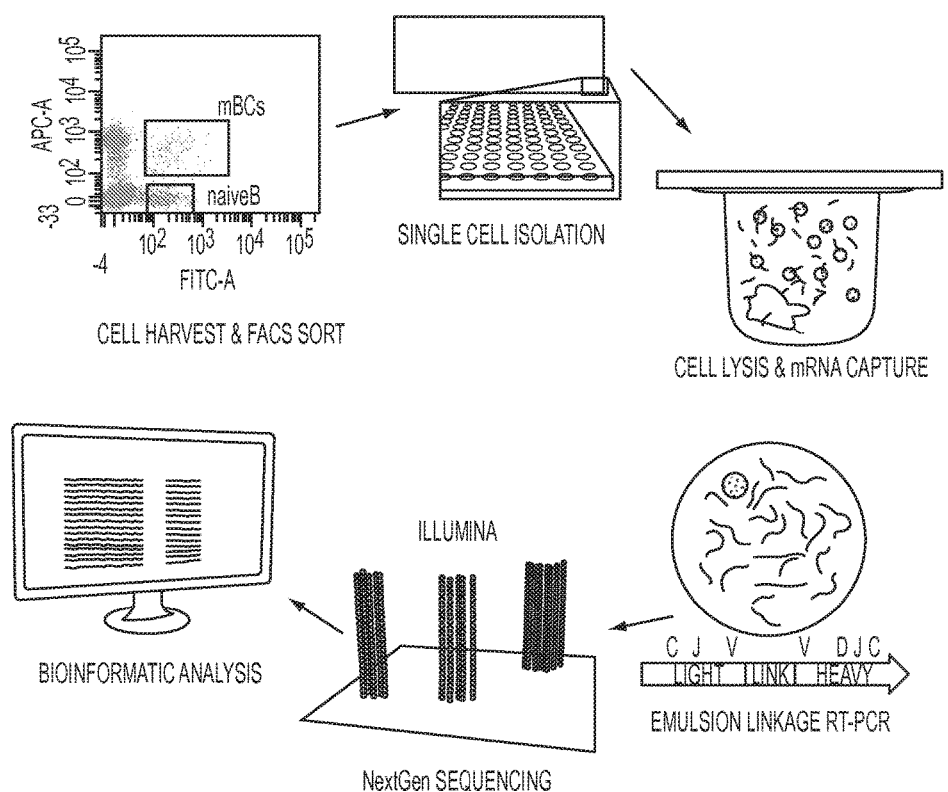
FIG. 8: Determination of the paired VH:VL genes in peripheral B lymphocytes. The specific embodiment in Example 11 refers to B cells isolated from a volunteer immunized with the tetanus toxoid vaccine. Cells are deposited in pL wells containing poly(dT) beads, wells are covered with a dialysis membrane and equilibrated with lysis buffer, then the beads with captured mRNA from lysed cells are recovered and emulsified for cDNA synthesis and linkage PCR to produce a VH:VL product. NextGen sequencing is then used to determine linked VH:VL pairs.

Example 11: High Throughput Determination of the VL Amino Acid Sequences Natively Paired with VH Sequences Determined by MS Proteomic Analysis The method of Example 10 describes the proteomic determination of antibody VH chains. To generate functional antibodies it is important to also identify the cognizant VL chains that pair properly with the identified V$_H$ chains to give fully functional antibodies. One such method was described in Example 4. The method set forward in this Example describes an alternate method for identifying the native V$_H$:V$_L$ pairs encoded by single B lymphocytes. Briefly the native V$_H$:V$_L$ pairs encoded by single B lymphocyte cells in a population are determined by first capturing V$_H$ and V$_L$ mRNA from single cells on beads, the carrying out reverse transcription and linking PCR to generate an approximately 850 bp DNA product that comprises the V$_H$ and V$_L$ nucleotide sequences and then using high throughput (NextGen) DNA sequencing to determine the sequence of the V$_H$ and V$_L$ genes from single cells (FIG. 8). Once a set of native V$_H$ and V$_L$ genes derived from individual B cells in a B lymphocyte population has been determined then the resulting database of V$_H$:V$_L$ pairs is employed to identify a V$_L$ gene that natively pairs with a V$_H$ sequence, the later having been identified proteomically as described in Example 10 above.

Specifically, at 7 days post tetanus toxoid immunization, EDTA blood was withdrawn and PBC isolated by density gradient separation. PBCs were stained in PBS/BSA at 4° C. for 15 min with anti-human CD3/CD14-PacB (clone UCHT1 and M5E2, respectively, Becton-Dickinson, BD), CD19-PECy7 (clone SJ25C1, BD), CD27-Cy5 (clone 2E4, kind gift from Rene van Lier, Academic Medical Centre, University of Amsterdam, The Netherlands, labelled at the Deutsches Rheumaforschungszentrum (DRFZ), Berlin), CD20-PacO (clone HI47, Invitrogen), IgD-PerCpCy5.5 (clone, L27, BD), CD38-PE (clone HIT2, BD), and TT-Digoxigenin (labeled at the DRFZ) for 15 minutes at 4° C. Cells were washed and a second staining was performed with anti-Digoxigenin-FITC (Roche, labeled at the DRFZ) and DAPI was added prior to sorting. CD19$^+$ CD3$^-$ CD14$^-$ CD38$^{++}$ CD27$^{++}$ CD20$^-$ TT$^+$ plasmablasts were sorted using a FACSAria II sorter system (BD Biosciences). A portion of sorted cells were washed and cryopreserved in DMSO/10% FCS for high-throughput VH:VL pairing.

One vial containing approximately 2,000 frozen TT$^+$ plasmablasts was thawed and recovered by centrifugation at 250×g for 10 minutes. Cells were resuspended in 300 µL RPMI-1640 supplemented with 1×GlutaMAX, 1× non-essential amino acids, 1× sodium pyruvate and 1× penicillin/streptomycin (all from Life Technologies) and incubated at 37° C. for 13 hours in a 96-well plate. Recovered cells were centrifuged again at 250×g for 10 minutes and resuspended in 400 L PBS, and 6 μL were withdrawn for cell counting with a hemocytometer.

Cells were deposited by gravity into 125 pL wells molded in polydimethylsiloxane (PDMS) slides (each slide contained 1.7×10⁵ wells). Poly(dT) magnetic beads with a diameter of 2.8 nm were subsequently deposited into the microwells at an average of 55 beads/well and the slide were covered with a dialysis membrane (FIG. 8). 25 μL of poly(dT) magnetic beads (Invitrogen mRNA Direct Kit) were resuspended in 50 uL PBS and distributed over each PDMS slide surface, (mean of 55 poly(dT) beads per well). The magnetic beads were allowed to settle into wells by gravity for approximately 5 minutes, then a BSA-blocked dialysis membrane (12,000-14,000 MWCO regenerated cellulose, 25 mm flat width, Fisher Scientific) that had been rinsed in PBS was laid over each slide surface, sealing the microwells and trapped cells and beads inside. Excess PBS was removed from the slide and membrane surfaces using a 200 μL pipette. 500 μL of cell lysis solution (500 mM LiCl in 100 mM tris buffer (pH 7.5) with 1% lithium dodecyl sulfate, 10 mM EDTA, and 5 mM DTT) was applied to the dialysis membranes for 20 min at room temperature. Time-lapse microscopy revealed that all cells are fully lysed within 1 minute. Subsequently the slides were incubated at 4° C. for 10 min at which point a Dynal MPC-S magnet was placed underneath the PDMS microwell device to hold magnetic beads inside the microwells as the dialysis membrane was removed with forceps and discarded. The PDMS slides were sequentially inverted in a Petri dish containing 2 mL of cold lysis solution and the magnet was applied to force the beads out of the microwells. Subsequently 1 ml aliquots of the lysis solution containing resuspended beads were placed into Eppendorf tubes and beads were pelleted on a Dynal MPC-S magnetic rack and washed once without resuspension using 1 mL per tube of wash Buffer 1 (100 mM Tris, pH 7.5, 500 mM LiCl, 1 mM EDTA, 4° C.). Beads were resuspended in wash Buffer 1, pelleted and resuspended in Wash Buffer 2 (20 mM Tris, pH 7.5, 50 mM KCl, 3 mM MgCl) and pelleted again. Finally beads were suspended in 2.85 mL cold RT-PCR mixture (Quanta OneStep Fast, VWR) containing 0.05 wt % BSA (Invitrogen Ultrapure BSA, 50 mg/mL) and primer sets for VH and VL amplification (Table 10) The suspension containing the poly(dT) magnetic beads was added dropwise to a stirring IKA dispersing tube (DT-20, VWR) containing 9 mL chilled oil phase (molecular biology grade mineral oil with 4.5% Span-80, 0.4% Tween 80, 0.05% Triton X-100, v/v % (Sigma Aldrich, St. Louis, Mo.), and the mixture was agitated for 5 minutes at low speed. The resulting emulsion was added to 96-well PCR plates with 100 μL emulsion per well and placed in a thermocycler. The RT step was performed under the following conditions: 30 minutes at 55° C., followed by 2 min at 94° C. PCR amplification was performed under the following conditions: four cycles of 94° C. for 30 s denature, 50° C. for 30 s anneal, 72° C. for 2 min extend; four cycles of 94° C. for 30 s denature, 55° C. for 30 s anneal, 72° C. for 2 min extend; 22 cycles of 94° C. for 30 s denature, 60° C. for 30 s anneal, 72° C. for 2 min extend; then a final extension step for 7 min at 72° C. After thermal cycling the emulsion was collected and centrifuged at room temperature for 10 minutes at 16,000×g, the mineral oil upper phase was discarded, and 1.5 mL diethyl ether was added to extract the remaining oil phase and break the emulsion. The upper ether layer was removed, two more ether extractions were performed and residual ether was removed in a SpeedVac for 25 minutes at room temperature. The aqueous phase was diluted 5:1 in DNA binding buffer and passed through a silica spin column (DNA Clean & Concentrator, Zymo Research, Irvine, Calif.) to capture the cDNA product. The column was washed twice with 300 μL wash buffer (Zymo Research Corp) and cDNA was eluted into 40 μL nuclease-free water. Finally a nested PCR amplification was performed (ThermoPol PCR buffer with Taq Polymerase, New England Biosciences, Ipswich, Mass.) in a total volume of 200 μL using 4 μL of eluted cDNA as template with 400 nM primers (Table 11) under the following conditions: 2 min initial denaturation at 94° C., denaturation at 94° C. for 30 s for 39 cycles, annealing at 62° C. for 30 s and extension at 72° C. for 20 s, final extension at 72° C. for 7 min. The approximately 850 bp linked product was extracted by agarose gel electrophoresis and sequenced using the 2×250 paired end MiSeq NextGen platform (Illumina, San Diego, Calif.).

The ~850 base pair (bp) linked $V_H$:VL DNA product (comprising 5'→3' a sequence encoding the N-terminal end of CH1, the $V_H$, a linker region, the $V_L$ and the N-terminal of Cκ or Cλ) is generated and the most informative 500 bp of this fragment encompassing the CDR-H3 and CDR-L3 was sequenced on 2×250 Illumina™ MiSeq (providing also the FR3 and FR4 and constant region N-termini amino acid sequences for isotype assignment). CDR-H3:CDR-L3 sequences and thus the corresponding $V_H$:$V_L$ pairs derived from single lymphocytes) were identified.

TABLE 10

RT-PCR primer mix for single cell VH;VL linkage (SEQ ID NOs: 159-186, respectively)

| Primer ID | Sequence |
|---|---|
| CHrev-AHX89 | CGCAGTAGCGGTAAACGGC |
| CLrev-BRH06 | GCGGATAACAATTTCACACAGG |
| hIgG-rev-OE-AHX89 | CGCAGTAGCGGTAAACGGC AGGGYGCCAGGGGGAAGAC |
| hIgA-rev-OE-AHX89 | CGCAGTAGCGGTAAACGGC CGGGAAGACCTTGGGGCTGG |
| hIgM-rev-OE-AHX89 | CGCAGTAGCGGTAAACGGC CACAGGAGACGAGGGGGAAA |
| hIgKC-rev-OE-BRH06 | GCGGATAACAATTTCACACAGG GATGAAGACAGATGGTGCAG |
| hIgLC-rev-OE-BRH06 | GCGGATAACAATTTCACACAGG TCCTCAGAGGAGGGYGGGAA |
| hVH1-fwd-OE | TATTCCCATGGCGCGCCCAGGTCCAGCTKGTRCAGTCTGG |

TABLE 10-continued

RT-PCR primer mix for single cell VH;VL linkage (SEQ ID NOs: 159-186, respectively)

| Primer ID | Sequence |
|---|---|
| hVH157-fwd-OE | TATTCCCATGGCGCGCCCAGGTGCAGCTGGTGSARTCTGG |
| hVH2-fwd-OE | TATTCCCATGGCGCGCCCAGRTCACCTTGAAGGAGTCTG |
| hVH3-fwd-OE | TATTCCCATGGCGCGCCGAGGTGCAGCTGKTGGAGWCY |
| hVH4-fwd-OE | TATTCCCATGGCGCGCCCAGGTGCAGCTGCAGGAGTCSG |
| hVH4-DP63-fwd-OE | TATTCCCATGGCGCGCCCAGGTGCAGCTACAGCAGTGGG |
| hVH6-fwd-OE | TATTCCCATGGCGCGCCCAGGTACAGCTGCAGCAGTCA |
| hVH3N-fwd-OE | TATTCCCATGGCGCGCCTCAACACAACGGTTCCCAGTTA |
| hVK1-fwd-OE | GGCGCGCCATGGGAATAGCCGACATCCRGDTGACCCAGTCTCC |
| hVK2-fwd-OE | GGCGCGCCATGGGAATAGCCGATATTGTGMTGACBCAGWCTCC |
| hVK3-fwd-OE | GGCGCGCCATGGGAATAGCCGAAATTGTRWTGACRCAGTCTCC |
| hVK5-fwd-OE | GGCGCGCCATGGGAATAGCCGAAACGACACTCACGCAGTCTC |
| hVL1-fwd-OE | GGCGCGCCATGGGAATAGCCCAGTCTGTSBTGACGCAGCCGCC |
| hVL1459-fwd-OE | GGCGCGCCATGGGAATAGCCCAGCCTGTGCTGACTCARYC |
| hVL15910-fwd-OE | GGCGCGCCATGGGAATAGCCCAGCCWGKGCTGACTCAGCCMCC |
| hVL2-fwd-OE | GGCGCGCCATGGGAATAGCCCAGTCTGYYCTGAYTCAGCCT |
| hVL3-fwd-OE | GGCGCGCCATGGGAATAGCCTCCTATGWGCTGACWCAGCCAA |
| hVL-DPL16-fwd-OE | GGCGCGCCATGGGAATAGCCTCCTCTGAGCTGASTCAGGASCC |
| hVL3-38-fwd-OE | GGCGCGCCATGGGAATAGCCTCCTATGAGCTGAYRCAGCYACC |
| hVL6-fwd-OE | GGCGCGCCATGGGAATAGCCAATTTTATGCTGACTCAGCCCC |
| hVL78-fwd-OE | GGCGCGCCATGGGAATAGCCCAGDCTGTGGTGACYCAGGAGCC |

TABLE 12

Nested PCR primers for VH;VL linkage (SEQ ID NOs: 187-191, respectively)

| Primer ID | Sequence |
|---|---|
| hIgG-all-rev-OEnested | ATGGGCCCTGSGATGGGCCCTTGGTGGARGC |
| hIgA-all-rev-OEnested | ATGGGCCCTGCTTGGGGCTGGTCGGGGATG |
| hIgM-rev-OEnested | ATGGGCCCTGGGTTGGGGCGGATGCACTCC |
| hIgKC-rev-OEnested | GTGCGGCCGCAGATGGTGCAGCCACAGTTC |
| hIgLC-rev-OEnested | GTGCGGCCGCGAGGGYGGGAACAGAGTGAC |

Example 12: Construction and Characterization of Proteomically Identified Tetanus Toxoid Specific Antibodies This example describes the evaluation of the antibodies identified by proteomic analysis of the VH chains as set forth in example 10. Since antibodies comprise of a $V_H$ and $V_L$ chain construction of antibodies requires the identification of the correct $V_L$ sequence. For this purpose we took advantage of the database of natively paired $V_H$ and $V_L$ genes in single B cell lymphocytes disclosed in Example 11 above. In other words, the VH gene is first identified proteomically and then the natively paired VL gene encoded by a clonal B cell is identified as set forth in Example 11. To evaluate the antigen binding affinity of the $V_H$ and $V_L$ sequences, proteomically identified $V_H$ genes and their natively paired $V_L$ genes (Table 10) were synthesized using gBlocks™ Gene Fragments (IDT, integrated DNA technologies). Synthesized $V_H$ and $V_L$ were cloned separately into pMAZ-IgH and pMAZ-IgL vector backbone (1), using Gibson Assembly™ Master Mix (2) and transformed into E. coli Jude-1 strain and sequence was validated.

After sequence validation, 20 μg of each $V_H$ and $V_L$ were purified, sequence verified and co-transfected into HEK 293F cells following the Freestyle MAX expression system instructions (Invitrogen, NY, USA). HEK 293F cells were grown for 6 days after transfection and medium was harvested by centrifugation and IgG was purified by a protein-A agarose (Pierce, Ill., USA) chromatography column.

IgG affinities for Tetanus toxoid (TT) were determined by competitive ELISA using different concentrations of IgG in a serial dilution of antigen, ranging from 50 nM to 0.02 nM in the presence of 2% milk in PBS. The list of $V_H$ and $V_L$ sequences are shown in Table 13. The concentrations of IgG used were chosen based on the signal given in an initial indirect ELISA in which a dilution series of each IgG was analyzed, with the IgG concentrations analyzed being in the linear range of the initial ELISA. Each sample was incubated overnight at room temperature to equilibrate. Plates were coated overnight at 4° C. with 10 μg/mL of TT in 50 mM carbonate buffer, pH 9.6. Coated plates were washed three times in 0.1% PBST and blocked with 2% milk in PBS for two hours at room temperature. Equilibrated samples were then added to the block plate and incubated for one hour at room temperature. After binding, ELISA plates were washed 3× with 0.1% PBST and incubated with 50 μl of anti-human kappa-HRP secondary antibody (Sigma, 1:2,500 in 2% milk in PBS) for 30 min, 25° C. Plates were washed 3× with 0.1% PBST, then 50 μl Ultra TMB substrate (Thermo Scientific) was added to each well and incubated 25° C. for 5 min. Reactions were stopped using equal volume of 1M $H_2SO_4$ and absorbance was read at 450 nm (BioTek, VT, USA). Monoclonal antibodies, Kg's, HTS sequences frequencies, temporal frequencies and CDRH3's are shown in Table 14.

TABLE 13

Amino acid sequences of synthesized VH and VL polypeptides specific for tetanus toxoid and identified by proteomic analysis of the serum from vaccinated patients..

| Name | Sequence | SEQ ID NO: |
|---|---|---|
| VH-1 | QVQLVESGGGLVQPGRSLRLSCVGSGFSFESYAMHWVRLAPGKGLEW VAGISWDSGAKGNADSVEGRFTISRDNAKKSVYLEMRSLRPEDTAFYY CAKAPIIGPKYYFYMDVWGKGTSVTVSS | 120 |
| VH-2 | QVQLVQSGGGVKQPGGSLRLSCTASGFTFEDFNMHWVRQAPGKGLE WISYISGDGDRTHYSDSVRGRFTISRDNSGNSLYLQMTSLRTEDAGFYY CGKSYDYIRENLDSWGQGTLVTVSS | 121 |
| VH-3 | QVQLVQSGAEVKKPGASVRVSCKASGYTFTRYAMHWVRQAPGQRPE WMGWINVDNGNTEYSQKFQGRLTITRDTSASTAYMELSSLTSDDTAV YYCAKDRVRVVQAATTLDFWGQGTLVTVSS | 122 |
| VH-4 | QVTLKESGPALVKPTQTLTLTCTFSGFSLLSSGMCVSWIRQPPGKALEW LARIDWDEKKYYSPSLKTRLTISKDTSKDQVVLTMTNMDPLDTAMYS CARGVVPAGIPFDFWGQGIMVTVSS | 123 |
| VH-5 | QVQLQESGPGLVKPSETLSLTCTVSGGSINSYYWSWIRQSPGKGLEWIG YIYYTGINKYNPSLKSRVTISMDTSKRQVSLKVTSLTPADTAVYFCARL HPTCASTRCPENYGMDVWGQGTTAVSS | 124 |
| VH-6 | QVQLQESGGKLVRPGGRLRLSCVVSGFTFSDFAMSWVRQAPGKGPLW VAAVSGSGDETFYADSVKGRFTISRDNSKNTIFLQMTSLGVEDTALYY CVRDPRHYHNMGRYYAGWFDAWGQGTRVIVSS | 125 |
| VH-7 | QVQLVESGSEVRKPGASVKVSCKASGYTFSRYGLTWVRQAPGQGLEW MGWISGYNSNTNYAPKFQGRVTMTTDTSTNTAYLELRSLRSNDTAVY YCARDYFHSGSQYFFDYWGQGSLVTVSS | 126 |
| VH-8 | QVQLQESGPGLVRPSQTLSLTCTVSGDSISDGDSFWSWIRQPPGKGPEW IGYISSSGTTYYYPSLRGRLTVSLDASKNQFSLSLTSVTAADTAVYYCA RARNYGFPHFFDFWGRGTLVTVSS | 127 |
| VH-9 | QVQLVESGGGLVKPGGSLRLSCAASGFSFSHYSMNWIRQAPGKGLEW VASITSGSTNMVYADSLRARFSISRDNAKNSLYLQMDSLSAEDTAVYY CARKGMGHYFDFWGQGTPVTVSS | 128 |
| VH-10 | QVQLQESGPGLVKPSGTLSLTCAVSGVPVYTGHWWTWVRQAPGKGL EWIGEIHHTVTTNYNPSLRSRVTISEDRSKNQISLTLQSVTAADTAVYFC ARGEDCVGGSCYSADWGQGILVTVSS | 129 |
| VH-11 | QVQLQESGGGLVQPGRSLRLSCVGSGFSFESYAMHWVRQAPGKGLEW VAGISWDSGAKGNADSVEGRFTISRDNAKKSLYLEMRSLRPEDTAFYY CAKAPIIGPKHYFYMDVWGKGTSVTVSS | 130 |
| VH-12 | QFKLVESGSWGKKPGSSVKVSCKASGDTLTSYVITWLRQAPGQGPEW MGEIITMFGTTKFANNFHGRMTITVDELKTTAYMELTSLRSEDTAVYY CARQRPSPRWAFDIWGQGTMVTVSS | 131 |
| VH-13 | QVQLVESGAEVKKPGASVRVSCKASGYTFTNYGLAWVRQAPGQGLE WMGWITVYNGHTSYAQKFHDRVTMTTDTSTRTAYLEVRNLGSDDTA VYYCARKPRFYYDTSAWFEFWGQGTLVTVSS | 132 |
| VL-1 | EIVLTQSPGTLSLSPGERATLSCRASQRVKSSYLAWYQQKPGQAPRLLI YDASTRATGIPDRFSGSGSGTDFTLTISRLEPEDVAVYYCQQYGTSRGT FGQGTRLEIK | 133 |
| VL-2 | QPGLTQPPSVSVAPGQTARITCGGNNIGSRHVHWYQQRPGQAPVLVVY DDDARPSGISGRFSGSNSGNTATLTISWVEAGDEADYYCQVSDSGREW GVFGSGTKVTVL | 134 |

TABLE 13-continued

Amino acid sequences of synthesized VH and VL polypeptides specific for tetanus toxoid and identified by proteomic analysis of the serum from vaccinated patients..

| Name | Sequence | SEQ ID NO: |
|---|---|---|
| VL-3 | EIVLTQSPGTLSLSPGERATLSCRASQTIPSKYLGWYQQKLGQAPRLLIY GASSRATGIPDRFSGSGSGTDFTLTISRLEPEDFAVYYCQQYGSLSAITF GQGTRLEIK | 135 |
| VL-4 | ETTLTQSPSTLPASVGDRVTITCRASENINSWLAWYQQKPGKAPKILIY RASNLESGVPSRFSGSGSGTEFTLTISSLQPDDFATYYCQHFDKYFSWTF GHGTKVEIK | 136 |
| VL-5 | DIRLTQSPSSLSASVGDRVTITCRSSQTISTYLNWYQQKPGEAPKILIYA ASSLHTGVPSRFSGSGSGTDFTLTITSLQPEDFAIYHCQQSYSTPYTFGQ GTKVEIK | 137 |
| VL-6 | DIRVTQSPESLGMSLGERATLNCKSNQSLLYTSKNYLAWYQQKPGQPP KLLIYWASTRQSGVPARFSGSGSGTDFTLTISSLEAEDVAVYYCQQYYD TPSFGPGTKVDIK | 138 |
| VL-7 | DIRLTQSPSSLSASVGDRVTITCRSSQTISTYLNWYQQKPGEAPKILIYA ASSLHTGVPSRFSGSGSGTDFTLTITSLQPEDFAIYHCQQSYSTPYTFGQ GTKVEIK | 139 |
| VL-8 | DIQMTQSPSTLSASVGDSVTITCRASQSITRWLAWYQQKPGKAPKLLIY KASLLESGVPSRFSGSGSGTEFTLTISSLQPDDFATYYCQQYNSYSPWTF GPGTKLEIK | 140 |
| VL-9 | QTVVTQEPSSSVSLGGTVTLTCGLTSGPVTGAYYPSWHQQTPGQAPRT LIYNTYSLSSGVSDRFSGSILGNKAALTISGAQADDESDYYCVLYMGSG IWMFGGGTKLTVL | 141 |
| VL-10 | EIVLTQSPSSLSASVGDRVTITCRASQNIHLFLNWYQQRPGRVPKVLIYA TSTLQSGVPSRFSGSGSGTDFTLTISSVQPEDFATYYCQQSFSTPRTFG PGTKVEIK | 142 |
| VL-11 | EIVLTQSPGTLSLSPGERATLSCRASQRVKSSYLAWYQQKPGQAPRLLI YDASTRATGIPDRFSGSGSGTDFTLTISRLEPEDVAVYYCQQYGTSRGT FGQGTRLEIK | 143 |
| V1-12 | DIQMTQSPSTLSASVGDRVSITCRASQSISGWLAWYQQKPGKAPKLLIY KASSLENGVPSRFSGSGSGTEFTLTISSLQPDDFATYYCQQYNSYSPSTF GQGTKVEIK | 144 |
| VL-13 | DIVLTQSPETLSVSPGESATLSCRASQSVSTDLAWYQHKPGQAPRLLIW GASTRATGIPARFSGSGSGTEFTLTISSLQSEDFAICFCHQYNNWPTFGQ GTKVEIK | 145 |

TABLE 14

Antibodies specific to tetanus toxoid identified by proteomic deconvolution of the serum IgG response as specified in Examples 10-12. VH genes encoding serum IgG antibodies induced by Tetanus toxoid immunization were identified proteomically as set forth in example 10, the native VL genes encoded by B lymphocytes expressing these VH genes were identified as in the Example 11, then the VH and VL genes were synthesized, cloned into IgG expression vectors, expressed in HEK293F cells purified and the affinities were measured by competition ELISA as set forth in Example 12.

| mAb | $K_D$ (nM) Equilibrium Dissociation Constant | Standard error in KD (nM) | CDR3 (CDR3 Length; SEQ ID NO:) |
|---|---|---|---|
| TT-1 | 1.6 | 0.04 | AKAPIIGPKYYFYMDV (16; 146) |
| TT-2 | 22.6 | 9 | CGKSYDYIRENLDS (14; 147) |
| TT-3 | 3.7 | 0.5 | AKDRVRVVQAATTLDF (16; 148) |

TABLE 14-continued

Antibodies specific to tetanus toxoid identified by proteomic deconvolution of the serum IgG response as specified in Examples 10-12. VH genes encoding serum IgG antibodies induced by Tetanus toxoid immunization were identified proteomically as set forth in example 10, the native VL genes encoded by B lymphocytes expressing these VH genes were identified as in the Example 11, then the VH and VL genes were synthesized, cloned into IgG expression vectors, expressed in HEK293F cells purified and the affinities were measured by competition ELISA as set forth in Example 12.

| mAb | $K_D$ (nM) Equilibrium Dissociation Constant | Standard error in KD (nM) | CDR3 (CDR3 Length; SEQ ID NO:) |
|---|---|---|---|
| TT-4 | 3.2 | 0.5 | ARGVVPAGIPFD (12; 149) |
| TT-5 | 18.1 | 3.6 | ARLHPTCASTRCPENYGM (18; 150) |
| TT-6 | 0.6 | 0.03 | ARDYFHSGSQYFFDY (15; 152) |
| TT-7 | 0.5 | 0.01 | ARARNYGFPHFFDF (14; 153) |
| TT-8 | 2.8 | 0.3 | ARKGMGHYFDF (11; 154) |
| TT-9 | 0.1 | 0.008 | ARGEDCVGGSCYSAD (15; 155) |
| TT-10 | 0.9 | 0.03 | AKAPIIGPKHYFYMDVW (17; 156) |
| TT-11 | 1.6 | 0.05 | ARKPRFYYDTSAWFEF (16; 158) |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 8,043,621
Browning et al., Nature, 175:570-575, 1955.
Clackson et al., Nature, 352:624-628, 1991.
Cobaugh et al., J. Mol. Biol., 378(3):622-633, 2008
Cox et al., Protein Sci., 16:379-390, 2007.
de Costa et al., J. Proteome Res., 9:2937-2945, 2010.
Dekker et al., Analy. Bioanalyt. Chem., 399:1081-1091, 2011.
EP 171496
EP 173494
EP 194276
EP 239400
Feldhaus et al., Nat. Biotechnol., 21:163-170, 2003.
Fox et al., Methods Mol. Biol., 553:79-108, 2009.
Gao et al., Nucleic Acids Res., 31:e143, 2003.
Gibson, et al. Enzymatic assembly of DNA molecules up to several hundred kilobases. Nat. Methods. 6, 343-345 (2009).
Harlow and Lane, In: Antibodies: A Laboratory Manual, Cold Spring Harbor Laboratory, Cold Spring Harbor, N.Y., 346-348, 1988.
Harvey et al., Proc. Natl. Acad. Sci. USA, 101:9193-9198, 2004.
Hayhurst et al., J. Immunol. Methods, 276:185-196, 2003.
Hoogenboom, Nat. Biotechnol., 23:1105-1116, 2005.
Hosse et al., Protein Sci., 15:14-27, 2006.
Hu et al., J. Mass. Spectrom., 40:430-443, 2005.
Hunt et al., Proc. Natl. Acad. Sci. USA, 83:6233-6237, 1986.
Ippolito et al., PLOS One, 7(4):e35497, 2012.
Ishihama et al., Mol. Cell Proteomics, 4:1265-1272, 2005.
Jackson et al., Adv. Immunol., 98:151-224, 2008.
Jin et al., Nat. Med., 15:1088-1092, 2009.
Kantha, J. Med., 40:35-39, 1991.
Keller et al., Anal. Chem., 74:5383-5392, 2002.
Kohler and Milstein, Nature, 256:495-497, 1975.
Krebber et al., J. Immunol. Methods, 201:35-55, 1997.
Kretzschmar and von Ruden, Curr. Opin. Biotech., 13:598-602, 2002.
Kwakkenbos et al., Nat. Med., 16:123-128, 2010.
Link et al., Nat. Biotechnol., 17:676-682, 1999.
Liu et al., Anal. Chem., 76:4193-4201, 2004.
Love et al., Nat. Biotechnol., 24: 703-707, 2006.
Lu et al., Nat. Biotechnol., 25:117-124, 2007.
Malmstroem et al., Nature, 460:762-U112, 2009.
Malmstrom et al., Nature, 460(7256):762-5, 2009.
Marcotte, Nat. Biotechnol., 25:755-757, 2007.
Mazor et al., J. Immunol. Methods, 321, 41-59, 2007.
Mazor et al., Nat. Biotechnol., 25:563-565, 2007.
Meijer et al., J. Molec. Biol., 358:764-772, 2006.
Nesvizhskii et al., Anal. Chem., 75:4646-4658, 2003.
Olsen et al., Nat. Methods, 4:709-712, 2007.
Ong and Mann, Nat. Chem. Biol., 1:252-262, 2005.
Pandey and Mann, Nature, 405:837-846, 2000.
PCT Appln. WO 89/01782
PCT Appln. WO 89/01974
PCT Appln. WO 89/02465
Persson et al., J. Mol. Biol., 357:607-20, 2006.
Radbruch et al., Nat. Rev. Immunol., 6:741-750, 2006.
Radbruch et al., Nat. Rev. Immunol., 6:741-750, 2006.
Reddy et al., Nat. Biotechnol., 28:965-U920, 2010.
Schaffitzel et al., J. Immunol. Meth., 231:119-135, 1999.
Scheid et al., Nature, 458:636-640, 2009.
Shevchenko et al., Proc. Natl. Acad. Sci. USA, 93:14440-14445, 1996.
Silva et al., Mol. Cell Proteomics, 5(4):589-607, 2006b.
Silva et al., Mol. Cell Proteomics, 5:144-156, 2006a.
Smith et al., Nat. Protoc., 4:372-384, 2009.
Tatusova et al., FEMS Microbiol Lett., 174(2):247-50, 1999.
Traggiai et al., Nat. Med., 10:871-875, 2004.
Vogel and Marcotte, Nature Protocols, 3:1444-1451, 2008.
Washburn et al., Nat. Biotechnol., 19:242-247, 2001.
Weinstein et al., Science, 324:807-810, 2009.
Wrammert et al., Nature, 453:667-671, 2008.
Zahnd et al., Nat. Methods, 4:269-279, 2007.

What is claimed is:

1. A method for determining antibody sequences in circulation from a subject, wherein the subject has a tumor, an infectious disease, an autoimmune disease, has been immunized or has been exposed to an antigen which is an infectious agent, a tumor antigen, a tumor cell or a self-antigen, comprising:
   a) obtaining mature B cells from the subject;
   b) isolating nucleic acids encoding VH and VL gene repertoires encoded by the mature B cells of the subject, and sequencing the isolated nucleic acids using a high-throughput sequencing method, wherein the high-throughput sequencing method is selected from the group consisting of sequencing-by-synthesis, sequencing-by-ligation, sequencing-by-hybridization, single molecule DNA sequencing, multiplex polony sequencing and nanopore sequencing, and determining the nucleic acid sequence and the corresponding amino acid sequence information of the VH and VL gene repertoires encoded by mature B cells of a subject;
   c) isolating antibodies from the biological fluid of the subject and preparing CDR3-containing peptide fragments derived from the isolated antibodies, separating the peptide fragments using chromatography, and generating mass spectra of the separated CDR3-containing peptide fragments;
   d) using the nucleic acid sequence information and the mass spectra to determine the amino acid sequence of VH and VL regions of one or more antibodies in circulation of the subject;
   e) preparing expression vectors encoding the one or more antibodies or antigen-binding fragments identified in circulation of the subject in step d); and
   f) expressing the one or more antibodies or antigen-binding fragments from said expression vectors in a host cell.

2. The method of claim 1, where in the mature B cells are from peripheral blood.

3. The method of claim 1, where in the mature B cells are from a lymphoid organ.

4. The method of claim 1, wherein step a) comprises determining the nucleic acid sequences and the corresponding amino acid sequences of rearranged antibody VH and VL.

5. The method of claim 1, wherein the mature B cells comprise memory B cells.

6. The method of claim 1, wherein the mature B cells comprise plasma cells.

7. The method of claim 1, wherein step b) comprises the use of high performance liquid chromatography (HPLC).

8. The method of claim 1, wherein step c) further comprises isolating or enriching a selected class of serum antibodies.

9. The method of claim 1, wherein step c) further comprises isolating or enriching serum antibodies that bind to a predetermined antigen.

10. The method of claim 1, wherein each of the antibodies or antigen-binding fragments so expressed in step f) comprises similarly abundant amino acid sequences of VH and VL or is part of a cluster of highly homologous amino acid sequence which are similarly abundant.

11. The method of claim 1, wherein the antibodies or antigen-binding fragments so expressed in step e) bind an antigen the subject has or has been exposed to with a monovalent affinity of about 100 pM to 5 µM.

12. The method of claim 1, further comprising evaluating binding affinity of the antibody or antigen-binding fragments so expressed in step e) toward a predetermined antigen.

* * * * *

UNITED STATES PATENT AND TRADEMARK OFFICE
CERTIFICATE OF CORRECTION

PATENT NO. : 10,175,249 B2  
APPLICATION NO. : 14/865302  
DATED : January 8, 2019  
INVENTOR(S) : Jason Lavinder et al.

Page 1 of 1

It is certified that error appears in the above-identified patent and that said Letters Patent is hereby corrected as shown below:

On the Title Page

Item (56) References Cited, Foreign Patent Documents, delete "WO 2010-082456" and insert --WO 2010-083456-- therefor.

Signed and Sealed this  
Sixteenth Day of July, 2019

Andrei Iancu  
*Director of the United States Patent and Trademark Office*